(12) United States Patent
Sternson et al.

(10) Patent No.: US 8,435,762 B2
(45) Date of Patent: May 7, 2013

(54) CHIMERIC LIGAND-GATED ION CHANNELS AND METHODS OF USE THEREOF

(75) Inventors: Scott Sternson, Reston, VA (US); Loren Looger, Sterling, VA (US); Peter Lee, Reston, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 97 days.

(21) Appl. No.: 12/576,934

(22) Filed: Oct. 9, 2009

(65) Prior Publication Data

US 2010/0130420 A1    May 27, 2010

Related U.S. Application Data

(60) Provisional application No. 61/136,856, filed on Oct. 9, 2008.

(51) Int. Cl.
| | |
|---|---|
| C07K 14/705 | (2006.01) |
| C07K 19/00 | (2006.01) |
| C12N 15/12 | (2006.01) |
| C12N 15/62 | (2006.01) |
| G01N 33/567 | (2006.01) |

(52) U.S. Cl.
USPC ......... 435/69.7; 435/7.21; 530/350; 536/23.4

(58) Field of Classification Search .................. None
See application file for complete search history.

(56) References Cited

U.S. PATENT DOCUMENTS

| | | | |
|---|---|---|---|
| 4,605,652 | A | 8/1986 | Welstead, Jr. |
| 6,323,000 | B2 | 11/2001 | Briggs et al. |
| 6,693,172 | B1 | 2/2004 | Groppi, Jr. et al. |
| 7,003,352 | B1 | 2/2006 | Whitehurst |
| 7,067,626 | B2 | 6/2006 | Benjamin et al. |
| 2003/0167476 | A1 | 9/2003 | Conklin |
| 2003/0194720 | A1 | 10/2003 | Roberds et al. |
| 2005/0154045 | A1 | 7/2005 | Luithle et al. |
| 2005/0255551 | A1 | 11/2005 | Bencherif et al. |
| 2007/0041947 | A1 | 2/2007 | Barber et al. |
| 2007/0238168 | A1 | 10/2007 | Groppi et al. |
| 2008/0234311 | A1 | 9/2008 | Li et al. |
| 2009/0123945 | A1 | 5/2009 | Gopalakrishnan et al. |

FOREIGN PATENT DOCUMENTS

| | | |
|---|---|---|
| EP | 0158532 | 10/1985 |
| EP | 0237281 | 9/1987 |
| EP | 0240180 | 10/1987 |
| EP | 0272052 | 6/1988 |
| EP | 0306345 | 3/1989 |
| EP | 0327335 | 8/1989 |
| EP | 0353371 | 2/1990 |
| EP | 0353372 | 2/1990 |
| WO | WO 00/73431 | 12/2000 |
| WO | WO 03/055914 | 7/2003 |
| WO | WO 2004/033498 | 4/2004 |

OTHER PUBLICATIONS

Quiram et al. Identification of Residues in the Neuronal alpha7 Acetylcholine Receptor That Confers Selectivity for Conotoxin lml, May 1, 1998, The Journal of Biological XChemistry 273(18):11001-11006.*
Brown et al. "Synthesis and Activity of a Novel Series of 3-Biarylquinuclidine Squalene Synthase Inhibitors," Journal of Medicinal Chemistry, vol. 39: 2971-2979, 1996.
Langlois et al. "Derivatives of quinuclidine as 5-HT3 receptor antagonists: influence of an additional carbonyl group on the recognition of chirality by the receptor," Bioorganic & Medicinal Chemistry Letters, vol. 3: 1555-1558, 1993.
Armbruster et al. "Evolving the lock to fit the key to create a family of G protein-coupled receptors potently activated by an inert ligand," Proc. Natl. Acad. Sci. USA, vol. 104: 5163-5168, 2007.
Luo et al. "Genetic dissection of neural circuits," Neuron, vol. 57: 634-660, 2008.
Galzi et al. "Functional significance of aromatic amino acids from three peptide loops of the alpha 7 neuronal nicotinic receptor site investigated by site-directed mutagenesis," FEBS letters, vol. 294: 198-202, 1991.
Celie et al. "Nicotine and carbamylcholine binding to nicotinic acetylcholine receptors as studied in AChBP crystal structures," Neuron, vol. 41: 907-914, 2004.
Eisele et al. "Chimaeric nicotinic-serotonergic receptor combines distinct ligand binding and channel specificities," Nature, vol. 366: 479-483, 1993.
Grutter et al. "Molecular tuning of fast gating in pentameric ligand-gated ion channels," Proc. Natl. Acad. Sci. USA, vol. 102: 18207-18212, 2005.
Bodnar et al. "Discovery and structure-activity relationship of quinuclidine benzamides as agonists of alpha7 nicotinic acetylcholine receptors," Journal of Medicinal Chemistry, vol. 48: 905-908, 2005.
Walker et al. "Design, synthesis, structure-activity relationship, and in vivo activity of azabicyclic aryl amides as alpha7 nicotinic acetylcholine receptor agonists," Bioorganic & Medicinal Chemistry, vol. 14: 8219-8248, 2006.
Baker et al. "High affinity ligands for the alpha7 nicotinic receptor that show no cross-reactivity with the 5-HT3 receptor," Bioorganic & Medicinal Chemistry Letters, vol. 15: 4727-4730, 2005.
Craig et al. "Stable expression and characterisation of a human alpha 7 nicotinic subunit chimera: a tool for functional high-throughput screening," European Journal of Pharmacology, vol. 502: 31-40, 2004.
Hu et al. "Mutations of L293 in transmembrane two of the mouse 5-hydroxytryptamine3A receptor alter gating and alcohol modulatory actions," British Journal of Pharmacology, vol. 148: 88-101, 2006.

(Continued)

*Primary Examiner* — John Ulm
(74) *Attorney, Agent, or Firm* — Stites & Harbison PLLC; Mandy Wilson Decker

(57) ABSTRACT

The present invention provides novel chimeric receptors that have unique pharmacology. In particular, the chimeric receptors comprise a mutated ligand binding domain of the α7 nicotinic acetylcholine receptor fused to a transmembrane or channel domain from a ligand-gated ion channel protein. The mutations in the ligand binding domain confer selective binding of compounds. Methods of using the novel chimeric receptors of the invention as well as compounds that preferentially bind and activate the chimeric receptors are also disclosed.

60 Claims, 15 Drawing Sheets

OTHER PUBLICATIONS

Sugiyama et al. "Residues at the Subunit Interfaces of the Nicotinic Acetylcholine Receptor that Contribute to α-Conotoxin M1 Binding," Molecular Pharmacology, vol. 53: 787-794, 1998.

Sine et al. "Naturally Occurring Mutations at the Acetylcholine Receptor Binding Site Independently Alter Ach Binding and Channel Gating," J. Gen. Physiol., vol. 120: 483-496, 2002.

Young, "International Search Report and Written Opinon," 18 pages, from International Patent Application No. PCT/US09/60136, USPTO, Alexandria, Virginia, US (mailed Aug. 5, 2010).

Magnus, et al.; Chemical and Genetic Engineering of Selective Ion Channel-Ligand Interactions; Science; 333, 2011; pp. 1292-1296.

Bodnar, et al.: Discovery and Structure—Activity Relationship of Quinuclidine Benzamides as Agonists of a7 Nicotinic Acetylcholine Receptors; J. Med. Chem; 2005; 48, 905-908.

Jensen, et al.: Pharmacological Characterisation of Strychnine and Brucine Analogues at Glycine and a7 Nicotinic Acetylcholine Receptors; European Journal of Pharmacology; 539; 2006: pp. 27-33.

Magnus, et al.: Supporting Online Material for Chemical and Genetic Engineering of Selective Ion Channel-Ligand Interactions; Science; 333; 2011; pp. 1292-1296.

* cited by examiner

FIGURE 1A-C
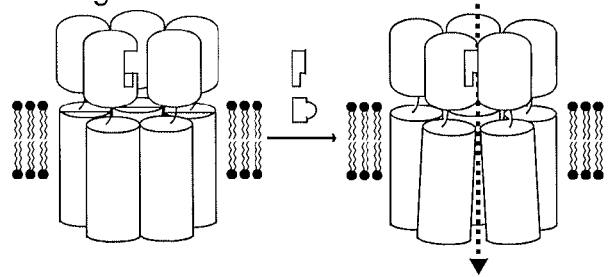
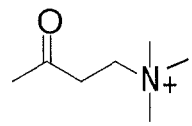
ACh
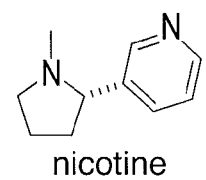
nicotine
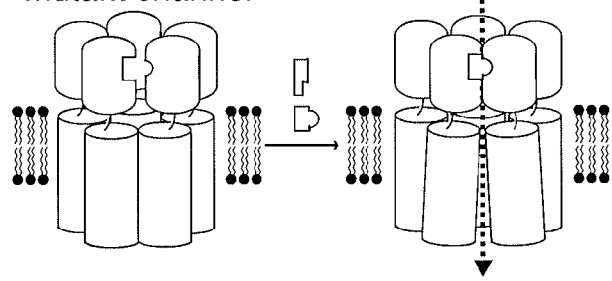
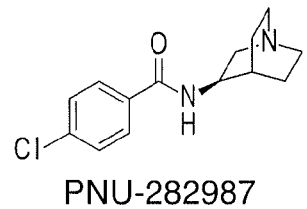
PNU-282987
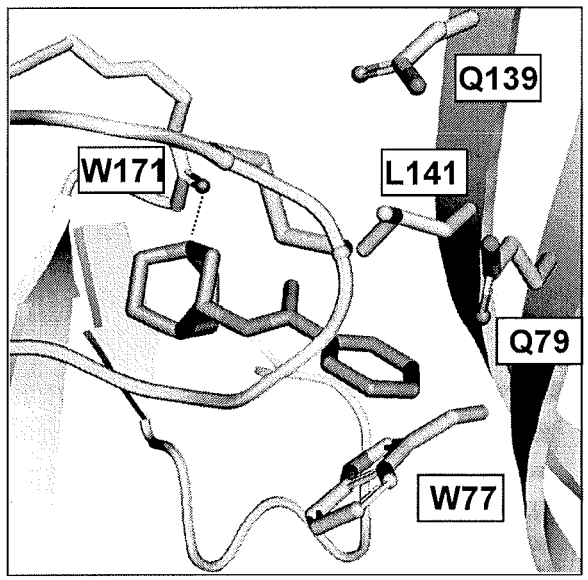

FIGURE 1D-F
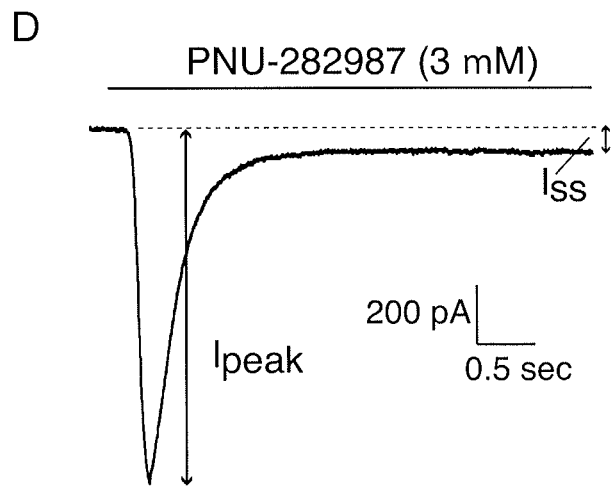
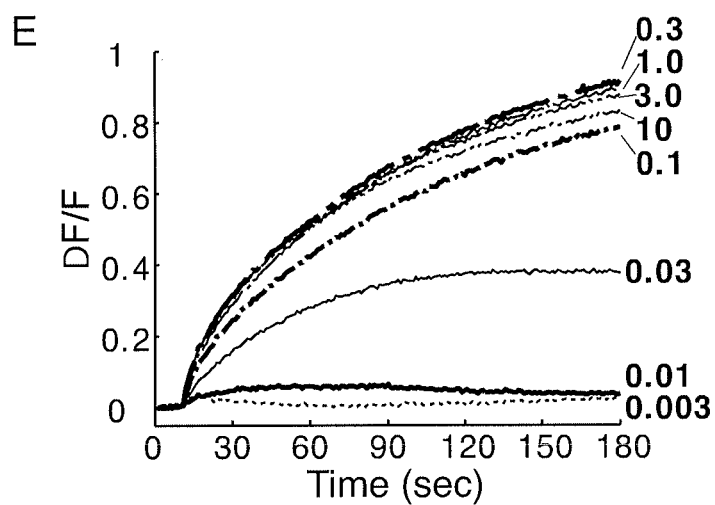
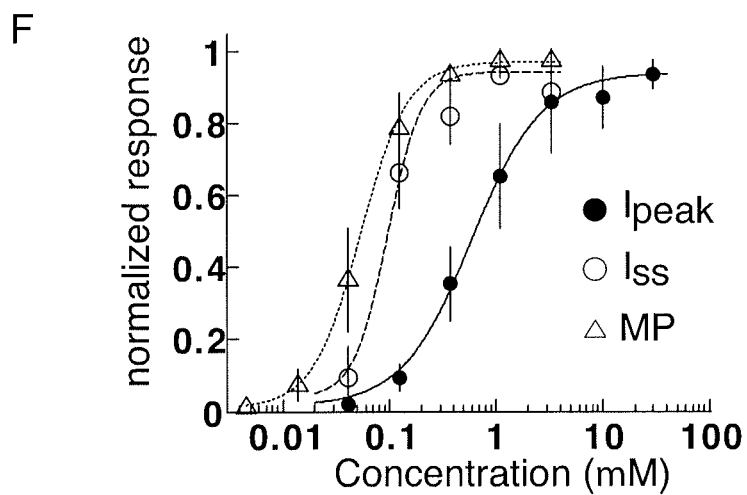

Figure 4
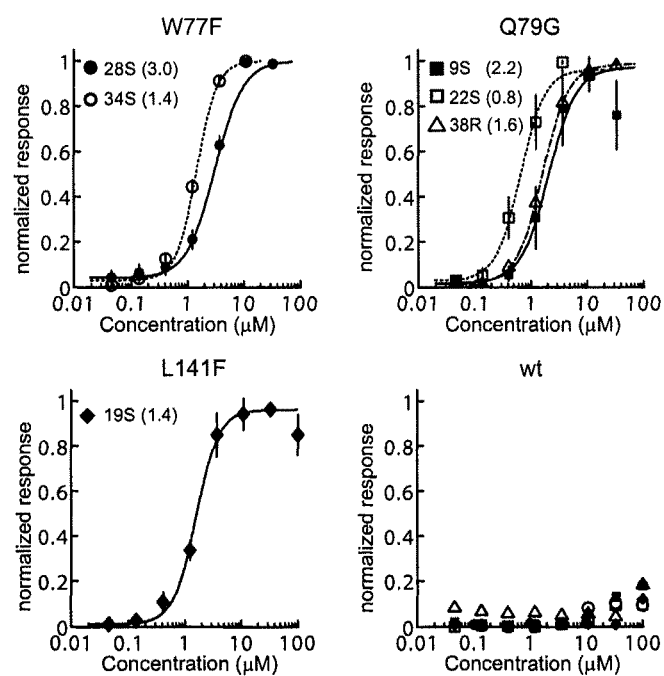
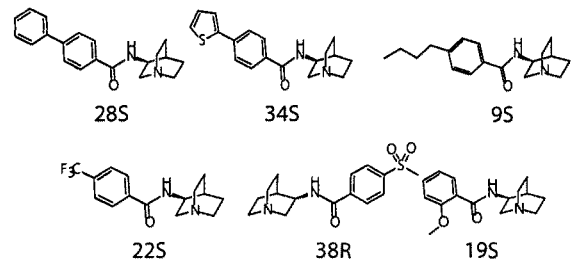

Figure 6
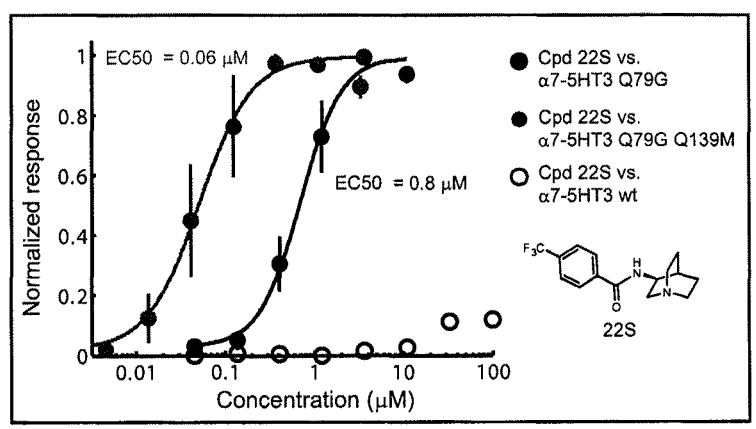
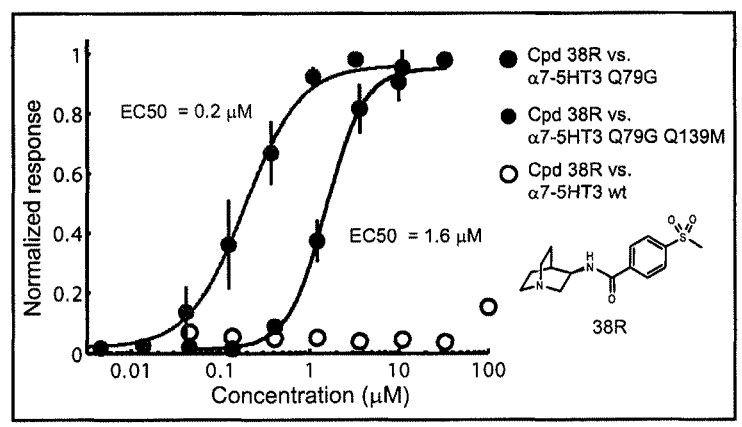

Figure 10

Amino acid sequence of human/mouse α7-5HT3 chimeric receptor

MRCSPGGVWLALAASLLHVSLQGEFQRKLYKELVKNYNPLERPVANDSQPLTV
YFSLSLLQIMDVDEKNQVLTTNIWLQMSWTDHYLQWNVSEYPGVKTVRFPDGQ
IWKPDILLYNSADERFDATFHTNVLVNSSGHCQYLPPGIFKSSCYIDVRWFPFDV
QHCKLKFGSWSYGGWSLDLQMQEADISGYIPNGEWDLVGIPGKRSERFYECCKE
PYPDVTFTVIIRRRPLFYAVSLLLPSIFLMVVDIVGFCLPPDSGERVSFKITLLLGYS
VFLIIVSDTLPATIGTPLIGVYFVVCMALLVISLAETIFIVRLVHKQDLQRPVPDWL
RHLVLDRIAWILCLGEQPMAHRPPATFQANKTDDCSGSDLLPAMGNHCSHVGGP
QDLEKTPRGRGSPLPPPREASLAVRGLLQELSSIRHFLEKRDEMREVARDWLRVG
YVLDRLLFRIYLLAVLAYSITLVTLWSIWHYS (SEQ ID NO: 1)

Figure 11

Amino acid sequence of α7-GlyR chimeric receptor

MRCSPGGVWLALAASLLHVSLQGEFQRKLYKELVKNYNPLERPVANDSQPLTV
YFSLSLLQIMDVDEKNQVLTTNIWLQMSWTDHYLQWNVSEYPGVKTVRFPDGQ
IWKPDILLYNSADERFDATFHTNVLVNSSGHCQYLPPGIFKSSCYIDVRWFPDV
QHCKLKFGSWSYGGWSLDLQMQEADISGYIPNGEWDLVGIPGKRSERFYECCKE
PYPDVTFTVTMRRRMGYYLIQMYIPSLLIVILSWISFWINMDAAPARVGLGITTVL
TMTTQSSGSRASLPKVSYVKAIDIWMAVCLLFVFSALLEYAAVNFVSRQHKELL
RFRRKRRHHKEDEAGEGRFNFSAYGMPACLQAKDGISVKGANNSNTTNPPPAP
SKSPEEMRKLFIQRAKKIDKISRIGFPMAFLIFNMFYWIIYKIVRREDVHNQ
(SEQ ID NO: 6)

Figure 12

Amino acid sequence of α7-GABA C chimeric receptor

MRCSPGGVWLALAASLLHVSLQGEFQRKLYKELVKNYNPLERPVANDSQPLTV
YFSLSLLQIMDVDEKNQVLTTNIWLQMSWTDHYLQWNVSEYPGVKTVRFPDGQ
IWKPDILLYNSADERFDATFHTNVLVNSSGHCQYLPPGIFKSSCYIDVRWFPDV
QHCKLKFGSWSYGGWSLDLQMQEADISGYIPNGEWDLVGIPGKRSERFYECCKE
PYPDVTFTVTMRRRTLYYLLQTYFPATLMVMLSWVSFWIDRRAVPARVPLGITT
VLTMSTIITGVNASMPRVSYIKAVDIYLWVSFVFVFLSVLEYAAVNYLTTVQERK
EQKLREKLPCTSGLPPPRTAMLDGNYSDGEVNDLDNYMPENGEKPDRMMVQLT
LASERSSPQRKSQRSSYVSMRIDTHAIDKYSRIIFPAAYILFNLIYWSIFS
(SEQ ID NO: 10)

CHIMERIC LIGAND-GATED ION CHANNELS AND METHODS OF USE THEREOF

CROSS-REFERENCE TO RELATED APPLICATIONS

This application claims the benefit of U.S. Provisional Application No. 61/136,856, filed Oct. 9, 2008, which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: HOWA_003_01US_SeqList_ST25.txt, date recorded: Oct. 9, 2009, file size 51 kilobytes).

FIELD OF THE INVENTION

The present invention relates to novel chimeric ligand-gated ion channels having alterations in their ligand binding domains that confer pharmacological selectivity for novel small molecule synthetic ligands. Methods of using these novel chimeric ligand-gated ion channels to modulate neuronal activity as well as therapeutic indications for the chimeric receptors are also disclosed.

BACKGROUND OF THE INVENTION

Ligand-gated ion channels (LGICs) transduce chemical signals into electrical activity by increasing the permeability of neurons to specific ions, resulting in current flow, which alters the propensity of neurons to fire action potentials. Action potentials are rapid fluctuations in neuronal voltage that are used for communicating information in the nervous system. Because many neurological disorders are related to neural activity (e.g. pain and epilepsy), ion channels, including LGICs, have been targeted pharmacologically for clinical therapeutics (Brunton et al. (2006) Goodman & Gilman's The Pharmacological Basis of Therapeutics).

Neuronal activity can be enhanced by administering an agonist for a cation-selective (excitatory) LGIC (e.g. glutamate receptor) or neuronal activity can be suppressed or silenced by administering an agonist for an anion-selective (inhibitory) LGIC (e.g. GABA receptor). In order to modulate neuronal activity of a subset of neurons in the nervous system for a therapeutic effect, these small molecule ligands for LGICs would require targeting by injection, iontophoresis, or reverse dialysis to a volume of the neuropil. However, these techniques are invasive, especially for targets deep in the brain. An even greater limitation is that these perturbations within the targeted brain region are not cell type-specific due to the widespread presence of LGICs (e.g. glutamate and GABA ion channels) on nearly all neurons. Perturbation of neurons that are not involved in the therapeutic effect can lead to significant undesired side effects.

Thus, there is a need in the art to develop LGICs that can be selectively activated with tailored compound ligands. Such novel LGICs, once delivered to the neurons of interest by gene therapy methods, would render these neurons sensitive to a ligand selective for such novel LGICs and would obviate the need for local delivery of the ligand, since the tailored ligand would have no effect on native LGICs. Furthermore, selective activation of these novel LGICs would eliminate the non-specific effects arising from activation of neighboring populations of neurons that inevitably occur due to the ubiquitous expression of native LGICs. This would provide specificity for control of neuron activity that could be used therapeutically to treat diseases such as epilepsy and chronic pain. Also, by manipulating activity of neuron populations that control hunger and satiety, these LGICs and associated ligands could also be used to treat diseases associated with undesired behaviors such as overeating or anorexia. Therefore, development of novel LGICs with unique pharmacology would have therapeutic utility.

SUMMARY OF THE INVENTION

The present invention provides novel chimeric receptors that can be selectively activated by compounds. In one embodiment, the chimeric receptor comprises a ligand binding domain from an α7 nicotinic acetylcholine receptor fused to a transmembrane domain from a ligand-gated ion channel protein, wherein the ligand binding domain comprises at least one mutation that confers selective binding to a compound. The transmembrane domain may be from a ligand-gated ion channel from the Cys-loop family of receptors. In some embodiments, the chimeric receptor comprises a transmembrane domain from a cation selective channel, such as the 5HT3 receptor. In other embodiments, the chimeric receptor comprises a transmembrane domain from an anion selective channel, such as the glycine receptor or the GABA C receptor.

The ligand binding domain of the chimeric receptor comprises at least one mutation that confers a unique pharmacology to the chimeric receptor. In some embodiments, the ligand binding domain of the α7 nicotinic acetylcholine receptor contains a point mutation at positions 77, 79, or 141 in SEQ ID NO: 1, SEQ ID NO: 6, or SEQ ID NO: 10. The mutations may include Q79A, Q79G, L141A, L141F, L141P, W77F, W77Y, or W77M substitutions in SEQ ID NO: 1, SEQ ID NO: 6, or SEQ ID NO: 10.

The present invention also includes compounds that preferentially bind and activate the mutated chimeric receptors of the invention. In one embodiment, the compound has the structure of formula I:

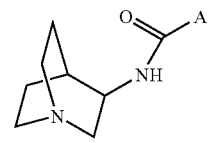

or a pharmaceutically acceptable salt thereof, wherein A, $R_1$, $R_2$, $R_3$, $R_4$ and $R_5$ are as defined below.

In another embodiment, the compound has the core structure of formula II:

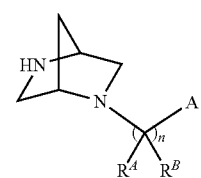

or a pharmaceutically acceptable salt thereof, wherein A, $R^A$, $R^B$ and n are as defined below.

In another embodiment, the compound has the core structure of formula III:

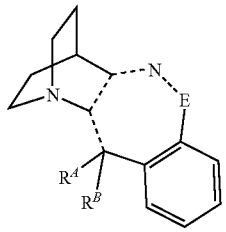

III wherein each _____ is a single or double bond, and $R^A$, $R^B$, $R^C$, $R^D$ and E are as defined below.

The present invention also provides a method of modulating the excitability of a neuronal cell. In one embodiment, the method comprises expressing in the neuronal cell a genetic construct encoding a chimeric receptor, wherein the chimeric receptor comprises a ligand binding domain from an α7 nicotinic acetylcholine receptor fused to a transmembrane domain from a ligand-gated ion channel protein, wherein said ligand binding domain comprises at least one mutation that confers selective binding to a compound of formula I, II or III as described herein; and exposing the neuronal cell to the compound. In another embodiment, the excitability of the neuron is increased. In still another embodiment, the excitability of the neuron is decreased. The neuronal cell may be in vitro or in vivo.

The present invention also encompasses kits comprising chimeric receptors of the invention as disclosed herein and tailored compound ligands. In some embodiments, the chimeric receptor comprises a ligand binding domain from an α7 nicotinic acetylcholine receptor fused to a transmembrane domain from a 5HT3 receptor, wherein said ligand binding domain comprises at least one mutation that confers selective binding to a compound of formula I, II or III as described herein. In other embodiments, the chimeric receptor comprises a ligand binding domain from an α7 nicotinic acetylcholine receptor fused to a transmembrane domain from a glycine receptor or the GABA C receptor, wherein said ligand binding domain comprises at least one mutation that confers selective binding to a compound of formula I, II or III as described herein. At least one mutation may include W77F, Q79A, Q79G, L141F, or L141P substitutions in SEQ ID NO: 1, SEQ ID NO: 6, or SEQ ID NO: 10.

The present invention also provides a method of treating a disease or disorder associated with the nervous system in a subject in need thereof. In one embodiment, the method comprises delivering a genetic construct to a population of neurons in the subject, wherein the genetic construct encodes a mutant α7 nicotinic acetylcholine receptor, wherein the mutation confers selective binding to a compound of formula I, II or III as described herein; and administering the compound to the subject. In some embodiments, the receptor is a chimeric receptor, wherein the chimeric receptor comprises a ligand binding domain from an α7 nicotinic acetylcholine receptor fused to a transmembrane domain from a ligand-gated ion channel protein, wherein said ligand binding domain comprises at least one mutation that confers selective binding to a compound of formula I, II or III as described herein. In some embodiments, the activity of the population of neurons is increased following administration of the compound to the subject. In other embodiments, the activity of the population of neurons is decreased following administration of the compound to the subject. In certain embodiments, the disorder to be treated is epilepsy or chronic pain.

BRIEF DESCRIPTION OF THE DRAWINGS

FIG. 4. Examples of dose responses showing selective interactions between ligands and mutated ligated-gated ion channels. Dose response curves for some compounds with EC50s (shown in parentheses) less than 10 μM against mutant ligand-gated ion channels showing negligible activation of the α7-5HT3 chimeric channel with non-mutated or "wild-type" (wt) sequence.

FIG. 6. Dose response curves for compounds 22S and 38R on the wild-type α7-5HT3 (open circles), single mutant Q79G α7-5HT3 (filled black circles), and double mutant Q79G, Q139M α7-5HT3 (filled red circles) chimeric receptors.

FIG. 10. Amino acid sequence of the wild-type α7-5HT3 chimeric receptor (SEQ ID NO:1).

FIG. 11. Amino acid sequence of the wild-type α7-GlyR chimeric receptor (SEQ ID NO: 6).

FIG. 12. Amino acid sequence of the wild-type α7-GABA C chimeric receptor (SEQ ID NO: 10).

DETAILED DESCRIPTION OF THE INVENTION

Figure 1G:
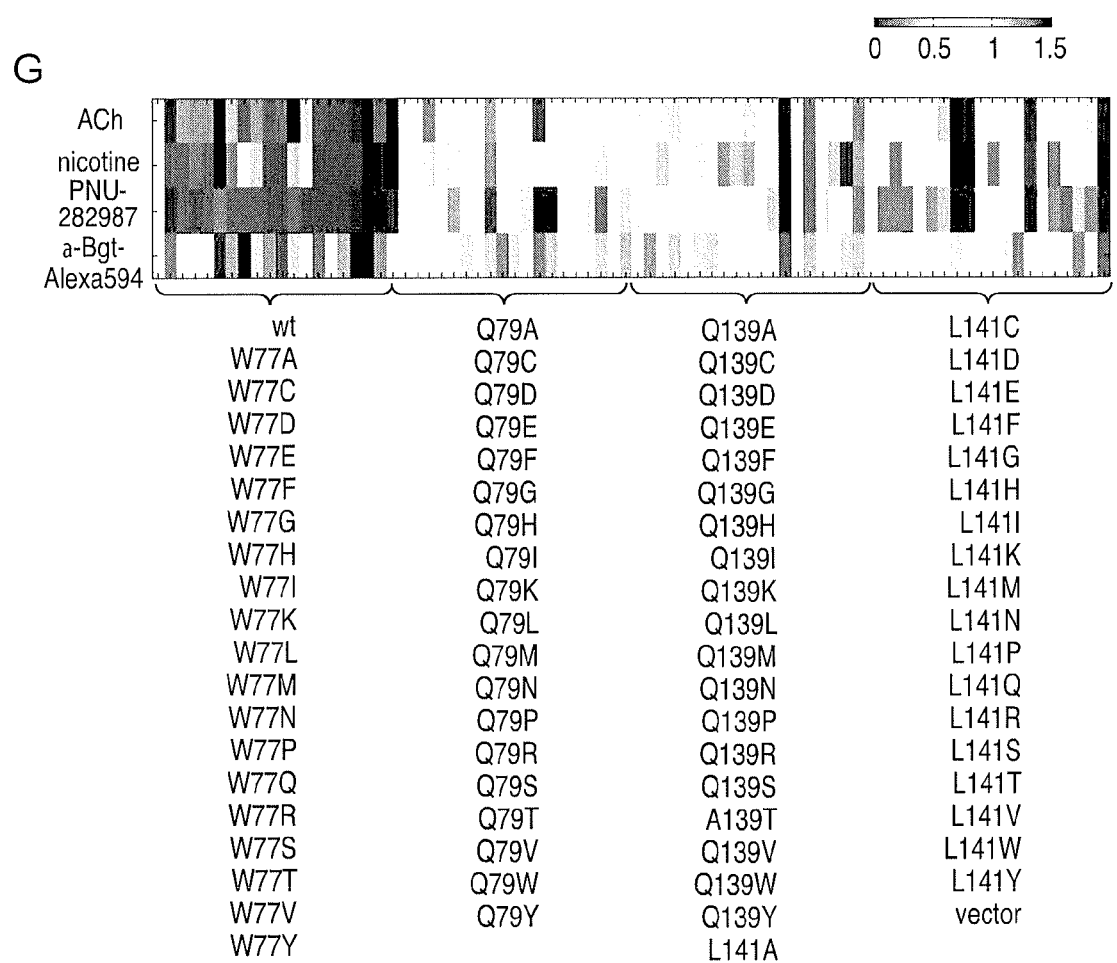
FIG. 1. "Bump-hole" approach to engineering selective ion channel-ligand interactions. A. Design scheme for mutant ion channels that selectively bind a synthetic ligand, wherein the synthetic ligand cannot bind to the natural, endogenous channel. B. Chemical structures of acetylcholine (ACh), nicotine, and PNU-282987. C. Homology model of the human α7 nAChR ligand binding domain (LBD) with docked agonist, PNU-292897, based on the x-ray crystal structure of the snail AChBP showing proximity to the amino acids W77, Q79, Q139, and L141. These residues were targeted for mutagenesis based on their proximity to the benzamide functionality of PNU-282987 in this model. D. Ionic current evoked by PNU-282987 applied to an human embryonic kidney cell expressing the chimeric ion channel α7-5HT3. A large peak current ($I_{peak}$) rapidly decays to a persistent, smaller current ($I_{SS}$). E. Fluoresence change associated with a high throughput membrane potential (MP) assay that was used to screen mutant ion channels against potential ligands. MP response was persistent over several minutes. F. Dose responses show that response from MP assay corresponds to $I_{SS}$. G. Colormap showing the relative activity of α7-5HT3 mutants. Responses to ACh (100 μM), nicotine (100 μM), and PNU-282987 (10 μM) were normalized to the response to ACh (100 μM). The relative amount of cell surface α-Bgt binding sites was measured by normalizing the fluorescent intensity of α-Bgt-594 bound to α7-5HT3 mutants relative to cells expressing α7-5HT3 under non-permeablizing conditions.

Manipulation of electrical activity in neurons provides a powerful approach to regulate physiology and behavior. Effective methods for modulating neuronal activity in vivo should provide: 1) rapid onset of perturbation (seconds to minutes); 2) an ion channel that is non-perturbative to targeted cell types under basal conditions; 3) ligands selective for the ion channel targeted to defined cell types; 4) a straightforward, single transgene genetic strategy without need to interfere with endogenous ion channels, and 5) the capability to independently and orthogonally perturb multiple populations. Several approaches derived from invertebrate (Slimko et al. (2002) J. Neurosci., Vol. 22: 7373-7379) or vertebrate LGICs (Arenkiel et al. (2008) Nature Methods, Vol. 5: 299-302) and G-protein coupled receptors (Armbruster et al. (2007) Proc. Natl. Acad. Sci. USA, Vol. 104: 5163-5168) do not satisfy all of these requirements (Luo et al. (2008) Neuron, Vol. 57: 634-660). A major challenge in overcoming the limitations of these previously developed systems is the paucity of knowledge about the relationship of structure to function in most of the ion channel or receptor systems in use today.

To overcome the limitations of traditional methods of neuronal activation, transgenic and gene therapy strategies can be used to target novel ion channels with unique pharmacology to specific cell populations. Transgenic and gene therapy strategies use cell type-selective promoter activity to target gene expression of the novel ion channels to cell types. The present invention is based, in part, on the discovery that mutations in the ligand binding domain (LBD) of the α7 nicotinic acetylcholine receptor (α7 nAChR) can confer pharmacological specificity such that compound ligands can be tailored to bind uniquely to the mutant receptor. These receptors having unique pharmacology can be used in combination with their tailored compound ligands to modulate the activity of specific neuronal populations.

The nicotinic acetylcholine receptor is probably the best understood member of the Cys-loop family of ligand-gated ion channels (LGICs) after over 30 years of structure-function analysis. In the picture that has emerged, the residues in the binding pocket of the α7 nAChR LBD that contribute to channel activation have been described to involve an aromatic cage consisting of multiple tyrosine and tryptophan residues (Galzi et al. (1991) FEBS Letters, Vol. 294: 198-202). This analysis was confirmed by an x-ray crystal structure of the homologous acetylcholine binding protein (AChBP), which provides a more complete structural rationale for ligand binding (Celie et al. (2004) Neuron, Vol. 41: 907-914). Furthermore, the α7 nAChR LBD can be spliced to the transmembrane domain of the cationic serotonin receptor 3a (α7-5HT3) or the chloride-selective glycine receptor (α7-GlyR1) to generate chimeric receptors (Eisele et al. (1993) Nature, Vol. 366: 479-483; Grutter et al. (2005) Proc. Natl. Acad. Sci. USA, Vol. 102: 18207-18212). This transferability of the pharmacologic element (e.g., LBD) to multiple ion conducting elements (channel or transmembrane domains) is a useful foundation for optimizing function so that channels have the preferred properties. The major challenge in using ion channels with native ligand binding domains and their corresponding ligands as tools to manipulate neuronal activity is that these native ligand binding domains are already found in the brain, and thus the small molecule ligands will perturb electrical activity in multiple undesired cell populations.

To overcome these issues, the present invention describes an approach to modify the ligand recognition properties of the nAChR using a "bump-hole" strategy (FIG. 1A). These modified ligand binding domains (LBDs) of the α7 nAChR are modular units that can be combined with channel domains (e.g. transmembrane domains) to generate chimeric receptors with desired ligand selectivity and conductance properties. Accordingly, the present invention provides chimeric receptors comprising a ligand binding domain from an α7 nicotinic acetylcholine receptor fused to a transmembrane domain from a ligand-gated ion channel protein, wherein the ligand binding domain comprises at least one mutation that confers selective binding to a compound. A "chimeric receptor" refers to a receptor comprising at least one domain from a first protein and at least one domain from a second protein. The first and second proteins may be from the same species (i.e.

both human proteins) or may be from different species (i.e. one human protein and one mouse protein).

As used herein, the term "ligand binding domain" refers to the extracellular region of a protein receptor that interacts with a compound such that a conformational change of the region occurs upon binding of the compound. The conformational change of the ligand binding domain typically produces activation of the receptor. In the case of ligand-gated ion channels, binding of the ligand to the ligand binding domain opens the ion channel. As used herein, the term "transmembrane domain" is used interchangeably with "channel domain" or "ion pore domain" (IPD) and refers to the region of the protein receptor that spans the lipid membrane of the cell and forms the channel or pore in the membrane through which ions can pass between the extracellular milieu and the cellular cytoplasm. The ligand binding domain of the α7 nAChR is functionally fused to a channel or transmembrane domain from a ligand-gated ion channel. "Functionally fused" means that the two protein domains are linked such that binding of a ligand to the ligand binding domain will result in a conformational change that opens the ion channel (i.e. increases channel conductance).

In one embodiment, the transmembrane domain is from a ligand-gated ion channel of the Cys-loop family of ionotropic receptors. Examples of ligand-gated ion channels from this family include, but are not limited to, ionotropic nicotinic acetylcholine receptors, ionotropic serotonin receptors (e.g. 5HT3), ionotropic glycine receptors, and ionotropic GABA receptors (e.g. $GABA_A$ and $GABA_C$ receptors). In some embodiments, the ligand-gated ion channels are selective for cations, such as the 5HT3 and nicotinic acetylcholine receptors. In other embodiments, the ligand-gated ion channels are selective for anions, such as the GABA and glycine receptors. In preferred embodiments, the transmembrane domain of the chimeric receptor is the transmembrane domain of a 5HT3, nAChR, glycine, or GABA C receptor.

Figure 3:
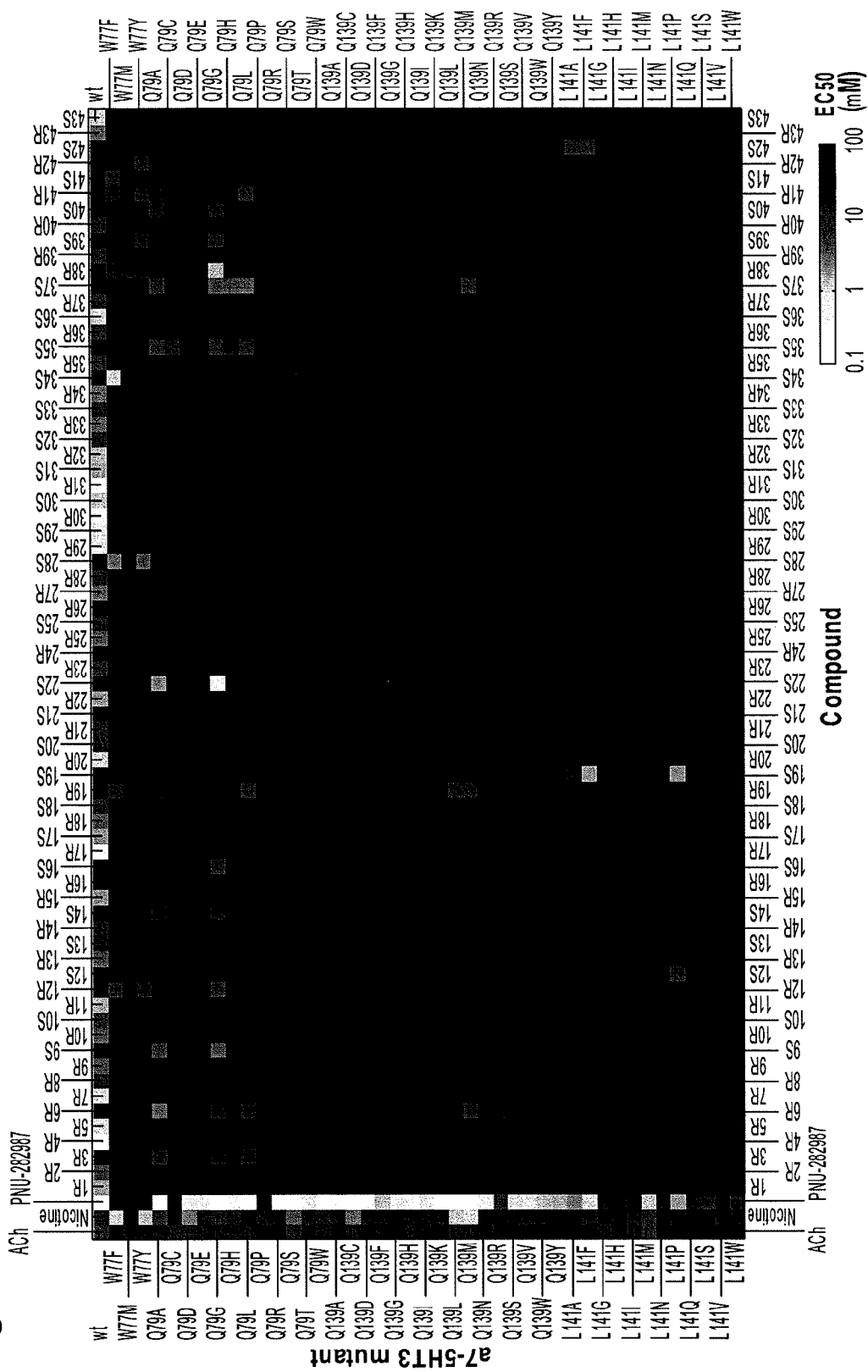
FIG. 3. Colormap of EC50s from dose response curves of α7-5HT3 variants vs. ACh, nicotine, and aminoquinuclidine benzamides. In order to highlight molecules that are highly selective for α7-5HT3 mutant chimeric receptors vs. the α7-5HT3 wild-type chimeric receptor, the data has been sorted such that EC50 values for molecules with EC50<30 μM for the wild-type α7-5HT3 chimeric receptor (top row) are not shown for α7-5HT3 mutant chimeric receptors.

In another embodiment of the invention, there is at least one mutation in the ligand binding domain of the α7 nAChR that confers selective binding to a compound (e.g., selectivity-inducing mutation). The mutation can include a point mutation in the amino acid residue in position 77, 79, 139, or 141 in the amino acid sequence listed in SEQ ID NO: 1, SEQ ID NO: 6, or SEQ ID NO: 10. Non-limiting examples of the point mutations include Q79A, Q79G, L141A, L141F, L141P, W77F, W77Y, and W77M, where the identity of the amino acids is designated by the single letter amino acid code. Other suitable amino acid point mutations that also confer selectivity are shown in FIG. 3 and include Q79C, Q79D, Q79E, Q79H, Q79L, Q79P, Q79R, Q79S, Q79T, Q79W, Q139A, Q139C, Q139D, Q139F, Q139G, Q139H, Q139I, Q139K, Q139L, Q139M, Q139N, Q139R, Q139S, Q139V, Q139W, Q139Y, L141G, L141H, L141I, L141M, L141N, L141Q, L141S, L141V, and L141W. In a preferred embodiment, the at least one mutation in the ligand binding domain is W77F in SEQ ID NO: 1, SEQ ID NO: 6, or SEQ ID NO: 10. In another preferred embodiment, the at least one mutation in the ligand binding domain is Q79A or Q79G in SEQ ID NO: 1, SEQ ID NO: 6, or SEQ ID NO: 10. In still another preferred embodiment, the at least one mutation in the ligand binding domain is L141F or L141P in SEQ ID NO: 1, SEQ ID NO: 6, or SEQ ID NO: 10. In some embodiments, the chimeric receptor has the amino acid sequence of SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 11, SEQ ID NO: 12, or SEQ ID NO: 13. The ligand binding domain of the chimeric receptor may have more than one mutation in the amino acid sequence. By way of example, the ligand binding domain of the α7 nAChR may comprise a point mutation at position 79 and 141 of the amino acid sequence or at position 79 and 139 of the amino acid sequence. Any of the specific mutations disclosed above as well as additional mutations may be made in combination to generate double, triple, or multiple mutant chimeric receptors.

The receptors of the invention can also contain mutations in the ligand binding domain of the α7 nAChR that significantly reduces responsiveness to the naturally occurring ligand, acetylcholine. Because acetylcholine is produced in the brain, mutations that limit the sensitivity of chimeric channels to ACh reduce the possibility of the channel being activated in the absence of the synthetic ligand. Suitable point mutations that reduce binding to acetylcholine include Y115F, Q79R, Q139G, Q139V, Q139W, Q139Y, L141A, L141Q, L141S, with Y115F, Q139G, L141A, and L141S being preferred in some embodiments. These mutations can be combined with any of the selectivity-inducing mutations as described herein, such as Q79G and L141F.

In some embodiments, the receptors of the invention also have mutations in the transmembrane domain, specifically the M2 region and regions flanking the M2 region of Cys-loop ion channels, which affect conductance and desensitization properties.

In other embodiments, in addition to the selectivity-inducing mutations described herein, the receptors of the invention have mutations in the cytoplasmic domains, specifically in the M3-M4 loop, which affect ion conductance properties. For instance, for chimeric receptors containing the 5HT3 transmembrane domain, deletion of portions of the M3-M4 loop, replacement with sequences from other Cys-loop receptors, or specific mutations such as the triple mutation: R425Q R429D R433A modulate the conductance of the ion channel. In one embodiment, in addition to at least one selectivity-inducing mutation, the chimeric receptor contains the triple mutation R425Q R429D R433A in SEQ ID NO: 1, which increases conductance in α7-5HT3 chimeric receptors (referred to as high conductance or HC).

The present invention also encompasses nucleic acids encoding the mutant chimeric receptors of the invention. In some embodiments, the nucleic acids encode a mutant chimeric receptor having an amino acid sequence of SEQ ID NO: 2, SEQ ID NO: 3, SEQ ID NO: 4, SEQ ID NO: 5, SEQ ID NO: 7, SEQ ID NO: 8, SEQ ID NO: 9, SEQ ID NO: 11, SEQ ID NO: 12, or SEQ ID NO: 13. In one embodiment, the nucleic acid encodes a chimeric receptor comprising the ligand binding domain of the α7-nAChR and an ion pore domain from the GABA C (SEQ ID NO: 10). The nucleic acids encoding the chimeric receptors may be operably linked to a promoter and incorporated into a genetic construct or vector. The promoter may be an inducible promoter and/or a tissue specific promoter. For example, neuron-specific promoters such as synapsin, CAMKII, and neuron-specific enolase can be used to target neurons selectively over interspersed cell classes such as glia and epithelia cells. TRPV1 promoter can be used to target nociceptive sensory neurons which give rise to the pain transmitting C-fibers. In addition, POMC, NPY, AGRP, MCH, and Orexin promoters can be used to target neurons involved in obesity or anorexia. Other suitable promoters can be ascertained by one of skill in the art depending on the particular population of cells to be targeted. The nucleic acid encoding the chimeric receptor may be incorporated into the genome of a cell or it may be contained within a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In some embodiments, the nucleic acid encoding the chimeric receptor is contained within a plasmid or viral vector.

General texts which describe molecular biological techniques, which are applicable to the present invention, such as cloning, mutation, and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the production of the novel chimeric receptors of the invention. Methods of protein engineering and recombinant DNA technology are known to those of skill in the art and can be employed to produce the chimeric receptors of the invention given the guidance described herein.

The present invention also includes a method of modulating the excitability of a neuronal cell. "Excitability" refers to the ability of neurons to generate and propagate action potentials. Increased excitability results in a lower threshold for action potential generation (i.e. less current is required to trigger an action potential), while decreased excitability increases the threshold for action potential generation (i.e. more current is required to trigger an action potential). In one embodiment, the method comprises expressing in the neuronal cell a genetic construct encoding a chimeric receptor, wherein the chimeric receptor comprises a ligand binding domain from an α7 nicotinic acetylcholine receptor fused to a transmembrane domain from a ligand-gated ion channel protein, wherein said ligand binding domain comprises at least one mutation that confers selective binding to a compound; and exposing the neuronal cell to the compound. The neuronal cell may be in vitro or in vivo.

Any of the novel chimeric receptors described herein may be used in methods of modulating neuronal excitability. In one embodiment, the chimeric receptor comprises a transmembrane domain from a ligand-gated ion channel protein that is selective for cations. In a preferred embodiment, the transmembrane domain is a transmembrane domain from the 5HT3 receptor (α7-5HT3). Activation of these "cationic" types of chimeric receptors with their compound ligands can increase the excitability of neuronal cells expressing such chimeric receptors.

In another embodiment, the chimeric receptor comprises a transmembrane domain from a ligand-gated ion channel protein that is selective for anions. In a preferred embodiment, the transmembrane domain is a transmembrane domain from the glycine receptor (α7-GlyR1). In a another preferred embodiment, the transmembrane domain is a transmembrane domain from the GABA C receptor (α7-GABA C). Activation of these "anionic" types of chimeric receptors with their compound ligands can decrease the excitability of neuronal cells expressing such chimeric receptors.

The chimeric receptors comprise a ligand binding domain from the α7 nicotinic acetylcholine receptor that has at least one mutation that confers selective binding to a compound described herein. In some embodiments, the at least one mutation is selected from the group consisting of Q79A, Q79G, L141A, L141F, L141P, W77F, W77Y, and W77M in SEQ ID NO: 1. In other embodiments, the at least one mutation is selected from the group consisting of Q79A, Q79G, L141A, L141F, L141P, W77F, W77Y, and W77M in SEQ ID NO: 6. In certain embodiments, the at least one mutation is selected from the group consisting of Q79A, Q79G, L141A, L141F, L141P, W77F, W77Y, and W77M in SEQ ID NO: 10. Preferably, the compound does not activate a wild-type α7 nicotinic acetylcholine receptor.

The compounds described herein can be used in conjunction with the novel chimeric receptors in: (a) the methods of modulating neuronal excitability as described herein; (b) the kits of the present invention as described herein; and (c) the methods for treating a disease or disorder of the nervous system as described herein. In one embodiment, the compound is selected from the group consisting of Compound Nos. 3R, 6R, 9S, 12R, 12S, 14S, 16S, 19R, 19S, 21S, 22S, 28S, 34S, 35S, 37S, 38R, 39S, 40S, 41R, 41S, 42R, 42S, 85S, 86S, 88S, 89S, 90S, 91S, 96R, 97R, 115S, 117S, 118S, 119S, 120S, 121S, 127S, 131S, 132S, 134S, 148S, 149S, 154S, 156S, 157S, 158S, 163S, 164S, 165S, 170R, 208S, 212, 241, 242, 245, 253, 254, 255, 278S, 279S, 281S, 292R, 294S, 295S, and 296S.

In some embodiments, a particular chimeric receptor may be used with one or more particular compounds. Non-limiting examples of some of these combinations include: (1) a W77F α7-5HT3 (SEQ ID NO: 2), W77F α7-GlyR1 (SEQ ID NO: 7), or W77F α7-GABA C (SEQ ID NO: 11) chimeric receptor with the 28S, 34S, 96R, 97R, 131S, 132S, 278S, 279S, or 281S synthetic compound; (2) Q79A α7-5HT3, Q79G α7-5HT3 (SEQ ID NO: 3), Q79A α7-GlyR1, Q79G α7-GlyR1 (SEQ ID NO: 8), Q79A α7-GABA C, or Q79G α7-GABA C (SEQ ID NO: 12) chimeric receptor with the 9S, 16S, 22S, 38R, 115S, 117S, 134S, 148S, 149S, 154S, 156S, 157S, 158S, 163S, 164S, 165S, 170R, 292R, 295S, or 296S synthetic compound; and (3) L141F α7-5HT3 (SEQ ID NO: 4), L141P α7-5HT3, L141F α7-GlyR1 (SEQ ID NO: 9), or L141P α7-GlyR1, L141F α7-GABA C (SEQ ID NO: 13), or L141P α7-GABA C chimeric receptor with any one of Compound Nos. 19S, 85S, 86S, 88S, 89S, 90S, 91S, 118S, 119S, 120S, 121S, 127S, 208S, 212, 241, 242, 245, 253, 254, 255, or 2945.

Efficacy of a synthetic ligand in activating a particular mutant chimeric receptor can be measured by one of several assays including, but not limited to, a fluorescence membrane potential assay, radioactive binding assays, and voltage clamp measurement of peak currents and sustained currents (see, e.g., Examples 2 and 4). For instance, changes in ion flux may be assessed by determining changes in electrical potential of the cell or membrane expressing a novel chimeric receptor of the invention upon exposure to a particular synthetic compound. Changes in current and membrane potential can be measured with voltage-clamp and patch-clamp techniques as known in the art. Other known assays include radiolabeled ion flux assays and fluorescence assays using voltage-sensitive dyes (see, e.g., Vestergarrd-Bogind et al., J. Membrane Biol., 88: 67-75 (1988); Gonzales & Tsien, Chem. Biol., 4: 269-277 (1997); Daniel et al., J. Pharmacol. Meth., 25: 185-193 (1991); Holevinsky et al., J. Membrane Biology, 137: 59-70 (1994)). Thus, the invention encompasses synthetic ligands that exhibit an EC50>70 µM, 75 µM, 80 µM, 85 µM, 90 µM, 95 µM, or >100 µM against the wild-type α7 nAChR and an EC50<15 µM, 12 µM, 10 µM, 8 µM, 6 µM, 5 µM, 4 µM, 2 µM, or <1 µM against a mutant α7 receptor as measured by any of the above-described assays (e.g., fluorescence membrane potential assay or peak/sustained current assay). An "EC50" or "half maximal effective concentration" as used herein is the concentration at which the synthetic ligand produces a half-maximal response. Synthetic ligands that produce >40%, 45%, 50%, 55%, 60%, 65%, 70%, or >75% maximal response on mutant receptors in a HEK cell membrane potential assay (see Example 2) relative to the agonist response on a wild-type receptor to a full agonist such as acetylcholine are also included in the invention.

There are a number of methods known in the art for introducing the genetic construct encoding the novel chimeric receptors of the invention in the cells of interest (e.g., neuronal cells). For example, the vector or genetic construct can be transferred into a host cell by physical, chemical or biological means. Physical methods for introducing a polynucleotide into a host cell include calcium phosphate precipitation, DEAE-dextran, lipofection, particle bombardment, microinjection, electroporation, cell sonication, receptor-mediated transfection, and the like.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, vaccinia virus, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; and WO 03/093449, which are herein incorporated by reference in their entireties.

The present invention also provides compounds. These compounds specifically bind to at least one of the mutant ligand binding domains of the α7 nAChR as described herein. In one embodiment, the compound has the structure of formula I:

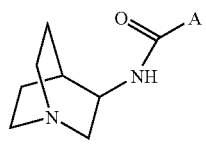

I or a pharmaceutically acceptable salt thereof, wherein A is one of:

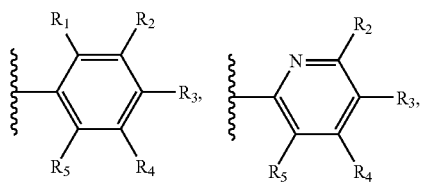

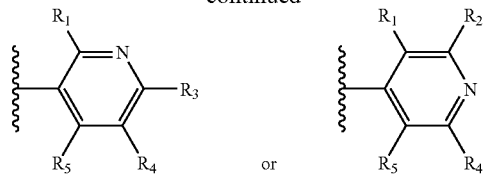

wherein, each of $R_1$, $R_4$ and $R_5$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

each of $R_2$ and $R_3$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

or $R_2$ and $R_3$, together with the carbon atoms to which they are attached, form a 5 or 6-membered carbocyclic or heterocyclic ring optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl;

with the provisos that: (a) at least one of $R_1$, $R_2$, $R_3$, $R_4$ and $R_5$ is not hydrogen; and (b) if neither of $R_1$ and $R_5$ is $C_1$-$C_6$ alkoxy, then $R_3$ is present and is not hydrogen.

In certain embodiments of the compound of formula I, A is

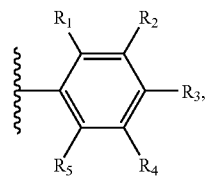

wherein $R_3$ is phenyl optionally substituted with halo, $C_1$-$C_6$ alkyl, $C_1$-$C_6$ alkoxy or $C_1$-$C_6$ haloalkyl. In one such embodiment, each of $R_1$, $R_2$, $R_4$ and $R_5$ is hydrogen.

In certain other embodiments of the compound of formula I, A is

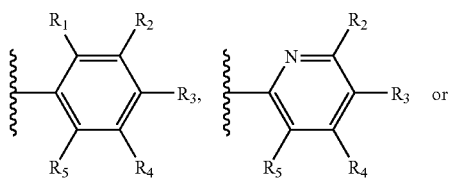

-continued

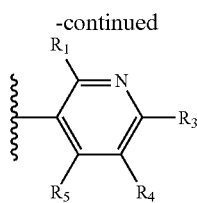

wherein $R_3$ is $C_3$-$C_6$ alkyl, $C_5$-$C_6$ alkoxy, $C_1$-$C_2$ haloalkoxy, $C_1$-$C_2$ thiohaloalkyl, $C_1$-$C_2$ perhaloalkyl, dialkylamino or alkylsulfonyl. In one such embodiment, A is

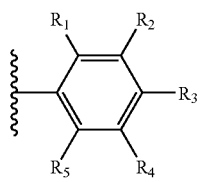

wherein each of $R_1$, $R_2$, $R_4$ and $R_5$ is hydrogen. In another such embodiment A is

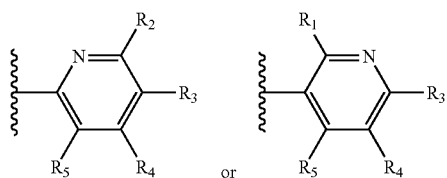

wherein $R_3$ is $C_1$-$C_2$ perhaloalkyl or $C_3$-$C_6$ alkyl. In one such embodiment each of $R_4$ and $R_5$ is hydrogen; $R_1$, if present, is hydrogen; and $R_2$, if present, is hydrogen.

In one embodiment of the compound of formula I, at least one of $R_1$ and $R_5$ is methoxy, ethoxy or phenoxy. In one such embodiment, A is

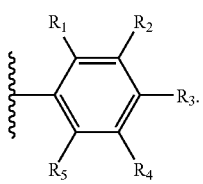

wherein $R_1$ is methoxy, ethoxy or phenoxy; each of $R_2$, $R_3$ and $R_4$ is independently hydrogen, chloro, fluoro, methoxy, ethoxy, methyl or ethyl; and $R_5$ is hydrogen.

In another embodiment, the compound has the structure of formula II:

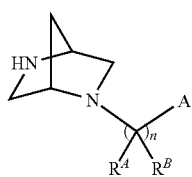

or a pharmaceutically acceptable salt thereof, wherein:
A is aryl or heteroaryl optionally substituted with halo, $C_1$-$C_6$ alkyl, $C_1$-$C_6$ alkoxy, $C_1$-$C_6$ thioalkyl, $C_1$-$C_6$ haloalkyl, furanyl or thiophenyl, wherein said furanyl and thiophenyl are optionally substituted with halo, $C_1$-$C_6$ alkyl, $C_1$-$C_6$ alkoxy, $C_1$-$C_6$ thioalkyl or $C_1$-$C_6$ haloalkyl;

each of $R^A$ and $R^B$ is hydrogen or $C_1$-$C_6$ alkyl;

or $R^A$ and $R^B$ taken together are =O; and n is 0 or 1.

In another embodiment, the compound has the structure of formula III:

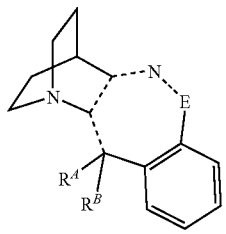

wherein each _____ is a single or double bond;

each $R^A$ and $R^B$ is hydrogen or $R^A$ and $R^B$ taken together are =O;

E is —N, —NH, $CR^C$, or $CR^C R^D$, each $R^C$ and $R^D$ is hydrogen or $R^C$ and $R^D$ taken together are =O;

or a pharmaceutically acceptable salt thereof;

wherein said compound does not comprise adjacent double bonds.

In one such embodiment, the compound of formula III is a member selected from the group of:

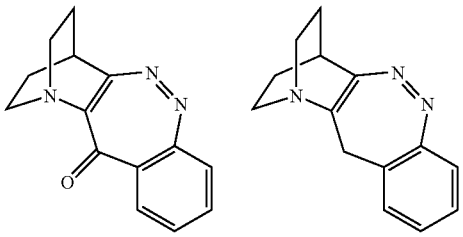

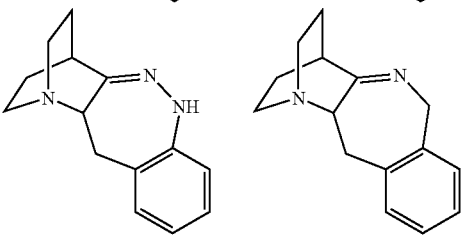

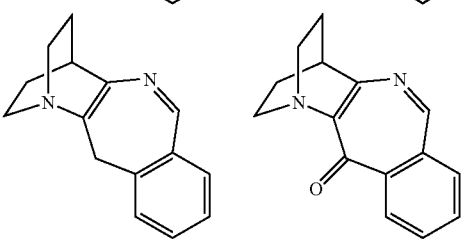

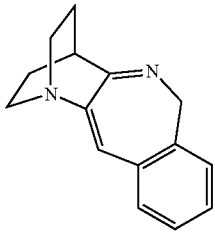 and 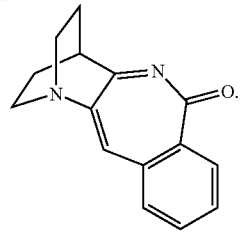

In one such embodiment, the compound of formula III is the compound having the structure:

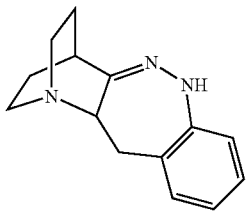 [SMILES: c1ccc2c(c1)CC1C(=NN2)C2CCN1CC2]

or a pharmaceutically acceptable salt thereof.

The compounds of formula I, II and III contain a chiral carbon atom, and may be in the form of a mixture of the R enantiomer and the S enantiomer (e.g., a racemic mixture) or as substantially pure R or S enantiomer. In certain embodiments of compounds of formula I, II and III, the S enantiomer is preferred. For example, in certain embodiments the S enantiomer exhibits greater selectivity than does the R enantiomer for a particular mutated chimeric receptor of the invention than for the corresponding wild type chimeric receptor.

As described above, the present invention provides a method of treating a disease or disorder associated with the nervous system in a subject in need thereof. In one embodiment, the method comprises delivering a genetic construct to a population of neurons in the subject, wherein the genetic construct encodes a mutant α7 nicotinic acetylcholine receptor, wherein the mutation confers selective binding to a compound of formula I, II or III as described above; and administering the compound to the subject. The present invention also provides a method of modulating the excitability of a neuronal cell. In one embodiment, the method comprises expressing in the neuronal cell a genetic construct encoding a chimeric receptor, wherein the chimeric receptor comprises a ligand binding domain from an α7 nicotinic acetylcholine receptor fused to a transmembrane domain from a ligand-gated ion channel protein, wherein said ligand binding domain comprises at least one mutation that confers selective binding to a compound of formula I, II or III as described above; and exposing the neuronal cell to the compound. In addition, the present invention provides kits comprising chimeric receptors of the invention as disclosed herein and a compound of formula I, II or III as described above.

In one such embodiment, the compound is represented by formula I, wherein A is

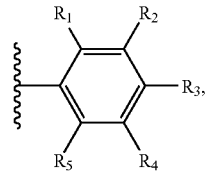

wherein $R_3$ is phenyl optionally substituted with halo, $C_1$-$C_6$ alkyl, $C_1$-$C_6$ alkoxy or $C_1$-$C_6$ haloalkyl, each of $R_1$, $R_2$, $R_4$ and $R_5$ is hydrogen, and at least one mutation in the ligand binding domain of the mutant α7 nicotinic acetylcholine receptor is W77F in SEQ ID NO: 1, SEQ ID NO: 6 or SEQ ID NO: 10. For example, in one such embodiment, the mutated chimeric receptor has the sequence of SEQ ID NO: 2, SEQ ID NO: 7 or SEQ ID NO: 11.

In another such embodiment, the compound is represented by formula I, wherein A is

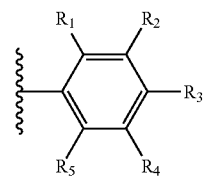

wherein $R_3$ is $C_3$-$C_6$ alkyl, $C_5$-$C_6$ alkoxy, $C_1$-$C_2$ haloalkoxy, $C_1$-$C_2$ thiohaloalkyl, $C_1$-$C_2$ perhaloalkyl, dialkylamino or alkylsulfonyl, each of $R_1$, $R_2$, $R_4$ and $R_5$ is hydrogen, and at least one mutation in the ligand binding domain of the mutant α7 nicotinic acetylcholine receptor is Q79G or Q79A in SEQ ID NO: 1, SEQ ID NO: 6 or SEQ ID NO: 10. For example, in one such embodiment, the mutated chimeric receptor has the sequence of SEQ ID NO: 3, SEQ ID NO: 8 or SEQ ID NO: 12.

In yet another such embodiment, the compound is represented by formula I, wherein A is

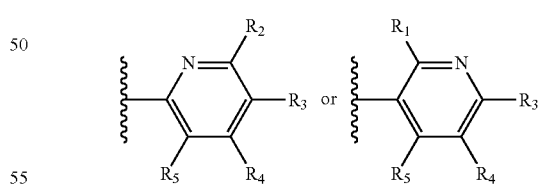

wherein $R_3$ is $C_1$-$C_2$ perhaloalkyl or $C_3$-$C_6$ alkyl, each of $R_4$ and $R_5$ is hydrogen, $R_1$, if present, is hydrogen, $R_2$, if present, is hydrogen, and at least one mutation in the ligand binding domain of the mutant α7 nicotinic acetylcholine receptor is Q79G or Q79A in SEQ ID NO: 1, SEQ ID NO: 6 or SEQ ID NO: 10. For example, in one such embodiment, the mutated chimeric receptor has the sequence of SEQ ID NO: 3, SEQ ID NO: 8 or SEQ ID NO: 12.

In another such embodiment, the compound is represented by formula I, wherein A is one of:

wherein at least one of $R_1$ and $R_5$ is methoxy, ethoxy or phenoxy, and at least one mutation in the ligand binding domain of the mutant α7 nicotinic acetylcholine receptor is L141F or L141P in SEQ ID NO: 1, SEQ ID NO: 6 or SEQ ID NO: 10. For example, in one such embodiment, the mutated chimeric receptor has the sequence of SEQ ID NO: 4, SEQ ID NO: 9 or SEQ ID NO: 13.

In one such embodiment, A is $R_1$ is methoxy, ethoxy or phenoxy, each of $R_2$, $R_3$ and $R_4$ is independently hydrogen, chloro, fluoro, methoxy, ethoxy, methyl or ethyl, and $R_5$ is hydrogen.

In another such embodiment, the compound is represented by formula II, wherein A is phenyl, pyridyl, pyrazinyl or quinoxalinyl, substituted with halo, $C_1$-$C_6$ alkyl, $C_1$-$C_6$ alkoxy, $C_1$-$C_6$ thioalkyl or $C_1$-$C_6$ haloalkyl, and at least one mutation in the ligand binding domain of the mutant α7 nicotinic acetylcholine receptor is L141F or L141P in SEQ ID NO: 1, SEQ ID NO: 6 or SEQ ID NO: 10. For example, in one such embodiment, the mutated chimeric receptor has the sequence of SEQ ID NO: 4, SEQ ID NO: 9 or SEQ ID NO: 13.

In yet another embodiment, the compound is represented by formula III, and at least one mutation in the ligand binding domain of the mutant α7 nicotinic acetylcholine receptor is L141F or L141P in SEQ ID NO: 1, SEQ ID NO: 6 or SEQ ID NO: 10. For example, in one such embodiment, the mutated chimeric receptor has the sequence of SEQ ID NO: 4, SEQ ID NO: 9 or SEQ ID NO: 13. In one such embodiment, the compound is Compound No. 212 as described herein.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or OMe), ethoxy (—$OCH_2CH_3$ or —OEt), t-butoxy (—O—$C(CH_3)_3$ or —OtBu) and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like. "Aryloxy" means a group having the formula —O-aryl, in which an aryl group, as defined above, is attached to the parent molecule via an oxygen atom.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms. "Heteroalkoxy" means a group having the formula —O-heteroalkyl, in which a heteroalkyl group, as defined above, is attached to the parent molecule via an oxygen atom.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs* (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

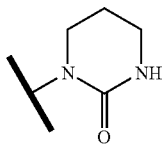

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

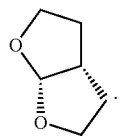

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heteroaryl" refers to a monovalent aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc. "Heteroaryloxy" means a group having the formula —O-heteroaryl, in which a heteroaryl group, as defined above, is attached to the parent molecule via an oxygen atom.

An "acyl group" or "alkanoyl" is a functional group having the basic formula RC(=O) with a double bond between the carbon and oxygen atoms (i.e. a carbonyl group), and a single bond between R and the carbon. An "O-acyl group" is an acyl group as defined above linked to the parent molecule via an oxygen atom.

A "halogen" or halide is a fluorine, chlorine, bromine, iodine, or astatine atom.

In some embodiments, the compound has the structure in formula I, wherein $R_2$ is a hydrogen and $R_4$ is a hydrogen. In other embodiments, the compound has the structure in formula I, wherein $R_1$ is a methoxy, ethoxy, or phenoxy group, $R_2$ is a hydrogen and $R_4$ is a hydrogen. In still other embodiments, the compound has the structure in formula I, wherein $R_1$ is a methoxy, ethoxy, or phenoxy group, $R_2$ is a hydrogen, $R_3$ is a hydrogen, methyl, methoxy, or chloride group, and $R_4$ is a hydrogen. In one embodiment, the compound has the structure in formula I, wherein $R_1$ is a methoxy group, $R_2$ is a hydrogen, $R_3$ is a hydrogen, and $R_4$ is a methoxy group. In certain embodiments, the compound is 85S, 86S, 87S, 88S, 89S, 90S or 91S.

The present invention encompasses the use of pharmaceutical compositions of the appropriate vector encoding the chimeric receptors as well as pharmaceutical compositions of the synthetic ligands to practice the methods of the invention. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Compositions of the present invention comprise an effective amount of active ingredient (the genetic construct or synthetic ligand), dissolved or dispersed in a pharmaceutically acceptable carrier or aqueous medium. The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the active ingredient (genetic constructs or synthetic ligands) of the compositions.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The active compositions of the present invention may include classic pharmaceutical preparations. Administration of these compositions according to the present invention may be via any common route so long as the target tissue (e.g., neuronal population) is available via that route. This includes oral, nasal, or buccal. Alternatively, administration may be by intradermal, subcutaneous, intramuscular, intrathecal, intracerebral, intraperitoneal or intravenous injection. Such compositions would normally be administered as pharmaceutically acceptable compositions, as described above.

By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Salts formed with free carboxyl groups of the compound can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intrathecal, intracerebral, and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated and the particular active ingredient (e.g., synthetic ligand or genetic construct) used. The person responsible for administration will, in any event, determine the appropriate dose for the individual subject.

The present invention also encompasses a kit comprising a chimeric receptor of the invention as disclosed herein and at least one compound ligand. The kit may include a genetic construct that encodes the chimeric receptor and optionally instructions for expressing the genetic construct in a host cell or tissue.

In one embodiment, the kit contains a chimeric receptor and at least one compound, wherein the ligand binding domain of the chimeric receptor has a W77F mutation in SEQ ID NO: 1, SEQ ID NO: 6, or SEQ ID NO: 10 that confers selective binding to the compound. In some embodiments, the compound is 28S, 34S, 96R, 97R, 131S, 132S, 278S, 279S, and/or 281S. In other embodiments, the compound is 28S, 34S and/or 132S. In another embodiment, the kit contains a chimeric receptor and a compound, wherein the ligand binding domain of the chimeric receptor has a Q79A or Q79G mutation in SEQ ID NO: 1, SEQ ID NO: 6, or SEQ ID NO: 10 that confers selective binding to the compound. In certain embodiments, the compound is 9S, 16S, 22S, 38R, 115S, 117S, 134S, 148S, 149S, 154S, 156S, 157S, 158S, 163S, 164S, 165S, 170R, 292R, 295S, and/or 296S. In other embodiments, the compound is 9S, 16S, 22S, 38R, and/or 165S. In still another embodiment, the kit contains a chimeric receptor and a compound, wherein the ligand binding domain of the chimeric receptor has a L141F or L141P mutation in SEQ ID NO: 1, SEQ ID NO: 6, or SEQ ID NO: 10 that confers selective binding to the compound. In some embodiments, the compound is 19S, 85S, 86S, 88S, 89S, 90S, 91S, 118S, 119S, 120S, 121S, 127S, 208S, 212, 241, 242, 245, 253, 254, 255, and/or 294S. In other embodiments, the compound is 19S, 85S, 86S, 88S, 89S, 90S, and/or 118S.

The present invention also includes a method of treating a disease or disorder associated with the nervous system in a subject in need thereof. In one embodiment, the method comprises delivering a genetic construct to a population of neurons in the subject, wherein the genetic construct encodes a chimeric receptor, wherein the chimeric receptor comprises a ligand binding domain from an α7 nicotinic acetylcholine receptor fused to a transmembrane domain from a ligand-gated ion channel protein, wherein said ligand binding domain comprises at least one mutation that confers selective binding to a compound; and administering the compound to the subject. Preferably, the compound is capable of passing through the blood brain barrier.

Such therapeutic methods find use in disease states or other physiological conditions in which the disease or symptoms can be improved by alteration in neuronal activity. In conditions in which decreasing activity of a subpopulation of neurons provides a therapeutic benefit, an anion-conducting chimeric receptor of the invention (e.g., α7-GlyR or α7-GABA C) may be expressed in such neurons and subsequently activated with its tailored compound to silence these neurons. In such embodiments, the activity of the population of neurons is decreased following administration of the compound to the subject. Conversely, in conditions in which increasing activity of a neuronal subpopulation provides a therapeutic benefit, a cationic-selective chimeric receptor of the invention (e.g., α7-5HT3) may be expressed in such neurons and subsequently activated with its tailored compound to increase action potential frequency in the neurons. In these embodiments, the activity of the population of neurons is increased following administration of the compound to the subject.

By way of example, chronic pain can be treated in a subject with the methods of the invention. Painful stimuli are primarily sensed and propagated to the nervous system by neurons that give rise to axons and dendrites that are referred to as C-fibers. The cell bodies of these neurons are in the dorsal root ganglia, peripheral to the spinal cord. These cell bodies express genes, Substance P and TRPV1, selectively over other neurons in the dorsal root ganglia which pass sensory information such as touch. By using a gene delivery technique as described herein (e.g., a viral vector) to target DNA encoding neuronal silencers such as, but not limited to, α7-GlyR L141F or α7-GABA C L141F under control of either of the substance P or TRPV1 promoters, selective expression of the ion channels is achieved. Once expressing these ion channels, the activity of these neurons can be selectively reduced in the presence of a ligand for these chimeric receptors, such as 89S. Silencing C-fibers blocks painful stimuli from being detected. This approach permits the C-fibers to be selectively silenced without silencing the associated A and delta fibers which are associated with sensing touch. Silencing the C-fibers using less specific techniques than those described here would result in undesired loss of sensation such as numbness instead of selective block of pain.

The invention could also be applied to treatment of epilepsy, which is a disorder of excessive neuronal activity in the brain ultimately leading to seizures. In epilepsy, seizures can result from neuronal overactivity in a specific brain region or foci that can then spread to other brain regions. Neuronal silencers, such as α7-GlyR L141F or α7-GABA C L141F, can be specifically targeted to these overactive brain regions (e.g., neurons in the seizure focus) using viral vectors or other genetic constructs encoding the chimeric channels under the control of neuron-specific promoter fragments, such as the synapsin promoter or neuron-specific enolase promoter. Expression of these channels in the region of interest renders these neurons sensitive to systemically administered synthetic ligands of the invention, such as compound 89, which would silence this brain region only when required (e.g., if a seizure was developing). This would leave the rest of the brain unperturbed, significantly reducing side effects associated with epilepsy therapy. The above-described examples were to illustrate particular embodiments and not to limit the invention in any way. Similar methods could be used to treat other disorders or diseases associated with the nervous system including, but not limited to, Alzheimer's Disease, Parkinson's Disease, Schizophrenia, hypothalamic disorders, and Huntington's Disease.

The examples which follow are set forth to illustrate the present invention, and are not to be construed as limiting thereof.

EXAMPLES

Example 1

Generation of Mutants of the α7 Nicotinic Acetylcholine Receptor Ligand Binding Domain To engineer non-natural pharmacology into the ligand binding domain (LBD) of the α7 nicotinic acetylcholine receptor (nAChR), a model of the ligand-ion channel interaction was developed. This homology model was based on the x-ray crystal structure of the snail acetylcholine binding protein (AChBP) bound to nicotine (Celie et al. (2004) Neuron, Vol. 41: 907-914). The homology model was generated by aligning the sequence from the rat α7 nAChR with the crystal structure of Lymnaea stagnalis (great pond snail) AchBP bound to nicotine (PDB 1UW6) using PROMALS3D. All computational modeling was done within the Chameleon software package. Insertions and deletions in the α7 nAChR sequence relative to AchBP were modeled by search of the Protein Data Bank (PDB) for secondary structure elements with similar termini, using a sliding window through the α7 sequence. Protein side-chains were remodeled using a backbone-independent rotamer library as previously described (Lovell et al. (2000) "The Penultimate Rotamer Library", Proteins: Structure Function and Genetics, Vol. 40: 389-408; Lovell et al. (2003) "Structure Validation by Cα Geometry: φ,ψ and Cβ Deviation", Proteins: Structure, Function and Genetics, Vol. 50: 437-450), with manually-added diversity.

PNU-282987, a selective α7 nAChR agonist, was docked into this homology model, with a binding mode analogous to nicotine, where the protonated tertiary amine interacts with W171 (See FIG. 1C). Note that the amino acid numbering is based on translation of the cDNA sequence used here and includes the signal peptide. The PNU molecule was modeled using Chem3D (CambridgeSoft) and semi-manually docked into the α7 nAChR binding pocket. Specifically, the quaternary amine was superposed onto that of the nicotine molecule, and allowed to rotate freely around the H-N axis, thus preserving this "pharmacophoric" hydrogen bond with the backbone carbonyl of AchBP/α7 nAChR. A minimum-energy conformation was determined, and then the surrounding protein side-chains were placed again in the context of the PNU molecule. The resulting model of the complex was screened for clashes using MolProbity, which were fixed by iterative application of main-chain "backrub" and side-chain optimization. PNU derivatives were also modeled in Chem3D; mutant structures were obtained by selective replacement of single side-chains. All images were produced using PyMOL.

Based on previously reported structure activity relationships of benzamide quinuclidines with the α7-5HT3a chimeric receptor (Bodnar, et al. (2005) Journal of Medicinal Chemistry, Vol. 48: 905-908), we concluded that bulky substitution of the benzamide was detrimental to receptor activity. Therefore, to design α7 nAChR LBDs with selectivity for small molecule agonists, LBD mutations that would accommodate these bulky groups were identified. Mutations were made in amino acids that were adjacent to the benzamide functionality in the homology model (e.g. W77, Q79, Q139, L141; see FIG. 1C). Although the model called for reducing steric bulk in the LBD in order to accommodate bulkier ligands, the modifications of these residues were not limited solely to smaller amino acids. Instead, each of these positions were mutated to one of 19 alternative amino acids generating a total of 76 single mutant channels. See X axis of FIG. 1G for a list of all 76 mutations. This mutational approach was adopted to account for complex interactions in protein structure that can lead to unexpected conformational effects, which may also favor binding of a larger ligand.

Site-directed mutagenesis of a chimeric receptor containing the ligand binding domain from the human α7 nAChR fused to the transmembrane domain of the mouse serotonergic ionotropic receptor (5HT3) was performed using standard techniques to produce each of the 76 single channel mutants described above. The wild-type amino acid sequence for the human/mouse α7-5HT3 chimeric receptor is shown in FIG. 10 (SEQ ID NO: 1).

Example 2

Functional Characterization of α7 nAChR-5HT3 Chimeric Receptor Mutants

As described in Example 1, the human/mouse α7-5HT3 chimeric receptor was used as a template to generate the point mutations in the α7 LBD. This chimeric receptor expresses well in heterologous cell culture systems and it exhibits slower desensitization kinetics relative to the native α7 nAChR (Eisele et al. (1993) Nature, Vol. 366: 479-483). HEK 293 cells (ATCC CRL-1573) were transfected with a single plasmid encoding one of the seventy six single α7-5HT3 receptor mutants using a commercial transfection reagent (FuGene HD, Roche Applied Science). Each of the seventy six different α7-5HT3 receptor mutants were prescreened for ion channel function and cell surface expression.

Ion channel function was measured using a commercially available fluorescence-based membrane potential (MP) assay (MDS Analytical Technologies). Briefly, the MP assay involves loading cells expressing the chimeric receptors with a voltage-sensitive dye, which fluoresces at a particular wavelength upon changes in the cells' membrane potential. Increases in fluorescence correlate with ion flux into the cell, and thus provide a measure of ion channel activity. HEK cells expressing either the wild type α7-5HT3 chimeric receptor or one of the single mutant receptors were exposed to a single concentration of three different conventional ligands for the α7 nAChR: acetylcholine (Ach), nicotine, and PNU-282987 (FIG. 1B). Whole cell voltage clamp recordings of α7-5HT3 responses to PNU-282987 show an initial peak current ($I_{peak}$) which desensitizes ($t_{1/2}$=0.26±0.05 sec) to a steady state current ($I_{SS}$) (FIG. 1D). Because the ultimate application of this channel as a tool with ligand application in times of minutes, $I_{SS}$ is the most relevant value for assessing ligand efficacy. For high throughput measurements of ion channel function, we used a plate reader-compatible fluorescence-based membrane potential (MP) assay (FIG. 1E). The dose response curves from this assay reflected $I_{SS}$ resulting from sustained ligand activation of the channel (FIG. 1F). EC50s for $I_{peak}$ measured in whole cell voltage clamp were typically 3-10 fold higher than for $I_{SS}$ (FIG. 1F, Table 2). Thus, the MP assay is a suitable method for measuring ion channel activation of the α7-5HT3 chimeric receptors. For each of the seventy six mutant chimeric receptors, responses to ACh (100 μM), nicotine (100 μM), and PNU-282987 (10 μM) measured in the MP assay were normalized to the response to ACh (100 μM). The results are shown in the colormap in FIG. 1G.

Cell surface expression of the wild-type and mutant α7-5HT3 chimeric receptors was determined using a fluorescence assay for surface-bound Alexa-594 labeled α-bungarotoxin. The relative amount of cell surface α-bungarotoxin binding sites (e.g. cell surface expression of the chimeric receptors) was measured by normalizing the fluorescent intensity of Alexa-594 labeled α-bungarotoxin bound to cells expressing α7-5HT3 mutant chimeric receptors relative to cells expressing α7-5HT3 under non-permeablizing conditions. Mutant chimeric receptors demonstrating >40% surface expression and >50% activity with any of the three ligands were used for additional dose response assays (FIG. 1G).

Example 3

Figure 2:
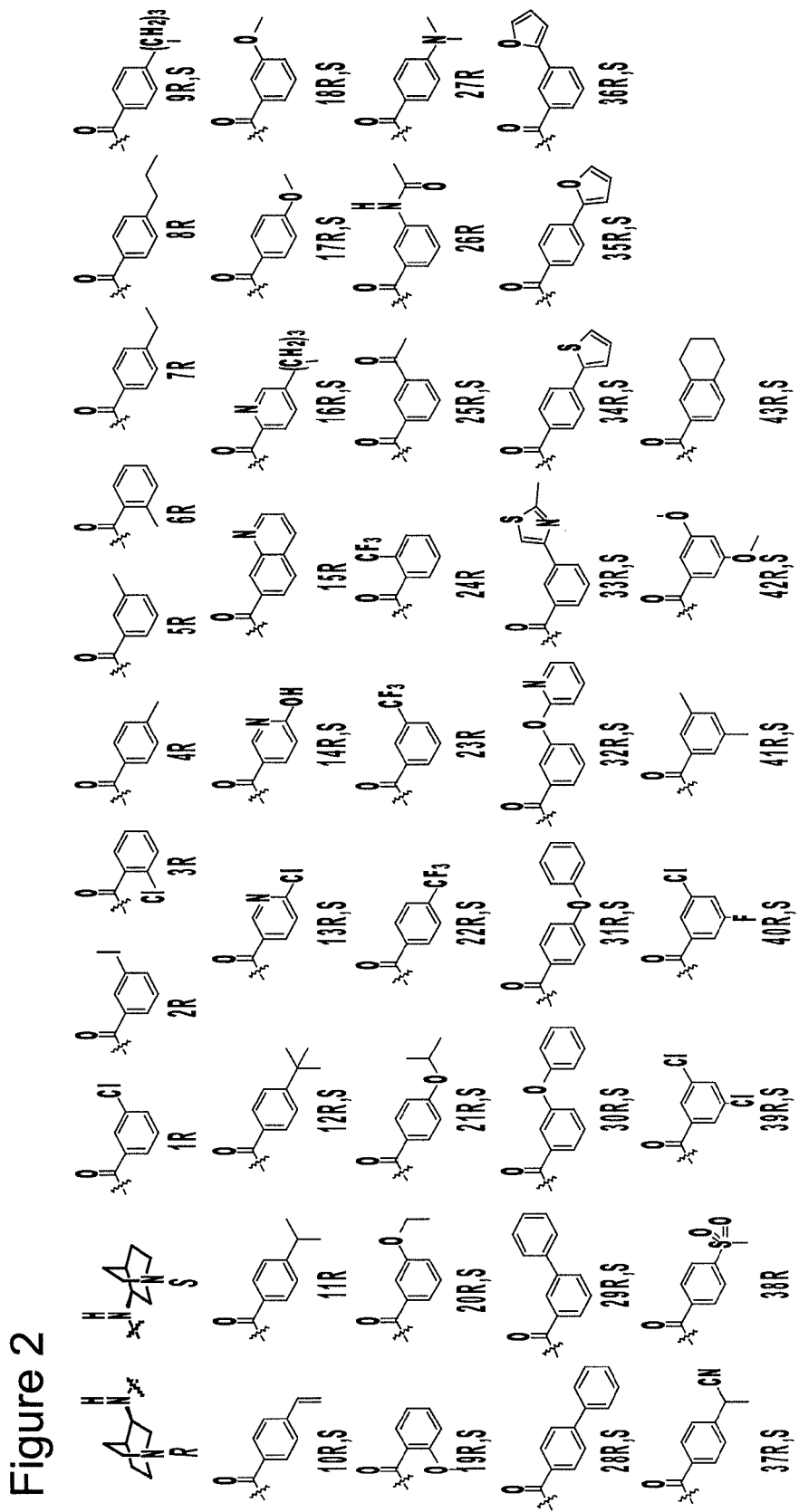
FIG. 2. Components of the quinclidine benzamide library used to identify ligands selective for mutant ligand binding domains. Top left in bold shows the (R)- and (S)-enantiomers of 3-aminoquinulidine that were coupled to the displayed benzoic acid derivatives. Wavy lines indicate joining point to form the quinclidine benzamides. R or S in numbering scheme refers to which enantiomers were synthesized.

Identification of Selective Ligands for Mutant α7 nAChR-5HT3 Chimeric Receptors A focused 71-membered library of 3-aminoquinuclidine benzamides was synthesized (FIG. 2). Representative chemical synthesis procedures for some of the compounds in the library are listed at the end of this Example. It was previously reported that α7-5HT3 is preferentially activated by the R enanantiomer of 3-aminoquinuclidine benzamide (Bodnar et al. (2005) Journal of Medicinal Chemistry, Vol. 48: 905-908). Furthermore, the 2'-substitution of the benzamide and bulky 4'-benzamide substituents were reported to most adversely affect activity of the α7-5HT3 chimeric receptor. Thus, we biased our library of molecules towards substitutents that would be least active against the α7-5HT3 "wild type" (wt) receptor. Additionally, the S enantiomers for many of the compounds were also synthesized.

Using the MP assay, we measured 1118 dose response curves against 43 α7-5HT3 single amino acid mutations and the 3-aminoquinuclidine benzamides as well as ACh, nicotine, and PNU-282987 (FIG. 3). Notably, several mutant ion channel-ligand combinations emerged showing selective activity for the mutant chimeric receptor as compared to the wild-type α7-5HT3 receptor (FIG. 4). In most cases, the S enantiomer of a particular compound conferred the greatest selectivity over the wild-type α7-5HT3 chimeric receptor. One exception was the interaction of 38R with α7-5HT3 Q79G (EC50 =1.6 μM, no activity against α7-5HT3 wt). We selected W77F (SEQ ID NO: 2), Q79G (SEQ ID NO: 3), and L141F (SEQ ID NO: 4) mutant α7-5HT3 chimeric receptors for further investigation. The dose response curves revealed a specific interaction of the W77F, Q79G and L141F mutant chimeric receptors with compounds 28S, 34S, 9S, 22S, 38R, and 19S (FIG. 4). EC50s for activating these mutant chimeric receptors for these three compounds were in the range of 0.8-3 μM. Importantly, these compounds (28S, 34S, 9S, 22S, 38R, and 19S) did not induce activate the unmodified α7-5HT3 receptor. In addition to these compounds, there were a number of selective interactions of α7-5HT3 mutant receptors with compounds from the library exhibiting EC50s around 10 μM.

Figure 5:
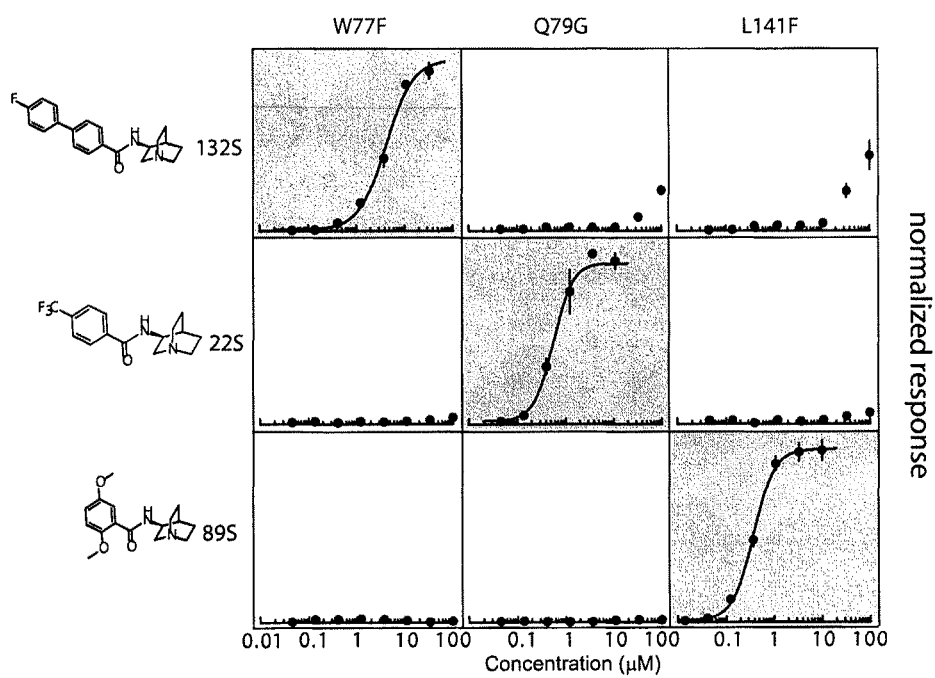
FIG. 5. Dose response curves for mutant ligand-gated ion channel-ligand interactions that show orthogonal pharmacology, indicating that the ligand-ion channel systems can be used in the presence of one another with minimal crosstalk.

Several ligand-ion channel combinations also showed selectivity relative to each another (FIG. 5). Compound 132S (EC50$_{MP}$=4.3±0.5 μM), a fluorinated analog of 28S, selectively activated α7-5HT3 W77F over receptors with the Q79G and L141F mutations. Similarly, 22S and 89S were selective for Q79G and L141F, respectively. Such selectivity is a critical feature for developing tools that allows separate manipulation of multiple neuron populations in the same organism.

To improve the selective interaction of 19S with the α7-5HT3 L141F mutant chimeric receptor, we synthesized and tested eight 3-aminoquinuclidine-2'-alkoxybenzamide analogs (Table 1). The dimethoxy derivatives, 88S and 89S, exhibited 5-10 fold improvement in efficacy against this mutant receptor (EC50$_{MP}$, 88S: 0.1±0.1 μM; 89S: 0.4±0.1 μM) while exhibiting no activity against the α7-5HT3 wt receptor.

TABLE 1

Structure activity relationships of analogs of compound 19S against α7-5HT3 L141F

| Cpd | $R_2$ | $R_3$ | $R_4$ | $R_5$ | EC50$_{MP}$ (μM) |
|---|---|---|---|---|---|
| 19S | OMe | H | H | H | 1.4 ± 0.2 |
| 85S | OEt | H | H | H | 1.4 ± 0.2 |
| 86S | OMe | H | Me | H | 1.4 ± 0.3 |
| 87S | OMe | OMe | H | H | 7.8 ± 2.1* |
| 88S | OMe | H | OMe | H | 0.12 ± 0.01 |
| 89S | OMe | H | H | OMe | 0.40 ± 0.01 |
| 90S | OMe | H | Cl | H | 1.3 ± 0.3 |
| 118S | OMe | H | H | Cl | 2.6 ± 0.3 |
| 109S | 4-THP | H | H | H | >100 |
| 125S | OCF3 | H | H | H | >100 |

Ligand-receptor affinities could also be improved with additional mutations in the ligand binding site. Analysis of dose response curves from α7-5HT3 Q139M channels showed higher efficacy for a number of ligands that activated α7-5HT3 wt. However, there is little selectivity conferred by this mutation. We reasoned that in combination with the selectivity mutations described above, the identified interactions could be improved. In some cases these binding site mutations were compatible, and α7-5HT3 Q79G Q139M showed, relative to α7-5HT3 Q79G, 8- and 20-fold improvement in efficacy over with 38R (EC50$_{MP}$=0.23±0.07 μM) and 22S (EC50$_{MP}$=0.06±0.04 μM), respectively (Table 2, FIG. 6).

Example 4

Efficacy of Mutant α7 nAChR and Chimeric Receptors by Compound Ligands

Several series of small molecules were prepared and the activity and selectivity of the molecules were compared against binding to wild type α7-5HT3. Compounds 28S, 34S, 96R, 97R, 131S, 132S, 278S, 279S, and 281S each have EC50 values of about 100 μM for wt α7-5HT3 and of between about 0.8 and about 7.7 μM for α7-5HT3 W77F. Compounds 165S, 165, 115S, 163S, 117S, 154S, 149S, 164S, 22S, 157S, 170R, 156S, 295S, 292R, 296S, 38R, 134S, and 148S each have EC50 values of about 100 μM for wt α7-5HT3 and EC50 values of between about 0.8 and about 7.8 μM for α7-5HT3 Q79G. Compounds 19S, 85S, 86S, 88S, 89S, 90S, 91S, 118S, 119S, 120S, 121S, 127S, and 294S each have EC50 values of about 100 μM for wt α7-5HT3 and EC50 values of between about 0.1 and about 3.4 μM for α7-5HT3 L141F. Compounds 212, 241, 242, 253, 254, and 255 each have EC50 values of about 100 μM for wt α7-5HT3 and EC50 values of between about 0.1 and about 15 μM for α7-5HT3 L141F.

Table 2 shows representative EC50 values of various synthetic ligands for chimeric channels.

TABLE 2

Efficacy of various ligands against selected mutant chimeric ion channels.

| α7 mutant | IPD | cpd | EC50-MP (μM +/− s.e.m.) | EC50-Iss (μM +/− s.e.m.) | EC50-Ipeak (μM +/− s.e.m.) |
|---|---|---|---|---|---|
| wt | 5HT3 | ACh | 5.4 (1.1) | 26 (6) | 38 (2) |
|  |  | PNU | 0.06 (0.02) | 0.09 (0.02) | 0.8 (0.5) |
|  |  | 212 | >100 | nd | nd |
|  |  | 241 | >100 | nd | nd |
|  |  | 245 | >100 | nd | nd |
| W77F | 5HT3 | 28S | 3.0 (0.1) | 2.4 | 11.3 |
|  |  | 34S | 1.4 (0.1) | nd | nd |
|  |  | 132S | 4.3 (0.5) | nd | nd |
| Q79G | 5HT3 | ACh | 8.2 (2) | 9.3 (3.0) | 38 (13) |
|  |  | 9S | 2.3 (0.9) | 2.3 (0.5) | 4.3 (0.9) |
|  |  | 22S | 0.8 (0.2) | 0.4 (0.2) | 2.7 (0.9) |
|  |  | 38R | 1.6 (0.2) | nd | nd |
|  |  | 165S | 1.9 (0.4) | 0.9 (0.2) | 5.9 (0.1) |
|  |  | 212 | >100 | nd | nd |
|  |  | 241 | >100 | nd | nd |
|  |  | 245 | >100 | nd | nd |
| Q79G Q139M | 5HT3 | 22S | 0.06 (0.04) | nd | nd |
|  |  | 38R | 0.23 (0.07) | nd | nd |
| Q79G Q139G | 5HT3 | ACh | 31 | 47 (2.0) | 296 (64) |
|  |  | 22S | 3.9 | 2.7 (1) | 11.6 (3.6) |
| Q79G L141S | 5HT3 | ACh | >100 | 155 (48) | 356 (16) |
|  |  | 9S | 4.1 (0.2) | 4 (0.2) | 12.3 (1.4) |
| L141F | 5HT3 | 19S | 1.4 (0.2) | nd | nd |
|  |  | 88S | 0.1 (0.1) | nd | nd |
|  |  | 89S | 0.4 (0.1) | 0.7 (0.2) | 3.2 (0.5) |
|  |  | 212 | 0.75 | nd | nd |
|  |  | 241 | 0.1 | nd | nd |
|  |  | 245 | 10 | nd | nd |
| L141F | 5HT3 HC | ACh | nd | 18.1 (5.9) | 21.6 (3.2) |
|  |  | 89S | nd | 1.5 (0.3) | 2.3 (0.3) |
| L141F | GlyR | ACh | nd | 190 (120) | *complex |
|  |  | 89S | nd | 1.8 (0.4) | *complex |
|  |  | 118S | nd | 3.0 (0.8) | 3.2 (0.4) |
|  |  | 119S | nd | 2.5 (0.4) | 3.8 (.9) |
| L141F Y115F | GlyR | ACh | nd | 490 (230) | 590 (200) |
|  |  | 89S | nd | 5.2 (1.9) | 6.9 (1.9) |
| Q79G | GlyR | 22S | nd | 4.8 (1.2) | 7.5 (2.4) |
| L141F | GABAC | 89S | nd | 4.9 (3.2) | 8.8 (1.4) | nd: not determined.
*complex: multiphasic dose response

To develop these selective LBDs for use in the brain, we also reduced the responsiveness to the endogenous ligand, ACh. We focused on shifting $EC50_{Ipeak}$ because steady state concentrations of ACh do not rise above 100 nM (Vinson and Justice (1997) Journal of Neuroscience Methods, Vol. 73: 61-67), which is significantly below activation threshold of this channel. Previously, it was reported for α7 nAChR that mutations at residues equivalent to α7-5HT3 Y115F and Y210F selectively eliminate ACh responsiveness while leaving nicotine efficacy largely unaffected (Galzi et al. (1991) FEBS Letters, Vol. 294: 198-202). Despite the analogous pharmacologic properties of nicotine and aminoquinuclidine benzamides, these mutations greatly reduced or eliminated efficacy of PNU-282987 with α7-5HT3. However, inspection of FIG. 1G revealed multiple binding site mutations which diminish ACh responsiveness. We reasoned that some could be combined with selectivity-inducing mutations to generate ligand binding domains that had orthogonal ligand specificity to the endogenous receptors while being unresponsive to physiologic levels of ACh. Indeed, α7-5HT3 Q79G Q139G retained responsiveness to 22S ($EC50_{Iss}$=2.7±1.0 μM, $EC50_{Ipeak}$=11.6±3.6 μM), while for ACh ($EC50_{Ipeak}$=296±64 μM) the additional Q139G mutation resulted in a nearly 8-fold shift in efficacy from α7-5HT3 Q79G (ACh: $EC50_{Ipeak}$=38±2 μM). Also, for α7-5HT3 Q79G L141S there was only slight shift in the efficacy for 9S, but ACh responsiveness ($EC50_{Ipeak}$=356±16 μM) shifted nearly 10-fold with addition of the L141S mutation (Table 2).

Figure 7:
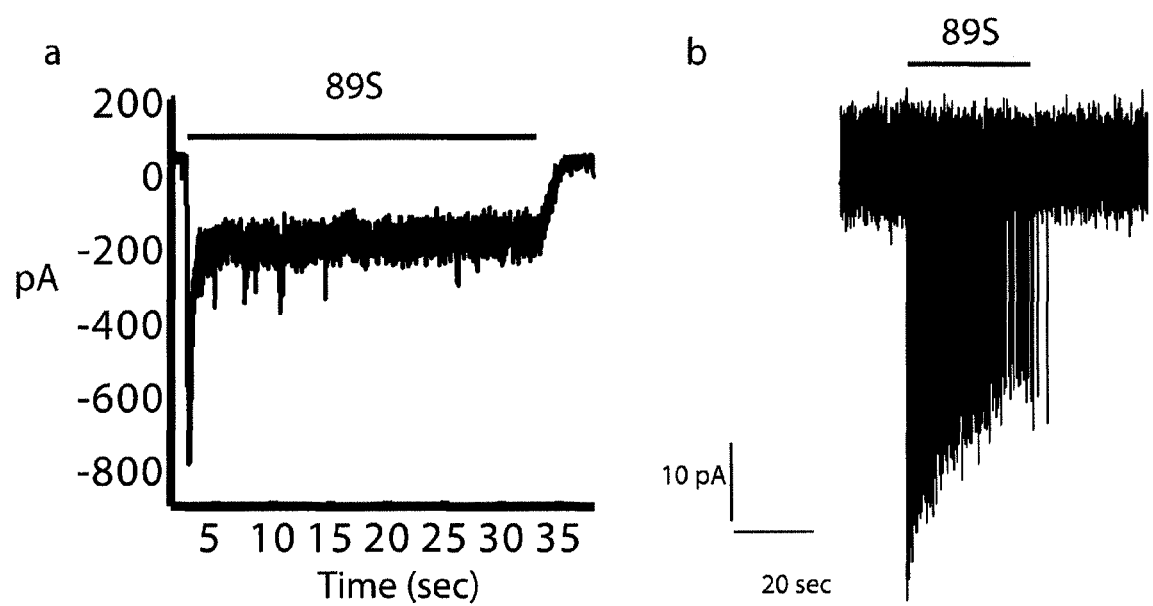
FIG. 7. High conductance chimeric cationic ligand-gated ion channel activates layer ⅔ cortical neurons. A. Current trace from voltage clamp recordings in HEK 293 cells transfected with high conductance (HC) α7-5HT3 L141F receptors showing sustained response of the receptor to compound 89S. B. Cell attached extracellular recording of action currents from mouse layer ⅔ cortical neurons transfected with HC α7-5HT3 L141F. In addition to the mutation in the ligand binding domain (e.g., L141F), these receptors contain high conductance inducing mutations in the α7-5HT3 sequence: R425Q R429D R433A in SEQ ID NO: 1.

To develop a neuron activating cation channel, we further modified the α7-5HT3 channel with three previously described mutations that were reported to provide a 100-fold increase in conductance: R425Q R429D R433A. Addition of this high conductance (HC) mutation, showed the expected increase in channel noise upon ligand application (FIG. 7A). After expression of α7-5HT3 HC L141F in layer ⅔ cortical neurons, compound 89S (3 μM) sustainably increased firing rate in these neurons (FIG. 7B).

Figure 8:
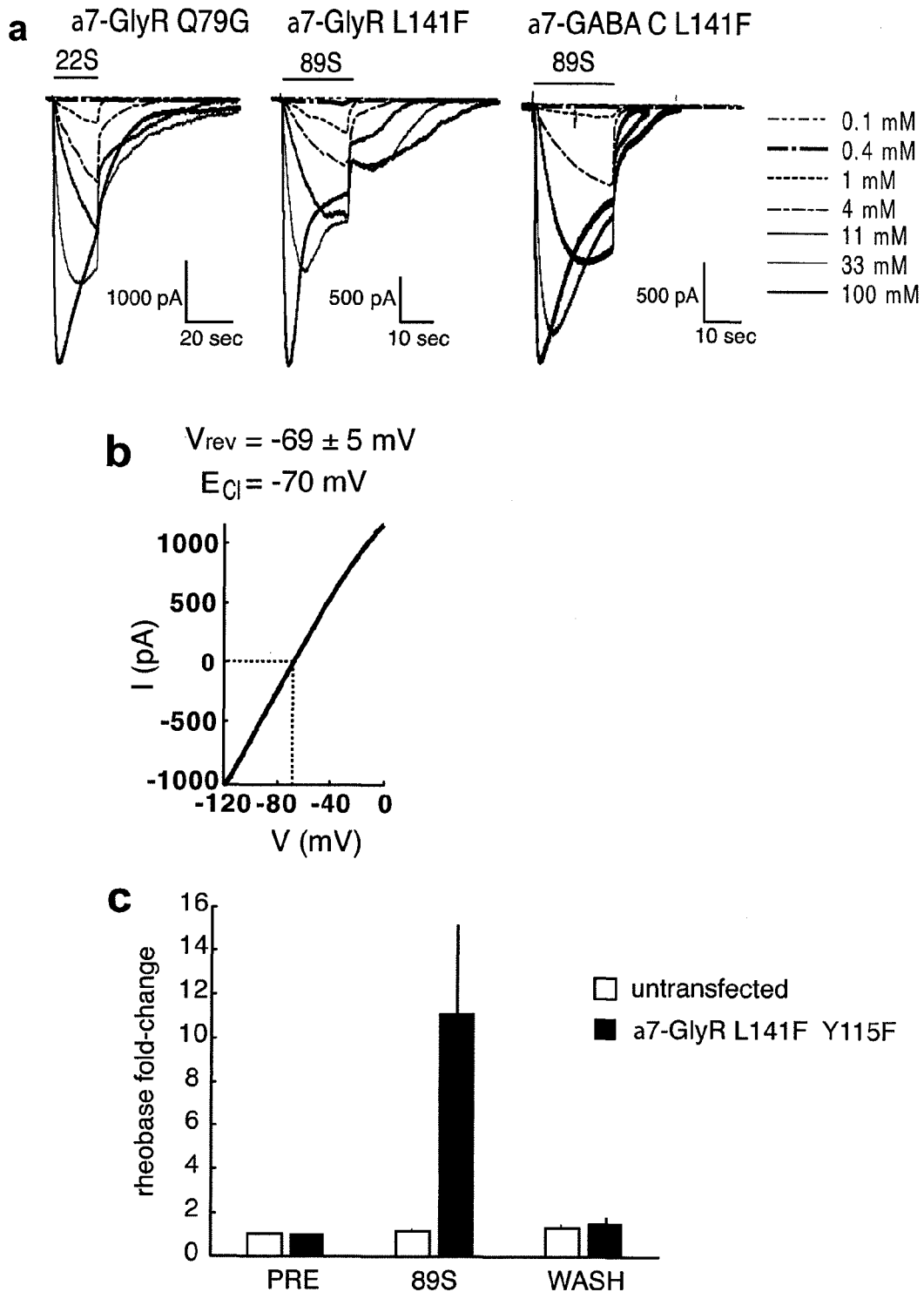
FIG. 8. Chimeric α7-GlyR ligand-gated ion channel conducts chloride and greatly reduces excitability of cortical neurons in the presence of the cognate ligand. A. Current trace from voltage clamp recordings in transfected HEK 293 cells showing sustained responses of α7-GlyR and α7-GABA C mutant chimeric receptors to activation by synthetic ligands of the invention. Black line indicates time course of ligand application. B. I-V trace showing that the reversal potential ($V_{rev}$) of the drug-induced conductance in the chimeric mutant ligand-gated ion channel α7-GlyR L141F is identical to the chloride reversal potential ($E_{Cl}$), indicating that the channel is chloride selective. C. Rheobase, which is the amount of current required to elicit an action potential, is not affected by expression of α7-GlyR L141F Y115F (labeled as condition: PRE). However, rheobase increases 10-fold in the presence of 10 µM compound 89S. There is no change in rheobase in untransfected neurons, even in the presence of 30 µM compound 89S. This reduction of excitability in α7-GlyR L141F Y115F expressing neurons is reversed after washout of the synthetic ligand (labeled as condition: WASH).

For neuron silencing, we generated chimeric channels using α7 Q79G or α7 L141F fused to the glycine receptor IPD (SEQ ID NO: 8 and 9, respectively). These channels produced large, slowly activating currents (FIG. 8A). To maximize orthogonality with the neuronal activators described above, we further developed α7-GlyR L141F (SEQ ID NO: 9). The ligand activated current in cells expressing this channel showed reversal at the chloride reversal potential, indicating that it operated, expectedly, as a chloride channel (FIG. 8B). A notable property is the extremely slow channel activation, which was characterized previously for α7-GlyR (Grater et al. (2005) Proc. Natl. Acad. Sci. USA, Vol. 102: 18207-18212). This slow activation is a useful feature that can be expected to serve as a low pass filter for unwanted activation by fast synaptic ACh activity. ACh-responsiveness can be further diminished by modifying the α7-GlyR L141F with the Y115F mutation which reduced the already low ACh-responsiveness of this channel (Table 2).

Layer 2/3 cortical neurons expressing α7-GlyR L141F Y115F show a dramatically reduced excitability. This was measured by the amount of current required to evoke and action potential, also termed rheobase (FIG. 8C). We found no difference in the rheobase of α7-GlyR L141F Y115F expressing neurons and untransfected cells. However, in the presence of 10 μM compound 89S rheobase increased 10-fold, which demonstrates the strong reduction of excitability in these neurons. Notably, untransfected cells showed no change in rheobase in the presence of compound 89S. Importantly, the effect on neuronal excitability is rapidly reversible and when 89S was washed away with drug-free buffer, the neuronal excitability returned to normal.

Figure 9:
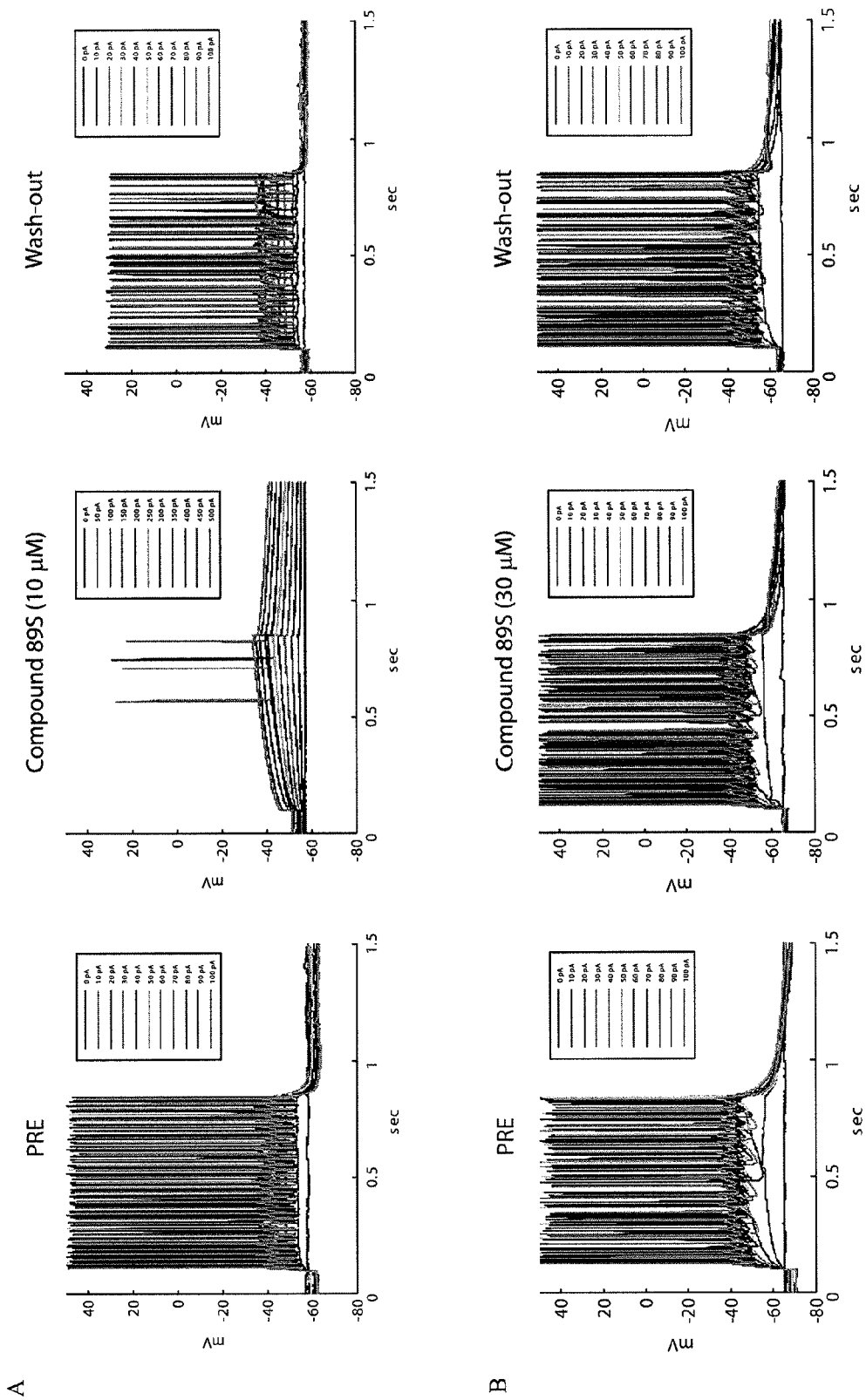
FIG. 9. Synthetic ligand-induced silencing of a cortical neuron transduced by viral gene delivery α7-GlyR L141F mutant chimeric ligand-gated ion channels. Cortical neurons were transduced with adeno-associated virus (AAV) encoding the α7-GlyR L141F mutant chimeric ligand-gated ion channel under the control of the neuron-specific synapsin promoter. A. Excitability of a transfected cortical neuron before, during, and after administration of compound 89S (10 µM). Even after injection of current amplitude up to 500 pA, the neuron is poorly excitable, firing only a few action potentials in the presence of Compound 89S. The neuron fires normally with <100 pA injected current before and after the compound administration. B. Excitability of a non-transduced neuron is shown for comparison. Non-transduced neurons are not affected by administration of compound 89S, even at a higher concentration (30 µM).
Figure 13:
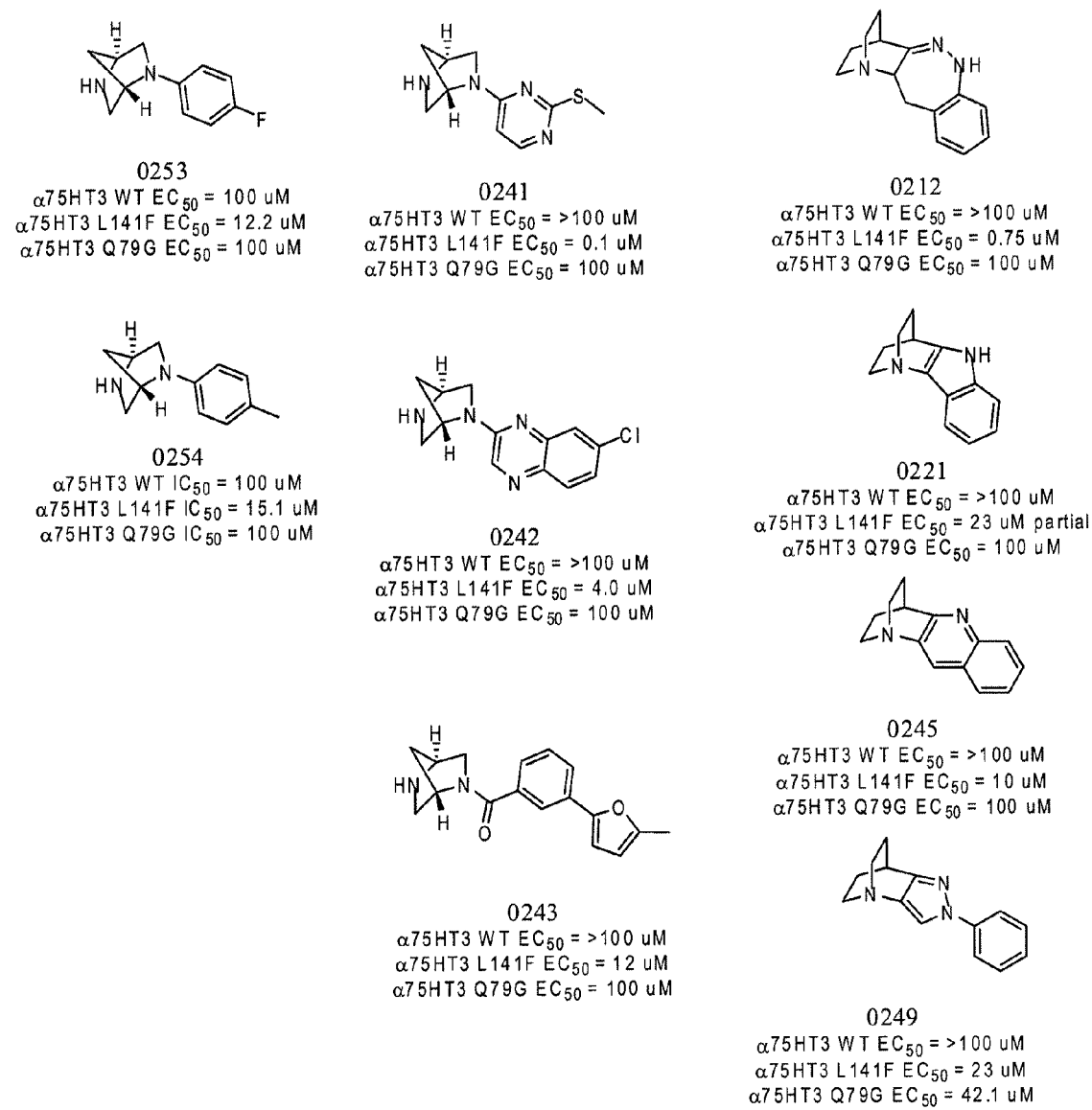
FIG. 13. Synthetic ligands for mutant chimeric α7-5HT3 receptors. The EC50 for each compound for wild-type (WT) and two of the mutant chimeric receptors (Q79G and L141F) are shown below each compound.

We also demonstrated this silencing capability using viral gene delivery vectors with cell type-specific promoters. The synapsin promoter, which restricts gene expression to neuronal cell types, was used to drive expression of α7-GlyR L141F in an adeno-associated virus (AAV) gene delivery vector. Neurons transduced with this virus were rendered sensitive to silencing by compound 89S (FIG. 9A), while untransduced neurons were unaffected by compound 89S (FIG. 9B). These experiments demonstrate the capacity to target specific cell populations with these mutant chimeric ion channels to robustly manipulate electrical activity.

Example 5

Chemical Syntheses

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999.

Preparative HPLC was performed using a Varian PrepStar Model SD-1 instrument with Agilent prep-C18 preparative column 30×150 mm 10 micron. Detection and collection wavelengths were 240 nm and flowrate was 25 ml/min. Solvent A: water with 0.1% TFA, Solvent B: Methanol. Int. 10% B, hold for 5 min at 10% B, 45 min to 60% B.

Example 5A (S)-2-methoxy-N-(quinuclidin-3-yl)benzamide (19S)

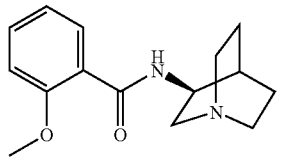 [SMILES: COc1ccccc1C(=O)N[C@@H]1CN2CCC1CC2]

1.5 ml of Acetonitrile and Triethylamine (700 uL, 5.0 mmol) was added to a flask charged with (S)-(-)-3-Aminoquinuclidine dihydrochloride (199 mg, 1.0 mmol) and o-Methoxybenzoic acid (167 mg, 1.1 mmol), followed by addition of 2-Chloro-1-methyl pyridinium iodide (383 mg, 1.5 mmol) at room temperature. After stirring overnight, about 2 ml of water was added to reaction mixture to resolve a clear solution that was subsequently injected into a Preparative HPLC instrument for purification. Desired fractions were combined and concentrated under vacuum. (S)-2-methoxy-N-(quinuclidin-3-yl)benzamide (221 mg, 85% yield) was isolated as an oil. $^1$H NMR (400 MHz, Methanol-D4) δ (ppm): 7.79 (dd, J=7.7 1.6 Hz, 1H), 7.51 (td, J=8.0, 1.6 Hz, 1H), 7.15 (d, J=8.5 Hz, 1H), 7.06 (t, J=7.4 Hz, 1H), 4.45 (m, 4H), 3.97 (s, 3H), 3.82 (ddd, J=11.7, 9.9, 2.0 Hz 1H), 3.37 (m, 4H), 2.37 (q, J=3.2 Hz, 1H), 2.20 (m, 1H), 2.09 (m, 2H), 1.99 (m, 1H). LCMS (ESI): m/z 261.1 (M+H [$C_{15}H_{20}N_2O$]=261.15).

Example 5B (S)—N-(quinuclidin-3-yl)-4-(trifluoromethyl)benzamide (22S)

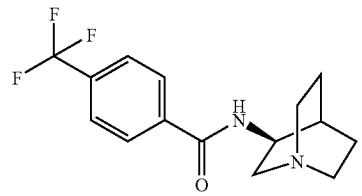

1.5 ml of Acetonitrile and Triethylamine (700 uL, 5.0 mmol) was added to a flask charged with (S)-(-)-3-Aminoquinuclidine dihydrochloride (199 mg, 1.0 mmol) and α,α,α-Trifluoro-p-toluic acid (209 mg, 1.1 mmol), followed by addition of 2-Chloro-1-methyl pyridinium iodide (383 mg, 1.5 mmol) at room temperature. After stirring overnight, about 2 ml of water was added to reaction mixture to resolve a clear solution that was subsequently injected into a Preparative HPLC instrument for purification. Desired fractions were combined, concentrated under vacuum, and then recrystallized from 4 mL of Methanol/water (3:2) to isolate white crystalline solid of (S)—N-(quinuclidin-3-yl)-4-(trifluoromethyl)benzamide (278 mg, 93% yield). $^1$H NMR (400 MHz, Methanol-D4) δ (ppm): 8.05 (d, J=8.2 Hz, 1H), 7.82 (d, J=8.2 Hz, 1H), 4.47 (m, 1H), 3.87 (t, J=11.8, 11.8 Hz, 1H), 3.38 (m, 4H), 2.39 (m, 1H), 2.27 (m, 2H), 2.13 (t, J=8.2 Hz, 1H). LCMS (ESI): m/z 299.1 (M+H [$C_{15}H_{17}F_3N_2O$]=299.13).

Example 5C (S)-4-butyl-N-(quinuclidin-3-yl)benzamide (Compound 9S)

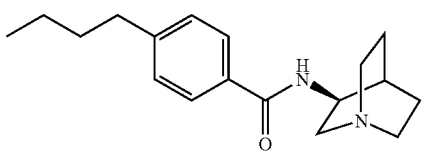 [SMILES: CCCCc1ccc(C(=O)N[C@@H]2CN3CCC2CC3)cc1]

1.5 ml of Acetonitrile and Triethylamine (700 uL, 5.0 mmol) was added to a flask charged with (S)-(-)-3-Aminoquinuclidine dihydrochloride (199 mg, 1.0 mmol) and 4-Butylbenzoic acid (196 mg, 1.1 mmol), followed by addition of 2-Chloro-1-methylpyridinium iodide (383 mg, 1.5 mmol) at room temperature. After stirring overnight, about 2 ml of water was added to reaction mixture to resolve a clear solution that was subsequently injected into a Preparative HPLC instrument for purification. Desired fractions were combined and concentrated under vacuum. (S)-4-butyl-N-(quinuclidin-3-yl)benzamide (272 mg, 95% yield) was isolated as an oil. $^1$H NMR (400 MHz, Methanol-D4) δ (ppm): 8.24 (d, J=8.2 Hz, 2H), 8.41 (d, J=8.4 Hz, 2H), 4.42 (m, 1H), 3.84 (ddd, J=11.7, 9.9, 2.6 Hz, 1H), 3.35 (m, 4H), 2.69 (t, J=7.7 Hz, 2H), 2.36 (q, J=3.1 Hz, 1H), 2.24 (m, 1H), 2.10 (m, 2H), 1.94 (m, 1H), 1.62 (q, J=7.6 Hz, 2H), 1.37 (q, J=7.4 Hz, 2H), 0.95 (t, J=7.4 Hz, 3H). LCMS (ESI): m/z 287.1 (M+H [$C_{18}H_{26}N_2O$]=287.20).

Example 5D (S)-5-butyl-N-(quinuclidin-3-yl)pyridine-2-carboxamide (Compound 16S)

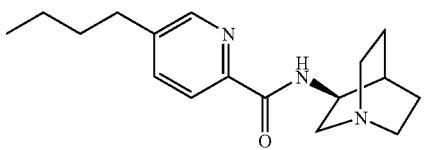 [SMILES: CCCCc1ccc(C(=O)N[C@@H]2CN3CCC2CC3)nc1]

1.5 ml of Acetonitrile and Triethylamine (700 uL, 5.0 mmol) was added to a flask charged with (S)-(−)-3-Aminoquinuclidine dihydrochloride (199 mg, 1.0 mmol) and Fusaric acid (197 mg, 1.1 mmol), followed by addition of 2-Chloro-1-methylpyridinium iodide (383 mg, 1.5 mmol) at room temperature. After stirring overnight, about 2 ml of water was added to reaction mixture to resolve a clear solution that was subsequently injected into a Preparative HPLC instrument for purification. Desired fractions were combined and concentrated under vacuum. (S)-5-butyl-N-(quinuclidin-3-yl)pyridine-2-carboxamide (273 mg, 95% yield) was isolated as clear brown colored oil. $^1$H NMR (400 MHz, Methanol-D4) δ (ppm): 8.52 (d, J=1.8 Hz, 1H), 8.03 (d, J=8.0 Hz, 1H), 7.84 (dd, J=8.0 Hz, 1H), 4.50 (m, 1H), 3.82 (ddd, J=10.0, 3.0, 2.6 Hz, 1H), 3.49 (m, 1H), 3.37 (m, 3H), 2.76 (t, J=7.8 Hz, 2H), 2.38 (m, J=3.1 Hz, 1H), 2.26 (m, 1H), 2.12 (td, J=8.0, 3.1 Hz 2H), 1.96 (m, 1H), 1.68 (m, J=7.7 Hz, 2H), 1.40 (m, J=4.5 Hz, 2H), 0.97 (t, J=7.4 Hz, 3H). LCMS (ESI): m/z 288.1 (M+H [$C_{17}H_{25}N_3O$]=288.20).

Example 5E (S)—N-(quinuclidin-3-yl)-4-(thiophen-2-yl)benzamide (Compound 34S)

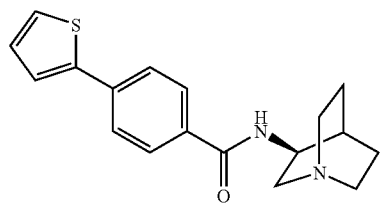 [SMILES: O=C(N[C@@H]1CN2CCC1CC2)c1ccc(-c2cccs2)cc1]

0.5 ml of Acetonitrile, 0.25 ml of water, and Triethylamine (108 uL, 0.78 mmol) was dissolved in a flask charged with (S)-(−)-3-Aminoquinuclidine dihydrochloride (47.8 mg, 0.2 mmol) at room temperature. To the mixture was added 4-(2-Thienyl)benzoic acid (49 mg, 2.4 mmol) and 1-hydroxy benzotriazole (33.8 mg, 0.25 mmol) followed by addition of N,N'-Diisopropyl carbodimide (38.7 uL, 0.25 mmol). The mixture was then stirred overnight at room temperature. About 2 ml of methanol was added to reaction mixture to resolve a clear solution that was subsequently injected into a Preparative HPLC instrument for purification. Desired fractions were combined and concentrated under vacuum. (S)—N-(quinuclidin-3-yl) -4-(thiophen-2-yl)benzamide (8.2 mg, 13% yield) was isolated at an oil. $^1$H NMR (400 MHz, Methanol-D4) δ (ppm): 7.90 (dt, J=8.7, 1.9 Hz, 2H), 7.76 (dt, J=8.6, 1.9 Hz, 2H), 7.53 (dd, J=3.7, 1.1 Hz, 1H), 7.48 (dd, J=4.0, 1.1 Hz, 1H), 7.14 (dd, J=3.5, 1.6 Hz, 1H), 4.45 (m, 1H), 3.86 (ddd, J=10.0, 3.0, 2.5 Hz, 1H), 3.37 (m, 4H), 2.38 (m, 1H), 2.26 (m, 1H), 2.11 (m, 2H), 1.95 (m, 1H). LCMS (ESI): m/z 313.1 (M+H [$C_{18}H_{20}N_2OS$]=313.13).

Example 5F (S)-2,4-dimethoxy-N-(quinuclidin-3-yl)benzamide (Compound 88S)

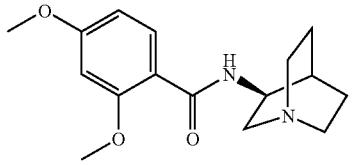 [SMILES: COc1ccc(C(=O)N[C@@H]2CN3CCC2CC3)c(OC)c1]

4.0 ml of DMF, N,N'-Diisopropylethylamine (5.6 ml, 32.14 mmol), and 2,4-Dimethoxybenzoic acid (1.75 g, 9.64 mmol) was added to a flask charged with (S)-(−)-3-Aminoquinuclidine dihydrochloride (1.60 g, 8.03 mmol) and stirred ice-water bath under nitrogen atmosphere. To the mixture was added 2-(1H-7-Azabenzotriazol-1-yl)-1,1,3,3-tetramethyl uronium hexafluorophosphate Methanaminium (3.05 g, 8.03 mmol) then mixture temperature was raised to ambient temperature slowly by removing the ice-water bath for 60 minutes. Reaction mixture was worked up by addition of 1N sodium hydroxide aqueous solution and extracted twice with ethyl acetate, combined organic layer was washed with saturated brine solution, dried over sodium sulfate, filtered, and concentrated to crude clear oil. Purification via preparative HPLC to obtain pure product of (S)-2,4-dimethoxy-N-(quinuclidin-3-yl)benzamide, (1.95 g, 84% yield) $^1$H NMR (400 MHz, Methanol-D4) δ (ppm): 7.42 (m, 1H), 7.11 (s, 2H), 4.45 (m, 1H), 3.95 (s, 3H), 3.83 (m, 1H), 3.80 (s, 3H), 3.39-3.27 (m, 5H), 2.37 (m, 1H), 2.19 (m, 1H), 2.11 (m, 2H), 2.01 (m, 1H). C16H22N2O3 =290.16 LCMS (M+H): m/z 291

Example 5G (S)-4-methyl-N-(quinuclidin-3-yl)benzamide TFA (Compound 176S)

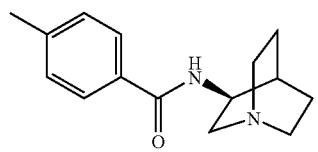 [SMILES: Cc1ccc(C(=O)N[C@@H]2CN3CCC2CC3)cc1]

Title compound was synthesized according to the procedure used in the synthesis of Compound 19S, using 4-methylbenzoic acid in place of o-methoxybenzoic acid. $^1$H NMR (400 MHz, Methanol-D4) δ (ppm): 7.77 (d, J=8 Hz, 2H), 7.30 (d, J=8 Hz, 2H), 4.44 (m, 1H), 3.82 (m, 1H), 3.41-3.27 (m, 5H), 2.40 (s, 3H), 2.35 (m, 1H), 2.24 (m, 1H), 2.09 (m, 2H), 1.92 (m, 1H). $C_{15}H_{20}N_2O$=244.16 LCMS (M+H): m/z 245

Example 5H (S)-4-ethyl-N-(quinuclidin-3-yl)benzamide TFA (Compound 162S)

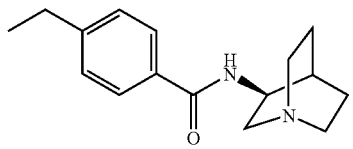 [SMILES: CCc1ccc(C(=O)N[C@@H]2CN3CCC2CC3)cc1]

Title compound was synthesized according to the procedure used in the synthesis of Compound 19S, using 4-ethylbenzoic acid in place of o-methoxybenzoic acid. $^1$H NMR (400 MHz, Methanol-D4) δ (ppm): 7.80 (d, J=8 Hz, 2H), 7.34 (d, J=8 Hz, 2H), 4.44 (m, 1H), 3.84 (m, 1H), 3.37-3.27 (m, 5H), 2.72 (dd, J=16 Hz, 2H), 2.36 (m, 1H), 2.24 (m, 1H), 2.10 (m, 2H), 1.94 (m, 1H), 1.26 (t, J=8 Hz, 3H). $C_{16}H_{22}N_2O$=258.17 LCMS (M+H): m/z 259

Example 5I (S)-4-propyl-N-(quinuclidin-3-yl)benzamide TFA (Compound 165S)

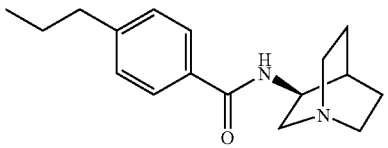 [SMILES: CCCc1ccc(C(=O)N[C@@H]2CN3CCC2CC3)cc1]

Title compound was synthesized according to the procedure used in the synthesis of Compound 19S, using 4-propylbenzoic acid in place of o-methoxybenzoic acid. $^1$H NMR (400 MHz, Methanol-D4) δ (ppm): 7.80 (d, J=8 Hz, 2H), 7.31 (d, J=8 Hz, 2H), 4.44 (m, 1H), 3.83 (m, 1H), 3.41-3.28 (m, 5H), 2.66 (t, J=8 Hz, 2H), 2.36 (m, 1H), 2.24 (m, 1H), 2.09 (m, 2H), 1.93 (m, 1H), 1.67 (m, 2H), 0.95 (t, J=6 Hz, 3H). $C_{17}H_{24}N_2O$=272.19 LCMS (M+H): m/z 273

Example 5J (S)-4-pentyl-N-(quinuclidin-3-yl)benzamide TFA (Compound 115S)

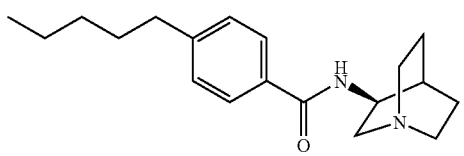 [SMILES: CCCCCc1ccc(C(=O)N[C@@H]2CN3CCC2CC3)cc1]

Title compound was synthesized according to the procedure used in the synthesis of Compound 19S, using 4-pentylbenzoic acid in place of o-methoxybenzoic acid. $^1$H NMR (400 MHz, Methanol-D4) δ (ppm): 7.80 (d, J=8 Hz, 2H), 7.31 (d, J=12 Hz, 2H), 4.45 (m, 1H), 3.82 (m, 1H), 3.43-3.27 (m, 5H), 2.67 (t, J=8 Hz, 2H), 2.36 (m, 1H), 2.24 (m, 1H), 2.09 (m, 2H), 1.92 (m, 1H), 1.64 (m, 2H), 1.34 (m, 2H), 0.90 (t, J=8 Hz, 3H). $C_{19}H_{28}N_2O$=300.22 LCMS (M+H): m/z 301

Example 5K (S)-4-butoxy-N-(quinuclidin-3-yl)benzamide TFA (Compound 116S)

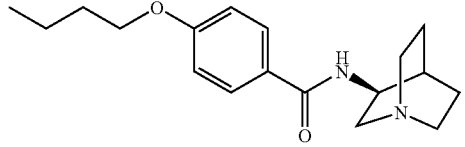 [SMILES: CCCCOc1ccc(C(=O)N[C@@H]2CN3CCC2CC3)cc1]

Title compound was synthesized according to the procedure used in the synthesis of Compound 19S, using 4-butoxybenzoic acid in place of o-methoxybenzoic acid. $^1$H NMR (400 MHz, Methanol-D4) δ (ppm): 7.84 (d, J=8 Hz, 2H), 6.98 (d, J=8 Hz, 2H), 4.43 (m, 1H), 4.04 (t, J=8 Hz, 2H), 3.82 (m, 1H), 3.43-3.27 (m, 5H), 2.35 (m, 1H), 2.24 (m, 1H), 2.09 (m, 2H), 1.92 (m, 1H), 1.78 (m, 2H), 1.52 (m, 2H), 1.00 (t, J=6 Hz, 3H). $C_{18}H_{26}N_2O_2$=302.20 LCMS (M+H): m/z 303

Example 5L (S)-4-(pentyloxy)-N-(quinuclidin-3-yl)benzamide TFA (Compound 117S)

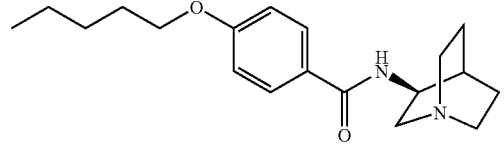 [SMILES: CCCCCOc1ccc(C(=O)N[C@@H]2CN3CCC2CC3)cc1]

Title compound was synthesized according to the procedure used in the synthesis of Compound 19S, using 4-pentyloxybenzoic acid in place of o-methoxybenzoic acid. $^1$H NMR (400 MHz, Methanol-D4) δ (ppm): 7.84 (d, J=8 Hz, 2H), 6.98 (d, J=8 Hz, 2H), 4.43 (m, 1H), 4.04 (t, J=6 Hz, 2H), 3.82 (m, 1H), 3.43-3.27 (m, 5H), 2.35 (m, 1H), 2.24 (m, 1H), 2.09 (m, 2H), 1.93 (m, 1H), 1.80 (m, 2H), 1.44 (m, 4H), 0.95 (t, J=6 Hz, 3H). $C_{19}H_{28}N_2O_2$=316.22 LCMS (M+H): m/z 317

Example 5M (S)-4-isopropyl-N-(quinuclidin-3-yl)benzamide TFA (Compound 163S)

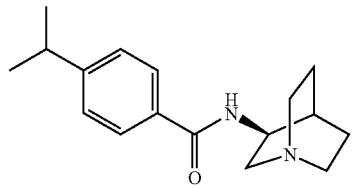 [SMILES: CC(C)c1ccc(C(=O)N[C@@H]2CN3CCC2CC3)cc1]

Title compound was synthesized according to the procedure used in the synthesis of Compound 19S, using 4-isopropylbenzoic acid in place of o-methoxybenzoic acid. $^1$H NMR (400 MHz, Methanol-D4) δ (ppm): 7.80 (d, J=8 Hz, 2H), 7.35 (d, J=8 Hz, 2H), 4.45 (m, 1H), 3.83 (m, 1H), 3.43-3.28 (m, 5H), 2.98 (m, 1H), 2.36 (m, 1H), 2.24 (m, 1H), 2.09 (m, 2H), 1.93 (m, 1H), 1.27 (d, J=8 Hz, 6H). $C_{17}H_{24}N_2O$=272.19 LCMS (M+H): m/z 273

Example 5N (S)-4-(dimethylamino)-N-(quinuclidin-3-yl)benzamide TFA (Compound 164S)

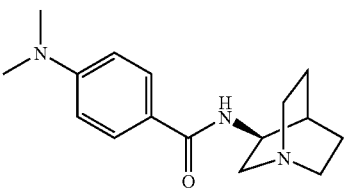 [SMILES: CN(C)c1ccc(C(=O)N[C@@H]2CN3CCC2CC3)cc1]

Title compound was synthesized according to the procedure used in the synthesis of Compound 19S, using 4-dimethylaminobenzoic acid in place of o-methoxybenzoic acid. $^1$H NMR (400 MHz, Methanol-D4) δ (ppm): 7.78 (d, J=8 Hz, 2H), 6.79 (d, J=12 Hz, 2H), 4.41 (m, 1H), 3.82 (m, 1H), 3.43-3.36 (m, 4H), 3.25 (m, 1H), 3.05 (s, 6H), 2.35 (m, 1H), 2.25 (m, 1H), 2.09 (m, 2H), 1.94 (m, 1H). $C_{16}H_{23}N_3O$=273.18 LCMS (M+H): m/z 274

Example 5O (S)-2-fluoro-N-(quinuclidin-3-yl)-4-(trifluoromethyl)benzamide TFA (Compound 157S)

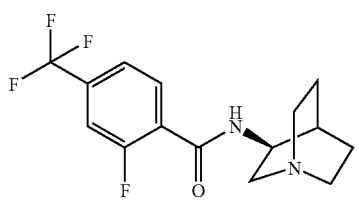 [SMILES: O=C(N[C@@H]1CN2CCC1CC2)c1ccc(C(F)(F)F)cc1F]

Title compound was synthesized according to the procedure used in the synthesis of Compound 19S, using 2-fluoro-4-(trifluoromethyl)benzoic acid in place of o-methoxybenzoic acid. $^1$H NMR (400 MHz, Methanol-D4) δ (ppm): 7.85 (t, J=8 Hz, 1H), 7.61 (t, J=8 Hz, 2H), 4.49 (m, 1H), 3.85 (m, 1H), 3.37 (m, 4H), 3.26 (ddd, J=4, 13, 6 Hz, 1H), 2.38 (m, 1H), 2.21 (m, 1H), 2.11 (td, J=8, 4 Hz, 1H), 1.96 (m, 1H). $Ca_5H_{16}F_4N_2O$=316.12 LCMS (M+H): m/z 317

Example 5P (R)-2-fluoro-N-(quinuclidin-3-yl)-4-(trifluoromethyl)benzamide TFA (Compound 170R)

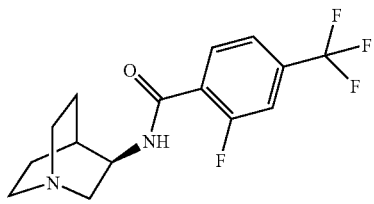 [SMILES: O=C(N[C@H]1CN2CCC1CC2)c1ccc(C(F)(F)F)cc1F]

Title compound was synthesized according to the procedure used in the synthesis of Compound 19S, using 2-fluoro-4-(trifluoromethyl)benzoic acid in place of o-methoxybenzoic acid. $^1$H NMR (400 MHz, Methanol-D4) δ (ppm): 7.85 (t, J=8 Hz, 1H), 7.61 (t, J=8 Hz, 2H), 4.49 (m, 1H), 3.85 (m, 1H), 3.38 (m, 4H), 3.25 (ddd, 1H), 2.38 (m, 1H), 2.21 (m, 1H), 2.11 (m, 2H), 1.96 (m, 1H). $C_{15}H_{16}F_4N_2O$=316.12 LCMS (M+H): m/z 317

Example 5Q (S)-3-fluoro-N-(quinuclidin-3-yl)-4-(trifluoromethyl)benzamide TFA (Compound 156S)

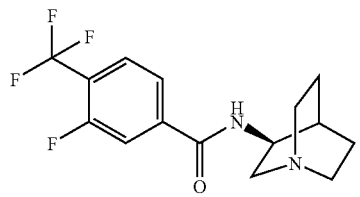 [SMILES: O=C(N[C@@H]1CN2CCC1CC2)c1ccc(C(F)(F)F)c(F)c1]

Title compound was synthesized according to the procedure used in the synthesis of Compound 19S, using 3-fluoro-4-(trifluoromethyl)benzoic acid in place of o-methoxybenzoic acid. $^1$H NMR (400 MHz, Methanol-D4) δ (ppm): 7.82 (m, 3H), 4.47 (m, 1H), 3.84 (m, 1H), 3.48-3.31 (m, 5H), 2.38 (m, 1H), 2.25 (m, 1H), 2.11 (m, 2H), 1.95 (m, 1H). $C_{15}H_{16}F_4N_2O$=316.12 LCMS (M+H): m/z 317

Example 5R (S)—N-(quinuclidin-3-yl)-5-(trifluoromethyl)pyridine-2-carboxamide (Compound 295 S)

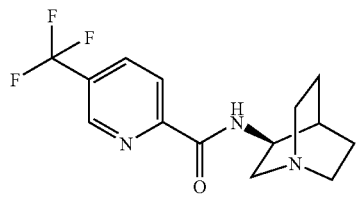 [SMILES: O=C(N[C@@H]1CN2CCC1CC2)c1ccc(C(F)(F)F)cn1]

Title compound was synthesized according to the procedure used in the synthesis of Compound 19S, using 5-(trifluoromethyl)picolinic acid in place of o-methoxybenzoic acid. $^1$H NMR (400 MHz, CDCl$_3$) δ (ppm): 9.06 (s, 1H), 8.30 (dd, J=8 Hz, 1H), 7.79 (d, J=8 Hz, 1H), 6.42 (s, 1H), 4.19 (m, 1H), 3.47 (dd, J=16 Hz, 1H), 2.92-2.85 (m, 4H), 2.64 (ddd, J=16 Hz, 1H), 2.08 (m, 1H), 1.74 (m, 3H), 1.58 (m, 1H). C$_{14}$H$_{16}$F$_3$N$_3$O=299.12 LCMS (M+H): m/z 300

Example 5S (R)—N-(quinuclidin-3-yl)-5-(trifluoromethyl)pyridine-2-carboxamide (Compound 292 R)

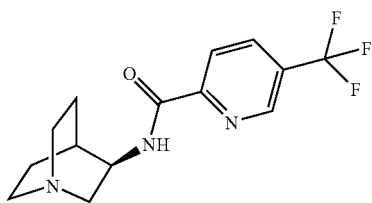 [SMILES: O=C(N[C@H]1CN2CCC1CC2)c1ccc(C(F)(F)F)cn1]

Title compound was synthesized according to the procedure used in the synthesis of Compound 19S, using 5-(trifluoromethyl)picolinic acid in place of o-methoxybenzoic acid. $^1$H NMR (400 MHz, CDCl$_3$) δ (ppm): 8.98 (s, 1H), 8.22 (dd, J=8 Hz, 1H), 7.71 (d, J=8 Hz, 1H), 6.36 (s, 1H), 4.11 (m, 1H), 3.39 (dd, J=16 Hz, 1H), 2.83-2.77 (m, 4H), 2.56 (ddd, J=16 Hz, 1H), 2.00 (m, 1H), 1.66 (m, 3H), 1.50 (m, 1H). C$_{14}$H$_{16}$F$_3$N$_3$O=299.12 LCMS (M+H): m/z 300

Example 5T (R)—N-(quinuclidin-3-yl)-6-(trifluoromethyl)pyridine-3-carboxamide (Compound 293 R)

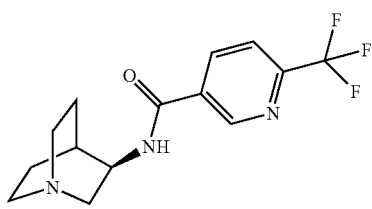 [SMILES: O=C(N[C@H]1CN2CCC1CC2)c1ccc(C(F)(F)F)nc1]

Title compound was synthesized according to the procedure used in the synthesis of Compound 19S, using 6-(trifluoromethyl)nicotinic acid in place of o-methoxybenzoic acid. $^1$H NMR (400 MHz, CDCl$_3$) δ (ppm): 8.84 (s, 1H), 8.34 (dd, J=8 Hz, 1H), 8.23 (s, 1H), 8.12 (dd, J=8 Hz, 1H), 4.18 (m, 1H), 3.39 (ddd, J=10, 14 Hz, 1H), 2.95-2.87 (m, 4H), 2.67 (ddd, J=16 Hz, 1H), 2.06 (m, 1H), 1.79-1.74 (m, 3H), 1.50 (m, 1H). C$_{14}$H$_{16}$F$_3$N$_3$O=299.12 LCMS (M+H): m/z 300

Example 5U (S)—N-(quinuclidin-3-yl)-6-(trifluoromethyl)pyridine-3-carboxamide (Compound 296 S)

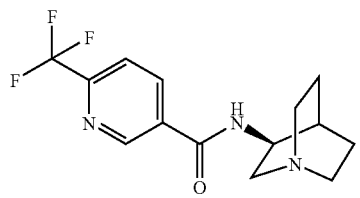 [SMILES: O=C(N[C@@H]1CN2CCC1CC2)c1ccc(C(F)(F)F)nc1]

Title compound was synthesized according to the procedure used in the synthesis of Compound 19S, using 6-(trifluoromethyl)nicotinic acid in place of o-methoxybenzoic acid. $^1$H NMR (400 MHz, CDCl$_3$) S (ppm): 8.84 (s, 1H), 8.34 (dd, J=8 Hz, 1H), 8.23 (s, 1H), 8.12 (dd, J=8 Hz, 1H), 4.18 (m, 1H), 3.39 (ddd, J=10, 14 Hz, 1H), 2.96-2.87 (m, 4H), 2.68 (ddd, J=16 Hz, 1H), 2.06 (m, 1H), 1.82 (m, 1H), 1.74 (m, 1H), 1.55 (m, 1H). C$_{14}$H$_{16}$F$_3$N$_3$O=299.12 LCMS (M+H): m/z 300

Example 5V (S)—N-(quinuclidin-3-yl)-4-(trifluoromethoxy)benzamide TFA (Compound 154S)

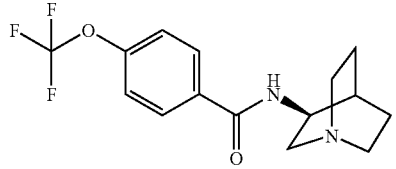 [SMILES: O=C(N[C@@H]1CN2CCC1CC2)c1ccc(OC(F)(F)F)cc1]

Title compound was synthesized according to the procedure used in the synthesis of Compound 19S, using 4-trifluoromethoxybenzoic acid in place of o-methoxybenzoic acid. $^1$H NMR (400 MHz, Methanol-D4) δ (ppm): 7.99 (d, J=8 Hz, 2H), 7.35 (d, J=12 Hz, 2H), 4.47 (m, 1H), 3.84 (m, 1H), 3.47-3.30 (m, 5H), 2.37 (m, 1H), 2.25 (m, 1H), 2.10 (m, 2H), 1.94 (m, 1H). C$_{15}$H$_{17}$F$_3$N$_2$O$_2$=314.12 LCMS (M+H): m/z 315

Example 5W (S)—N-(quinuclidin-3-yl)-4-(trifluoromethylthio)benzamide TFA (Compound 149S)

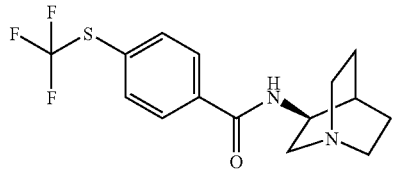 [SMILES: O=C(N[C@@H]1CN2CCC1CC2)c1ccc(SC(F)(F)F)cc1]

Title compound was synthesized according to the procedure used in the synthesis of Compound 19S, using 4-(trifluoromethylthio)benzoic acid in place of o-methoxybenzoic acid. $^1$H NMR (400 MHz, Methanol-D4) δ (ppm): 7.97 (d, J=8 Hz, 2H), 7.82 (d, J=8 Hz, 2H), 4.46 (m, 1H), 3.84 (m, 1H), 3.42-3.29 (m, 5H), 2.38 (m, 1H), 2.25 (m, 1H), 2.10 (m, 2H), 1.94 (m, 1H). $C_{15}H_{17}F_3N_2OS$=330.10 LCMS (M+H): m/z 331

Example 5X (S)-4-(neopentyloxy)-N-(quinuclidin-3-yl)benzamide TFA (Compound 158S)

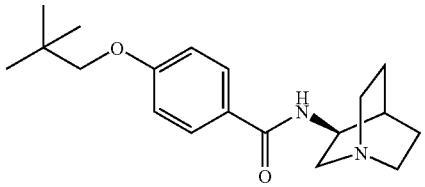 [SMILES: CC(C)(C)COc1ccc(C(=O)N[C@@H]2CN3CCC2CC3)cc1]

Title compound was synthesized according to the procedure used in the synthesis of Compound 19S, using 4-tert-butoxybenzoic acid in place of o-methoxybenzoic acid. $^1$H NMR (400 MHz, Methanol-D4) δ (ppm): 7.86 (d, J=12 Hz, 2H), 7.00 (d, J=8 Hz, 2H), 4.43 (m, 1H), 3.82 (m, 1H), 3.69 (s, 2H), 3.42-3.29 (m, 5H), 2.35 (m, 1H), 2.24 (m, 1H), 2.08 (m, 2H), 1.92 (m, 1H), 1.05 (s, 9H). $C_{19}H_{28}N_2O_2$=316.22 LCMS (M+H): m/z 317

Example 5Y (R)-4-(methylsulfonyl)-N-(quinuclidin-3-yl)benzamide TFA (Compound 38R)

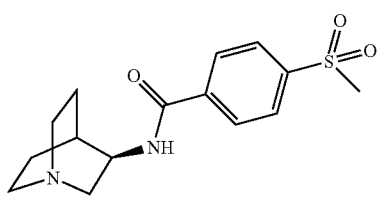 [SMILES: CS(=O)(=O)c1ccc(C(=O)N[C@H]2CN3CCC2CC3)cc1]

Title compound was synthesized according to the procedure used in the synthesis of Compound 34S using 4-(methylsulfonyl)benzoic acid in place of 4-(2-thienyl)benzoic acid. $^1$H NMR (400 MHz, Methanol-D4) δ (ppm): 8.08 (d, J=4 Hz, 4H), 4.47 (m, 1H), 3.86 (m, 1H), 3.45-3.31 (m, 5H), 3.18 (s, 3H), 2.38 (m, 1H), 2.26 (m, 1H), 2.11 (m, 2H), 1.95 (m, 1H). $C_{15}H_{20}N_2O_3S$=308.12 LCMS (M+H): m/z 309

Example 5Z (S)-4-(methylsulfonyl)-N-(quinuclidin-3-yl)benzamide TFA (Compound 134S)

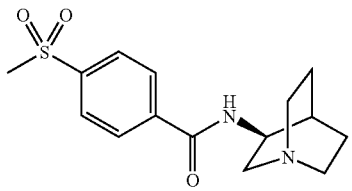 [SMILES: CS(=O)(=O)c1ccc(C(=O)N[C@@H]2CN3CCC2CC3)cc1]

Title compound was synthesized according to the procedure used in the synthesis of Compound 19S, using 4-(methylsulfonyl)benzoic acid in place of o-methoxybenzoic acid. $^1$H NMR (400 MHz, Methanol-D4) δ (ppm): 8.08 (d, J=4 Hz, 4H), 4.47 (m, 1H), 3.86 (m, 1H), 3.42-3.30 (m, 5H), 3.18 (s, 3H), 2.39 (m, 1H), 2.26 (m, 1H), 2.11 (m, 2H), 1.96 (m, 1H). $C_{15}H_{20}N_2O_3S$=308.12 LCMS (M+H): m/z 309

Example 5AA (S)-3-(methylsulfonyl)-N-(quinuclidin-3-yl)benzamide TFA (Compound 148S)

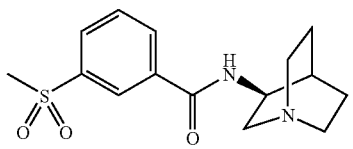 [SMILES: CS(=O)(=O)c1cccc(C(=O)N[C@@H]2CN3CCC2CC3)c1]

Title compound was synthesized according to the procedure used in the synthesis of Compound 19S, using 3-(methylsulfonyl)benzoic acid in place of o-methoxybenzoic acid. $^1$H NMR (400 MHz, Methanol-D4) δ (ppm): 8.44 (t, 1H), 8.21 (dt, J=8 Hz, 1H), 8.15 (dt, J=8 Hz, 1H), 7.77 (t, J=8 Hz, 1H), 4.48 (m, 1H), 3.86 (m, 1H), 3.44-3.30 (m, 5H), 3.18 (s, 3H), 2.40 (m, 1H), 2.27 (m, 1H), 2.11 (m, 2H), 1.95 (m, 1H). $C_{15}H_{20}N_2O_3S$=308.12 LCMS (M+H): m/z 309

Example 5AB (S)-2-propoxy-N-(quinuclidin-3-yl)benzamide TFA (Compound 208S)

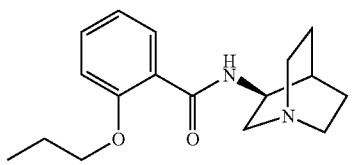 [SMILES: CCCOc1ccccc1C(=O)N[C@@H]1CN2CCC1CC2]

Title compound was synthesized according to the procedure used in the synthesis of Compound 19S, using o-propoxybenzoic acid in place of o-methoxybenzoic acid. $^1$H NMR (400 MHz, Methanol-D4) δ (ppm): 7.81 (dd, J=8 Hz, 1H), 7.50 (m, 1H), 7.15 (d, J=8 Hz, 1H), 7.05 (td, J=6 Hz, 1H), 4.45 (m, 1H), 4.13 (m, 2H), 3.87 (m, 1H), 3.39 (m, 4H), 3.22 (m, 1H), 2.35 (m, 1H), 2.20 (m, 1H), 2.11 (m, 2H), 2.01 (m, 1H), 1.91 (m, 2H), 1.08 (t, J=6 Hz 3H). $C_{17}H_{24}N_2O_2$=288.18 LCMS (M+H): m/z 289

Example 5AC (S)-2-methoxy-4-methyl-N-(quinuclidin-3-yl)benzamide TFA (Compound 86S)

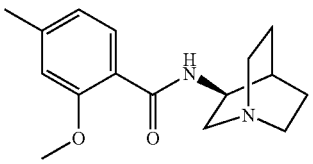 [SMILES: COc1cc(C)ccc1C(=O)N[C@@H]1CN2CCC1CC2]

Title compound was synthesized according to the procedure used in the synthesis of Compound 19S, using 2-methoxy-4-methylbenzoic acid in place of o-methoxybenzoic acid. $^1$H NMR (400 MHz, Methanol-D4) δ (ppm): 7.75 (d, J=8 Hz, 1H), 7.00 (s, 1H), 6.90 (d, J=8 Hz, 1H), 4.44 (m, 1H), 3.98 (s, 3H), 3.38-3.39 (m, 5H), 2.41 (s, 3H), 2.37 (m, 1H), 2.19 (m, 1H), 2.10 (m, 2H), 2.00 (m, 1H). $C_{16}H_{22}N_2O_2$=274.17 LCMS (M+H): m/z 275

Example 5AD (S)-2,5-dimethoxy-N-(quinuclidin-3-yl)benzamide (Compound 89S)

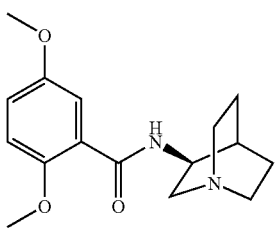 [SMILES: COc1ccc(OC)c(C(=O)N[C@@H]2CN3CCC2CC3)c1]

Title compound was synthesized according to the procedure used in the synthesis of Compound 88S using 2,5-dimethoxybenzoic acid in place of 2,4-dimethoxybenzoic acid. $^1$H NMR (400 MHz, Acetone-D4) δ (ppm): 7.61 (m, J=4 Hz, 1H), 7.11 (s, 1H), 7.07 (m, J=4 Hz, 1H), 4.07 (m, 1H), 4.00 (s, 3H), 3.80 (s, 3H), 3.34 (s, 3H), 2.89-2.82 (m, 4H), 2.62 (m, 1H), 1.98 (m, 1H), 1.84 (m, 1H), 1.84 (m, 2H), 1.52 (m, 1H). $C_{16}H_{22}N_2O_3$=290.16 LCMS (M+H): m/z 291

Example 5AE (S)-4-chloro-2-methoxy-N-(quinuclidin-3-yl)benzamide (Compound 90S)

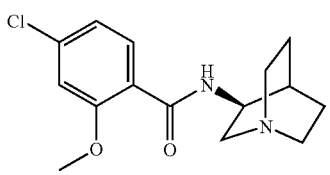 [SMILES: COc1cc(Cl)ccc1C(=O)N[C@@H]1CN2CCC1CC2]

Title compound was synthesized according to the procedure used in the synthesis of Compound 34S using 4-chloro-2-methoxybenzoic acid in place of 4-(2-thienyl)benzoic acid. $^1$H NMR (400 MHz, Methanol-D4) δ (ppm): 7.75 (d, J=8 Hz, 1H), 7.21 (s, 1H), 7.09 (dd, J=8 Hz, 1H), 4.44 (m, 1H), 3.98 (s, 3H), 3.80 (m, 3H), 3.38-3.27 (m, 3H), 2.37 (m, 1H), 2.18 (m, 1H), 2.10 (m, 2H), 1.98 (m, 1H). $C_{16}H_{22}N_2O_2$=294.11 LCMS (M+H): m/z 295

Example 5AF (S)-2-phenoxy-N-(quinuclidin-3-yl)benzamide TFA (Compound 91S)

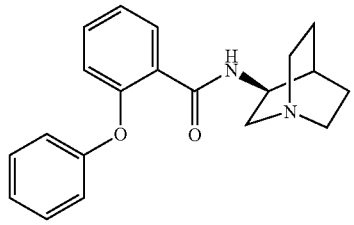 [SMILES: O=C(N[C@@H]1CN2CCC1CC2)c1ccccc1Oc1ccccc1]

Title compound was synthesized according to the procedure used in the synthesis of Compound 34S using 2-phenoxybenzoic acid in place of 4-(2-thienyl)benzoic acid. $^1$H NMR (400 MHz, Methanol-D4) δ (ppm): 7.74 (dd, J=8 Hz, 1H), 7.51 (m, 1H), 7.38 (m, 1H), 7.28 (td, J=8 Hz, 1H), 7.15 (t, J=8 Hz, 1H), 7.01 (m, 1H), 4.33 (m, 1H), 3.74 (m, 3H), 3.29 (m, 3H), 3.16 (m, 1H), 2.97 (m, 1H), 2.19 (m, 1H), 2.02 (m, 3H), 1.82 (m, 1H). $C_{20}H_{22}N_2O_2$=322.17 LCMS (M+H): m/z 323

Example 5AG (S)-5-chloro-2-methoxy-N-(quinuclidin-3-yl)benzamide TFA (Compound 118S)

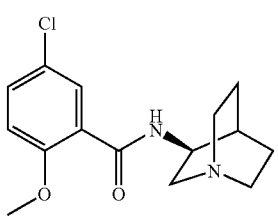 [SMILES: COc1ccc(F)cc1C(=O)N[C@@H]1CN2CCC1CC2]

Title compound was synthesized according to the procedure used in the synthesis of Compound 19S, using 5-chloro-2-methoxybenzoic acid in place of o-methoxybenzoic acid. $^1$H NMR (400 MHz, Methanol-D4) δ (ppm): 7.74 (d, J=4 Hz, 1H), 7.49 (dd, J=8 Hz, 1H), 7.16 (d, J=12 Hz, 1H), 4.33 (m, 1H), 3.97 (s, 3H), 3.82 (m, 1H), 3.38 (m, 4H), 3.27 (m, 1H), 2.37 (m, 1H), 2.18 (m, 1H), 2.10 (m, 3H), 1.99 (m, 1H). $C_{15}H_{19}ClN_2O_2$=294.11 LCMS (M+H): m/z 295

Example 5AH (S)-5-fluoro-2-methoxy-N-(quinuclidin-3-yl)benzamide TFA (Compound 119S)

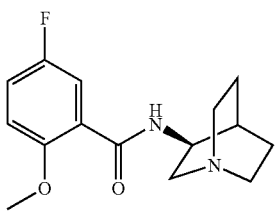

Title compound was synthesized according to the procedure used in the synthesis of Compound 19S, using 5-fluoro-2-methoxybenzoic acid in place of o-methoxybenzoic acid. $^1$H NMR (400 MHz, Methanol-D4) δ (ppm): 7.54 (m, 1H), 7.27 (m, 1H), 7.17 (m, 1H), 4.45 (m, 1H), 3.97 (s, 3H), 3.83 (m, 1H), 3.39 (m, 4H), 3.27 (m, 1H), 2.38 (m, 1H), 2.19 (m, 1H), 2.10 (m, 2H), 1.99 (m, 1H). $C_{15}H_{19}FN_2O_2$=278.14 LCMS (M+H): m/z 279

Example 5AI (S)-2-methoxy-5-methyl-N-(quinuclidin-3-yl)benzamide TFA (Compound 120S)

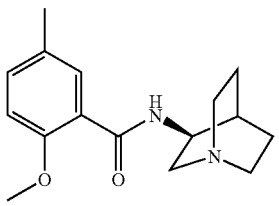 [SMILES: COc1ccc(C)cc1C(=O)N[C@@H]1CN2CCC1CC2]

Title compound was synthesized according to the procedure used in the synthesis of Compound 19S, using 2-methoxy-5-methylbenzoic acid in place of o-methoxybenzoic acid. $^1$H NMR (400 MHz, Methanol-D4) δ (ppm): 7.62 (m, 1H), 7.32 (m, 1H), 7.04 (d, J=4 Hz, 1H), 4.44 (m, 1H), 3.94 (s, 3H), 3.82 (m, 1H), 3.38-3.27 (m, 5H), 2.36 (m, 1H), 2.31 (s, 3H), 2.19 (m, 1H), 2.10 (m, 2H), 1.99 (m, 1H). $C_{16}H_{22}N_2O_2$=274.17 LCMS (M+H): m/z 275

Example 5AJ (S)-2,4,5-trimethoxy-N-(quinuclidin-3-yl)benzamide TFA (Compound 121S)

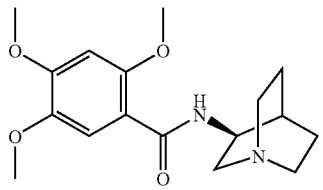 [SMILES: COc1cc(OC)c(C(=O)N[C@@H]2CN3CCC2CC3)cc1OC]

Title compound was synthesized according to the procedure used in the synthesis of Compound 19S, using 2,4,5-trimethoxybenzoic acid in place of o-methoxybenzoic acid. $^1$H NMR (400 MHz, Methanol-D4) δ (ppm): 7.50 (s, 1H), 6.76 (s, 1H), 4.44 (m, 1H), 4.02 (s, 3H), 3.93 (s, 3H), 3.82 (s, 3H, m, 1H), 3.40-3.28 (m, 5H), 2.36 (m, 1H), 2.17 (m, 1H), 2.10 (m, 2H), 2.01 (m, 1H). $C_{17}H_{24}N_2O_4$=320.17 LCMS (M+H): m/z 321

Example 5AK (S)—N-(quinuclidin-3-yl)-2-(trifluoromethoxy)benzamide TFA (Compound 122S)

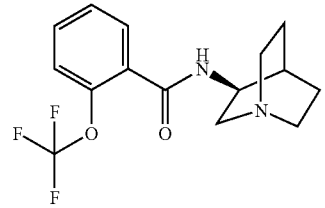 [SMILES: O=C(N[C@@H]1CN2CCC1CC2)c1ccccc1OC(F)(F)F]

Title compound was synthesized according to the procedure used in the synthesis of Compound 19S, using 2-(trifluoromethoxy)benzoic acid in place of o-methoxybenzoic acid. $^1$H NMR (400 MHz, Methanol-D4) δ (ppm): 7.64 (m, 2H), 7.48 (td, J=8 Hz 1H), 7.42 (m, 1H), 4.48 (m, 1H), 3.85 (m, 1H), 3.37 (m, 4H), 3.17 (m, 1H), 2.33 (m, 1H), 2.20 (m, 1H), 2.10 (m, 2H), 1.95 (m, 1H). $C_{17}H_{24}F_3N_2O_2$=314.12 LCMS (M+H): m/z 315

Example 5AL (S)-3-methoxy-N-(quinuclidin-3-yl)naphthalene-2-carboxamide TFA (Compound 127S)

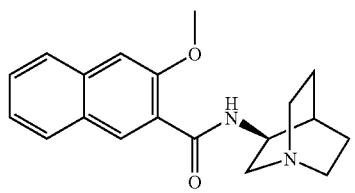 [SMILES: COc1cc2ccccc2cc1C(=O)N[C@@H]1CN2CCC1CC2]

Title compound was synthesized according to the procedure used in the synthesis of Compound 19S, using 3-methoxy-2-naphthoic acid in place of o-methoxybenzoic acid. $^1$H NMR (400 MHz, Methanol-D4) δ (ppm): 8.26 (s, 1H), 7.85 (d, 2H), 7.53 (m, 1H), 7.40 (m, 1H), 4.49 (m, 1H), 4.04 (s, 3H), 3.84 (m, 1H), 3.39-3.29 (m, 5H), 2.40 (m, 1H), 2.23 (m, 1H), 2.10 (m, 2H), 1.99 (m, 1H). $C_{19}H_{22}N_2O_2$=310.17 LCMS (M+H): m/z 311

Example 5AM (S)-2,4,6-trimethoxy-N-(quinuclidin-3-yl)benzamide TFA (Compound 211S)

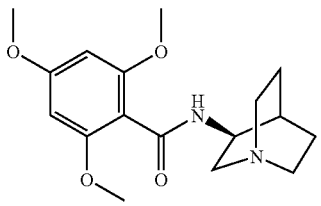 [SMILES: COc1cc(OC)c(C(=O)N[C@@H]2CN3CCC2CC3)c(OC)c1]

Title compound was synthesized according to the procedure used in the synthesis of Compound 19S, using 2,4,6-trimethoxy benzoic acid in place of o-methoxybenzoic acid. $^1$H NMR (400 MHz, Methanol-D4) δ (ppm): 6.24 (s, 1H), 4.13 (m, 1H), 3.83 (s, 3H), 3.80 (s, 6H), 3.38 (m, 1H), 2.94 (m, 4H), 2.76 (m, 1H), 2.12 (m, 1H), 2.00 (m, 1H), 1.82 (m, 2H), 1.59 (m, 1H). $C_{17}H_{24}N_2O_4$=320.17 LCMS (M+H): m/z 321

Example 5AN (S)-2-methoxy-N-(quinuclidin-3-yl)pyridine-3-carboxamide (Compound 294S)

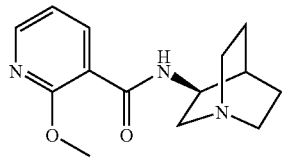 [SMILES: COc1ncccc1C(=O)N[C@@H]1CN2CCC1CC2]

Title compound was synthesized according to the procedure used in the synthesis of Compound 19S, using 2-methoxynicotinic acid in place of o-methoxybenzoic acid. $^1$H NMR (400 MHz, CDCl$_3$) δ (ppm): 8.51 (dd, J=8 Hz 1H), 8.28 (dd, J=6 Hz 1H), 7.07 (dd, J=8 Hz 1H), 4.16 (s, 3H, m, 1H), 3.44 (dd, J=12 Hz, 1H), 2.92 (t, J=8 Hz 2H), 2.85 (m, 2H), 2.61 (ddd, J=16, 12 Hz, 1H), 2.03 (m, 1H), 1.75 (m, 3H), 1.59 (m, 1H). $C_{14}H_{19}N_3O_2$=261.15 LCMS (M+H): m/z 262

Example 5AO (S)-2-ethoxy-N-(quinuclidin-3-yl)benzamide TFA (Compound 85S)

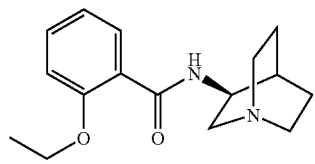 [SMILES: CCOc1ccccc1C(=O)N[C@@H]1CN2CCC1CC2]

Title compound was synthesized according to the procedure used in the synthesis of Compound 19S, using o-ethoxybenzoic acid in place of o-methoxybenzoic acid. $^1$H NMR (400 MHz, Methanol-D4) δ (ppm): 7.85 (dd, J=8 Hz, 1H), 7.50 (m, 1H), 7.12 (d, J=8 Hz, 1H), 7.85 (t, 1H), 4.45 (m, 1H), 4.23 (m, 2H), 3.87 (m, 1H), 3.41 (m, 4H), 3.25 (m, 1H), 2.37 (m, 1H), 2.22 (m, 1H), 2.11 (m, 2H), 2.02 (m, 1H), 1.51 (m, J=6 Hz, 3H). $C_{16}H_{22}N_2O_2$=274.17 LCMS (M+H): m/z 275

Example 5AP (S)—N-(quinuclidin-3-yl)biphenyl-4-carboxamide TFA (Compound 28S)

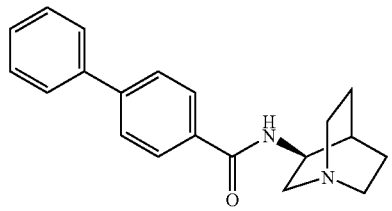 [SMILES: O=C(N[C@@H]1CN2CCC1CC2)c1ccc(-c2ccccc2)cc1]

Title compound was synthesized according to the procedure used in the synthesis of Compound 19S, using biphenyl-4-carboxylic acid in place of o-methoxybenzoic acid. $^1$H NMR (400 MHz, Methanol-D4) δ (ppm): 7.86 (d, J=8 Hz, 2H), 7.63 (d, J=12 Hz, 2H), 7.57 (d, J=8 Hz, 2H), 7.37 (t, J=8 Hz, 2H), 7.29 (t, J=8 Hz, 1H), 4.38 (m, 1H), 3.75 (m, 1H), 3.36 (m, 1H), 3.26 (m, 4H), 2.28 (m, 1H), 2.17 (m, 1H), 2.00 (m, 2H), 1.84 (m, 1H). $C_{20}H_{22}N_2O$=306.17 LCMS (M+H): m/z 307

Example 5AQ (R)-4'-propyl-N-(quinuclidin-3-yl)biphenyl-4-carboxamide TFA (Compound 96R)

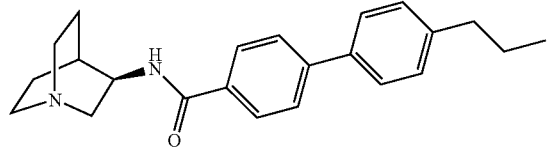 [SMILES: CCCc1ccc(-c2ccc(C(=O)N[C@H]3CN4CCC3CC4)cc2)cc1]

Title compound was synthesized according to the procedure used in the synthesis of Compound 19S, using 4'-propylbiphenyl-4-carboxylic acid in place of o-methoxybenzoic acid. $^1$H NMR (400 MHz, Methanol-D4) δ (ppm): 7.80 (d, J=8 Hz, 2H), 7.73 (d, J=8 Hz, 2H), 7.59 (d, J=8 Hz, 2H), 7.29 (d, J=8 Hz, 2H), 4.47 (m, 1H), 3.86 (m, 1H), 3.45-3.30 (m, 5H), 2.64 (t, J=8 Hz, 2H), 2.39 (m, 1H), 2.27 (m, 1H), 2.11 (m, 2H), 1.95 (m, 1H), 1.69 (m, 2H), 0.97 (d, J=8 Hz, 3H). $C_{23}H_{28}N_2O$=348.22 LCMS (M+H): m/z 349

Example 5AR (S)-4'-propyl-N-(quinuclidin-3-yl)biphenyl-4-carboxamide TFA (Compound 131S)

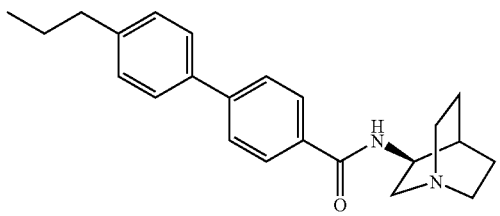 [SMILES: CCCc1ccc(-c2ccc(C(=O)N[C@@H]3CN4CCC3CC4)cc2)cc1]

Title compound was synthesized according to the procedure used in the synthesis of Compound 96. $^1$H NMR (400 MHz, Methanol-D4) δ (ppm): 7.93 (d, J=8 Hz, 2H), 7.73 (d, J=8 Hz, 2H), 7.59 (d, J=8 Hz, 2H), 7.29 (d, J=8 Hz, 2H), 4.47 (m, 1H), 3.86 (m, 1H), 3.45-3.30 (m, 5H), 2.64 (t, J=8 Hz, 2H), 2.39 (m, 1H), 2.27 (m, 1H), 2.11 (m, 2H), 1.95 (m, 1H), 1.69 (m, 2H), 0.97 (d, J=8 Hz, 3H). $C_{23}H_{28}N_2O$=348.22 LCMS (M+H): m/z 349

Example 5AS (R)-4'-fluoro-N-(quinuclidin-3-yl)biphenyl-4-carboxamide TFA (Compound 97R)

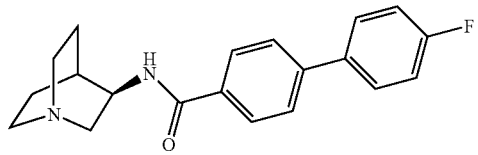 [SMILES: O=C(N[C@H]1CN2CCC1CC2)c1ccc(-c2ccc(F)cc2)cc1]

Title compound was synthesized according to the procedure used in the synthesis of Compound 19S, using 4'-fluorobiphenyl-4-carboxylic acid in place of o-methoxybenzoic acid. $^1$H NMR (400 MHz, Methanol-D4) δ (ppm): 7.95 (d, J=8 Hz, 2H), 7.70 (m, 4H), 7.21 (d, J=8 Hz, 2H), 4.47 (m, 1H), 3.86 (m, 1H), 3.45-3.31 (m, 5H), 2.39 (m, 1H), 2.27 (m, 1H), 2.11 (m, 2H), 1.95 (m, 1H). $C_{20}H_{21}FN_2O$=324.16 LCMS (M+H): m/z 325

Example 5AT (S)-4'-fluoro-N-(quinuclidin-3-yl)biphenyl-4-carboxamide TFA (Compound 132S)

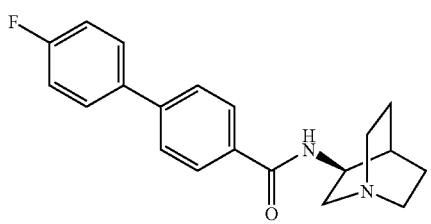 [SMILES: O=C(N[C@@H]1CN2CCC1CC2)c1ccc(-c2ccc(F)cc2)cc1]

Title compound was synthesized according to the procedure used in the synthesis of Compound 97. $^1$H NMR (400 MHz, Methanol-D4) δ (ppm): 7.95 (d, J=8 Hz, 2H), 7.71 (m, 4H), 7.21 (d, J=6 Hz, 2H), 4.47 (m, 1H), 3.86 (m, 1H), 3.45-3.30 (m, 5H), 2.39 (m, 1H), 2.28 (m, 1H), 2.12 (m, 2H), 1.96 (m, 1H). $C_{20}H_{21}FN_2O$=324.16 LCMS (M+H): m/z 325

Example 5AU (S)-4-iodo-N-(quinuclidin-3-yl)benzamide (Compound 273S)

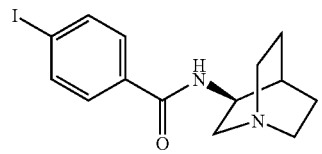 [SMILES: O=C(N[C@@H]1CN2CCC1CC2)c1ccc(I)cc1]

N,N'-Diisopropylethylamine (1.05 ml, 6.03 mmol) was added to a flask charged with DMF solution mixture of (S)-(−)-3-Aminoquinuclidine dihydrochloride (400 mg, 2.01 mmol) and 4-Iodobenzoyl chloride (616 mg, 2.31 mmol). The clear yellow solution was stirred for 3 hours. The reaction mixture was worked up by addition of 1N sodium hydroxide aqueous solution and extracted twice with ethyl acetate, combined organic layer was washed with saturated brine solution, dried over sodium sulfate, filtered, and concentrated to crude clear oil. The crude oil was purified via preparative HPLC to obtain pure product of (S)-4-iodo-N-(quinuclidin-3-yl)benzamide, (460 mg, 64% yield). $^1$H NMR (400 MHz, Methanol-D4) δ (ppm): 7.85 (d, J=8 Hz, 2H), 7.60 (d, J=8 Hz, 2H), 4.12 (m, 1H), 3.31 (m, 1H), 2.99 (m, 1H), 2.84 (m, 4H), 2.02 (m, 1H), 1.90 (m, 1H), 1.78 (m, 2H), 1.54 (m, 1H). $C_{14}H_{17}IN_2O$=356.04 LCMS (M+H): m/z 357

Example 5AV (S)—N-(quinuclidin-3-yl)-4'-(trifluoromethyl)biphenyl-4-carboxamide (Compound 274S)

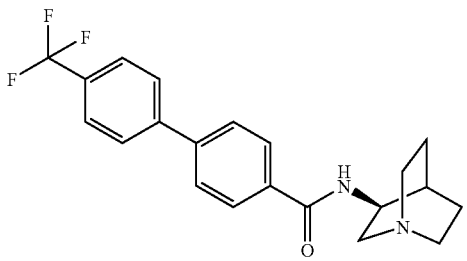 [SMILES: O=C(N[C@@H]1CN2CCC1CC2)c1ccc(-c2ccc(C(F)(F)F)cc2)cc1]

4-(trifluoromethyl)phenylboronic acid (20.9 mg, 0.11 mmol) was added to a flask charged with (S)-4-iodo-N-(quinuclidin-3-yl)benzamide (35.6 mg, 0.1 mmol), cesium carbonate (81.5 mg, 0.25 mmol) in 2 ml of Acetonitrile and 2 ml of water. The mixture was degassed by sonication for 20 minutes followed by charging catalytic amount of Palladium (II) acetate and place under nitrogen to stirred for 3 hours. The reaction mixture was filtered through pad of celite and washed with acetone, solution was concentrated under vacuum to oil. Preparative HPLC instrument was used to obtain pure (S)—N-(quinuclidin-3-yl)-4'-(trifluoromethyl) biphenyl-4-carboxamide (24.5 mg, 65% yield). $^1$H NMR (400 MHz, CDCl$_3$) δ (ppm): 7.80 (d, J=8 Hz, 2H), 7.63 (m, 4H), 7.58 (d, J=8 Hz, 2H), 6.33 (d, 1H), 4.11 (m, 1H), 3.38 (m, 1H), 2.80 (m, 4H), 2.56 (ddd, J=6, 14, 6 Hz, 1H), 2.00 (m, 1H), 1.65 (m, 3H), 1.47 (m, 1H). $C_{21}H_{21}F_3N_2O$=374.16 LCMS (M+H): m/z 375

Example 5AW (S)-3'-fluoro-N-(quinuclidin-3-yl)biphenyl-4-carboxamide (Compound 278S)

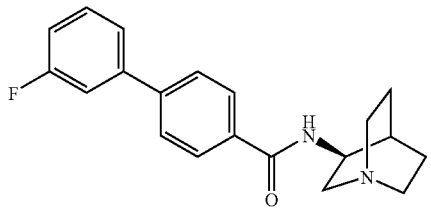 [SMILES: O=C(N[C@@H]1CN2CCC1CC2)c1ccc(-c2cccc(F)c2)cc1]

Title compound was synthesized according to the procedure used in the synthesis of compound 274, using 3-(fluoromethyl)phenylboronic acid in place of 4-(trifluoromethyl)phenylboronic acid. $^1$H NMR (400 MHz, CDCl$_3$) δ (ppm): 7.77 (d, J=8 Hz, 2H), 7.55 (d, J=8 Hz, 2H), 7.32 (m, 2H), 7.21 (m, 1H), 7.00 (m, 1H), 6.33 (d, 1H), 4.09 (m, 1H), 3.37 (m, 1H), 2.83 (m, 4H), 2.54 (m, 1H), 1.99 (m, 1H), 1.65 (m, 3H), 1.47 (m, 1H). $C_2H_{21}FN_2O$=324.16 LCMS (M+H): m/z 325

Example 5AX (S)-2'-fluoro-N-(quinuclidin-3-yl)biphenyl-4-carboxamide (Compound 279S)

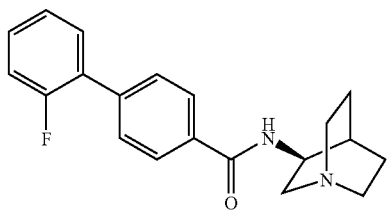 [SMILES: O=C(N[C@@H]1CN2CCC1CC2)c1ccc(-c2ccccc2F)cc1]

Title compound was synthesized according to the procedure used in the synthesis of compound 274, using 3-(fluoromethyl)phenylboronic acid in place of 4-(trifluoromethyl)phenylboronic acid. $^1$H NMR (400 MHz, CDCl$_3$) δ (ppm): 7.77 (d, J=8 Hz, 2H), 7.53 (dd, J=8 Hz, 2H), 7.32 (td, J=8 Hz, 1H), 7.28 (m, 1H), 7.12 (m, 2H), 6.34 (d, 1H), 4.08 (m, 1H), 3.37 (m, 1H), 2.793 (m, 4H), 2.53 (m, 1H), 1.98 (m, 1H), 1.64 (m, 3H), 1.44 (m, 1H). $C_2H_{21}FN_2O$=324.16 LCMS (M+H): m/z 325

Example 5AY (S)—N-(quinuclidin-3-yl)-3'-(trifluoromethyl)biphenyl-4-carboxamide (Compound 281S)

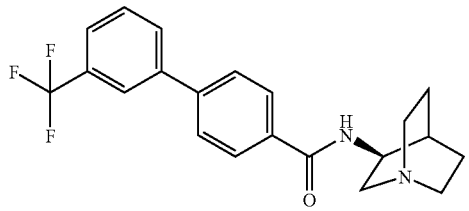 [SMILES: O=C(N[C@@H]1CN2CCC1CC2)c1ccc(-c2cccc(C(F)(F)F)c2)cc1]

Title compound was synthesized according to the procedure used in the synthesis of compound 274, using 3-(trifluoromethyl)phenylboronic in place of 4-(trifluoromethyl)phenylboronic acid. $^1$H NMR (400 MHz, CDCl$_3$) δ (ppm): 7.87 (d, J=8 Hz, 2H), 7.80 (s, 1H), 7.74 (d, J=8 Hz, 1H), 7.62 (m, 3H), 7.56 (t, J=8 Hz, 1H), 6.56 (d, 1H), 4.16 (m, 1H), 3.42 (m, 1H), 2.85 (m, 4H), 2.56 (m, 1H), 2.06 (m, 1H), 1.79 (m, 3H), 1.53 (m, 1H). $C_{21}H_{21}F_3N_2O$=374.16 LCMS (M+H): m/z 375

Example 5AZ

Compound 212

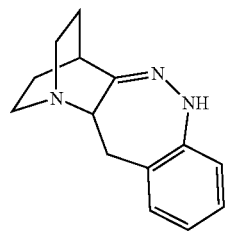 [SMILES: c1ccc2c(c1)CC1C(=NN2)C2CCN1CC2]

A catalytic amount of Palladium (II) acetate (10.9 mg, 0.05 mmol) was added to microwave reaction vial charged with 2-Methylene-3-quinuclidinone hydrochloride (174.4 mg, 1.00 mmol), Phenylhydrazine (109 mg, 1.01 mmol) in 2 ml of acetic acid. Sealed the vial with a cap then heated to 150° C. for 15 minutes. Added 1.0M K$_2$CO$_3$ and extracted with ethyl acetate 2×50 ml, combined organic layer was washed with brine solution, dried over sodium sulfate, filtered, and concentrated under vacuum. Purified by flash chromatography 0% to 10% methanol and 2% TEA in CH$_2$Cl$_2$ to recover white solid Compound 212 (12.1 mg, 5% yield) $^1$H NMR (400 MHz, CDCl$_3$) β (ppm): 7.19 (s, 1H), 7.07 (t, J=8 Hz, 2H), 6.85 (td, J=7 Hz, 1H), 6.7 (d, J=8 Hz, 1H), 3.60 (d, J=12 Hz, 1H), 3.29 (dd, J=14 Hz, 1H), 3.00 (m, 4H), 2.82 (m, 1H), 2.50 (m, 1H). $C_{14}H_{17}N_3$=277.14 LCMS (M+H): m/z 278

Compounds related to Compound 212 can be prepared according to the pathways identified in Scheme 1.

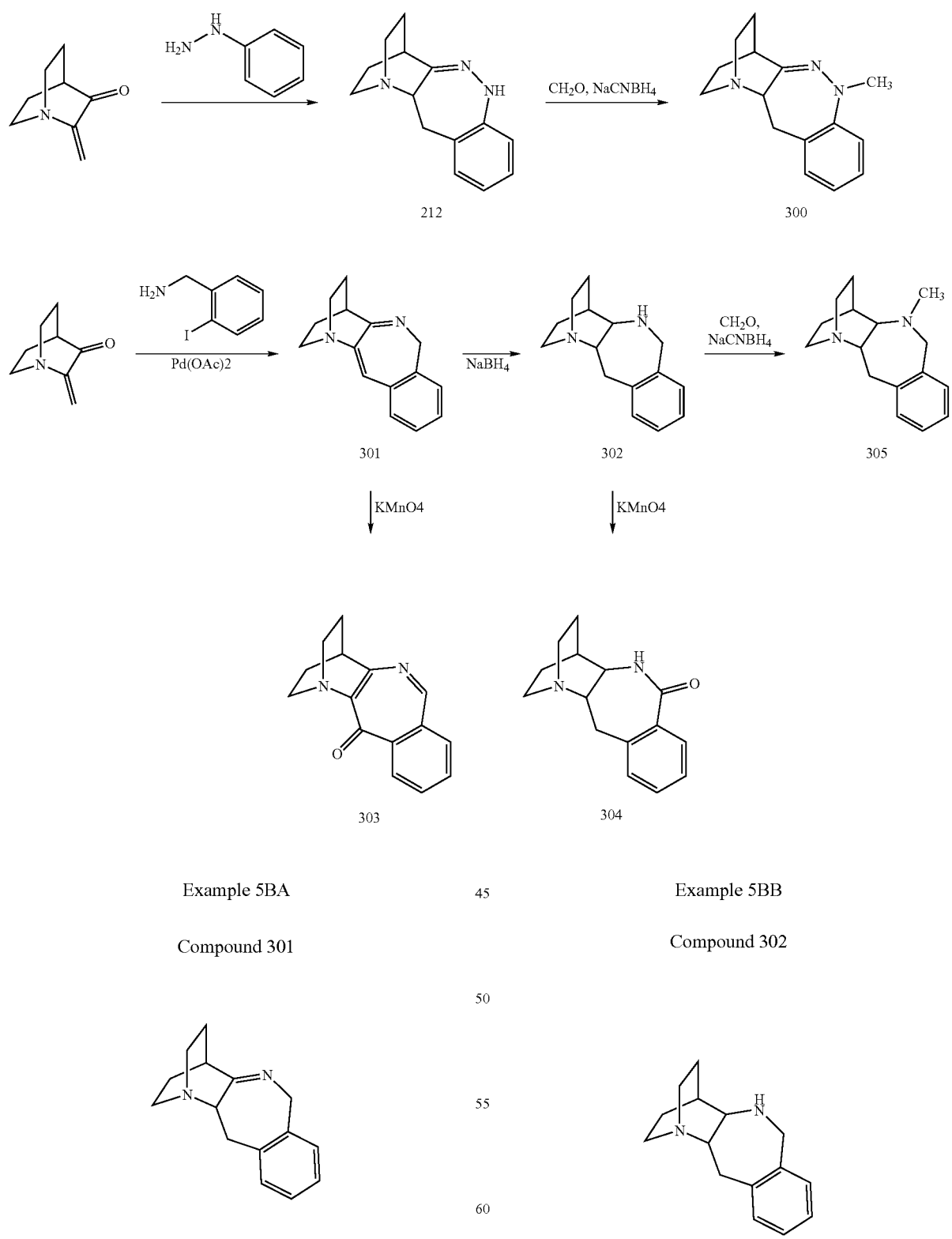

Example 5BA

Compound 301

Example 5BB

Compound 302

A solution of (2-bromophenyl)methanamine, 2-Methylene-3-quinuclidinone hydrochloride, and 1,4-Diazabicyclo[2.2.2]octane in DMF, is degassed via sonication for 20 minutes then a catalytic amount of Palladium (II) acetate is charged under nitrogen and stir at reflux to give Compound 301.

Compound 301 is reduced with sodium borohydride in THF solution to yield Compound 302.

Example 5BC

Compound 303

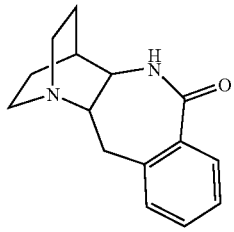 [SMILES: O=C1NC2C3CCN(CC3)C2Cc2ccccc21]

Compound 302 is oxidized with a solution of $KMnO_4$ and $MnO_2$ in DCM and stirred at room temperature to yield Compound 303.

Example 5BD

Compound 305

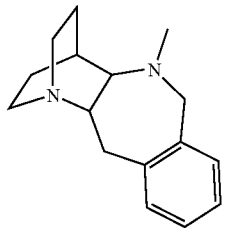 [SMILES: CN1Cc2ccccc2CC2C1C1CCN2CC1]

Compound 302 is treated with cyanoborohydride, formaldehyde, in acetic acid to yield Compound 305.

It is understood that the disclosed invention is not limited to the particular methodology, protocols and reagents described as these may vary. It is also understood that the terminology used herein is for the purposes of describing particular embodiments only and is not intended to limit the scope of the present invention which will be limited only by the appended claims.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the exemplary methods, devices, and materials are as described. All patents, patent applications and other publications cited herein and the materials for which they are cited are specifically incorporated by reference in their entireties.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of modulating the excitability of a neuronal cell comprising:
   (a) expressing in the neuronal cell a genetic construct encoding a chimeric receptor, wherein the chimeric receptor comprises
      (i) a transmembrane domain from a ligand-gated ion channel protein; and
      (ii) a ligand binding domain from an α7 nicotinic acetylcholine receptor,
         wherein the ligand binding domain from the α7 nicotinic acetylcholine receptor is fused to the transmembrane domain from the ligand-gated ion channel protein, and
         wherein the amino acid sequence of the ligand binding domain from an α7 nicotinic acetylcholine receptor comprises at least one selectivity-inducing mutation, the selectivity-inducing mutation being selected from an amino acid substitution at one or more positions 77, 79, 139, or 141 in the amino acid sequence of SEQ ID NO:1, SEQ ID NO: 6, or SEQ ID NO: 10; and
   (b) exposing the neuronal cell to a compound that activates the chimeric receptor, wherein the compound has a structure of formula I:

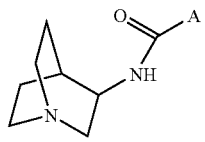

or a pharmaceutically acceptable salt thereof, wherein:
A is one of:

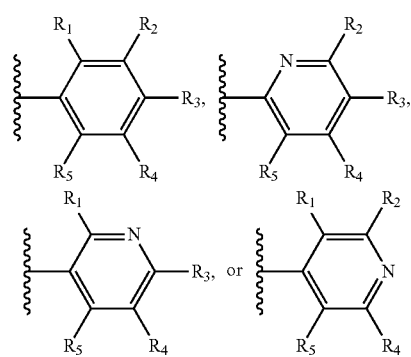

wherein,
each of $R_1$ and $R_5$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, phenoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

$R_4$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

each of $R_2$ and $R_3$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

or $R_2$ and $R_3$, together with the carbon atoms to which they are attached, form a 5 or 6-membered carbocyclic or heterocyclic ring optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl;

with the provisos that: (a) at least one of $R_1$, $R_2$, $R_3$, $R_4$ and $R_5$ is not hydrogen; and (b) if neither of $R_1$ and $R_5$ is $C_1$-$C_6$ alkoxy, then $R_3$ is present and is not hydrogen.

2. The method of claim 1, wherein the ligand-gated ion channel protein is selected from the group consisting of ionotropic nicotinic acetylcholine receptors, ionotropic serotonin receptors, ionotropic glycine receptors, and ionotropic GABA receptors.

3. The method of claim 2, wherein the ligand-gated ion channel protein is selective for cations.

4. The method of claim 3, wherein the ligand-gated ion channel protein is a 5HT3 receptor.

5. The method of claim 3, wherein the excitability of the neuron is increased.

6. The method of claim 2, wherein the ligand-gated ion channel protein is selective for anions.

7. The method of claim 6, wherein the ligand-gated ion channel protein is a glycine receptor or GABA receptor.

8. The method of claim 6, wherein the excitability of the neuron is decreased.

9. The method of claim 1, wherein the at least one mutation in the ligand binding domain is selected from the group consisting of Q79A, Q79G, L141A, L141F, L141P, W77F, W77Y, W77M, Q79C, Q79D, Q79E, Q79H, Q79L, Q79P, Q79R, Q79S, Q79T, Q79W, Q139A, Q139C, Q139D, Q139F, Q139G, Q139H, Q139I , Q139K, Q139L, Q139M, Q139N, Q139R, Q139S, Q139V, Q139W, Q139Y, L141G, L141H, L141I , L141M, L141N, L141Q, L141S, L141V, and L141W.

10. The method of claim 1, wherein the at least one mutation in the ligand binding domain is selected from the group consisting of Q79A, Q79G, L141A, L141F, L141P, W77F, W77Y, and W77M.

11. The method of claim 1, wherein the at least one selectivity-inducing mutation is selected from the group consisting of Q79A, Q79G, L141A, L141F, L141P, W77F, W77Y, and W77M in the amino acid sequence of SEQ ID NO: 1, SEQ ID NO: 6, or SEQ ID NO: 10.

12. The method of claim 1, wherein the compound does not activate a wild-type α7 nicotinic acetylcholine receptor.

13. The method of claim 12, wherein the compound is selected from the group consisting of 9S, 16S, 19S, 22S, 28S, 34S, 38R, 85S, 86S, 88S, 89S, 90S, 91S, 96R, 97R, 115S, 117S, 118S, 119S, 120S, 121S, 127S, 131S, 132S, 134S, 148S, 149S, 154S, 156S, 157S, 158S, 163S, 164S, 165S, 170R, 208S, 278S, 279S, 281S, 292R, 294S, 295S, and 296S.

14. The method of claim 1, wherein the neuronal cell is in vitro.

15. The method of claim 1, wherein at least one of $R_1$ and $R_5$ is methoxy, ethoxy or phenoxy.

16. The method of claim 1, wherein said compound of formula I is the (S)-enantiomer.

17. The method of claim 1, wherein the chimeric receptor comprises a sequence of SEQ ID NO: 2, SEQ ID NO: 7, or SEQ ID NO: 11 and the compound is selected from the group consisting of 28S, 34S, 96R, 97R, 131S, 132S, 278S, 279S, and 281S.

18. The method of claim 1, wherein the chimeric receptor comprises a sequence of SEQ ID NO: 3, SEQ ID NO: 8, or SEQ ID NO: 12 and the compound is selected from the group consisting of 9S, 16S, 22S, 38R, 115S, 117S, 134S, 148S, 149S, 154S, 156S, 157S, 158S, 163S, 164S, 165S, 170R, 292R, 295S, and 296S.

19. The method of claim 1, wherein the chimeric receptor comprises a sequence of SEQ ID NO: 4, SEQ ID NO: 9, or SEQ ID NO: 13 and the compound is selected from 19S, 85S, 86S, 88S, 89S, 90S, 91S, 118S, 119S, 120S, 121S, 127S, 208S, and 294S.

20. A chimeric receptor comprising:
(a) a transmembrane domain from a ligand-gated ion channel protein, and
(b) a ligand binding domain from an α7 nicotinic acetylcholine receptor,
   wherein the ligand binding domain from the α7 nicotinic acetylcholine receptor is fused to the transmembrane domain from the ligand-gated ion channel protein, and
   wherein the amino acid sequence of the ligand binding domain from an α7 nicotinic acetylcholine receptor comprises at least one selectivity-inducing mutation, the selectivity-inducing mutation being selected from an amino acid substitution at one or more positions 77, 79 139 or 141 in the amino acid sequence of SEQ ID NO:1, SEQ ID NO: 6, or SEQ ID NO: 10.

21. The chimeric receptor of claim 20, wherein the transmembrane domain is a transmembrane domain of a ligand-gated ion channel protein selected from the group consisting of ionotropic nicotinic acetylcholine receptors, ionotropic serotonin receptors, ionotropic glycine receptors, and ionotropic GABA receptors.

22. The chimeric receptor of claim 21, wherein the transmembrane domain is the transmembrane domain from a 5HT3receptor, the transmembrane domain of a glycine receptor, or a transmembrane domain of a GABA C receptor.

23. The chimeric receptor of claim 22, wherein the chimeric receptor comprises a sequence of SEQ ID NO: 2, SEQ ID NO: 7, or SEQ ID NO: 11.

24. The chimeric receptor of claim 23, wherein the chimeric receptor selectively binds a compound selected from the group consisting of 28S, 34S, 96R, 97R, 131S, 132S, 278S, 279S, and 281S.

25. The chimeric receptor of claim 22, wherein the chimeric receptor comprises a sequence of SEQ ID NO: 3, SEQ ID NO: 8, or SEQ ID NO: 12.

26. The chimeric receptor of claim 25, wherein the chimeric receptor selectively binds a compound selected from the group consisting of 9S, 16S, 22S, 38R, 115S, 117S, 134S, 148S, 149S, 154S, 156S, 157S, 158S, 163S, 164S, 165S, 170R, 292R, 295S, and 296S.

27. The chimeric receptor of claim 22, wherein the chimeric receptor comprises a sequence of SEQ ID NO: 4, SEQ ID NO: 9, or SEQ ID NO: 13.

28. The chimeric receptor of claim 27, wherein the chimeric receptor selectively binds a compound selected from the group consisting of 19S, 85S, 86S, 88S, 89S, 90S, 91S, 118S, 119S, 120S, 121S, 127S, 208S, 212, 241, 242, 245, 253, 254, 255, and 294S.

29. The chimeric receptor of claim 22, wherein the chimeric receptor has the amino acid sequence of SEQ ID NO: 5.

30. A kit comprising a chimeric receptor of claim 20 and at least one compound that activates the receptor, wherein the compound has a structure of formula I:

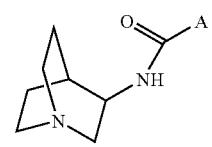

I or a pharmaceutically acceptable salt thereof, wherein:
A is one of:

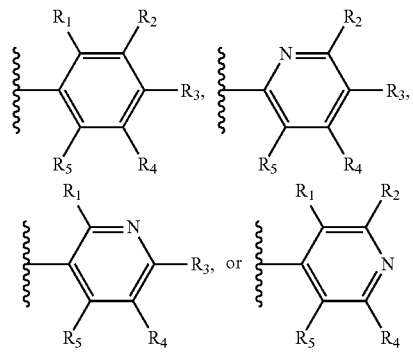

wherein,
each of $R_1$ and $R_5$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, phenoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

$R_4$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

each of $R_2$ and $R_3$ is independently selected from the group of hydrogen, halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl, aryl and heteroaryl, wherein said aryl and heteroaryl are optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino or alkylsulfonyl;

or $R_2$ and $R_3$, together with the carbon atoms to which they are attached, form a 5 or 6-membered carbocyclic or heterocyclic ring optionally substituted with halo, $C_1$-$C_6$ alkyl, $C_1$-$C_6$ alkoxy, $C_1$-$C_6$ thioalkyl, $C_1$-$C_6$ haloalkyl, $C_1$-$C_6$ thiohaloalkyl, $C_1$-$C_6$ haloalkoxy, amino, alkylamino, dialkylamino, alkylsulfonyl;

with the provisos that: (a) at least one of $R_1$, $R_2$, $R_3$, $R_4$ and $R_5$ is not hydrogen; and (b) if neither of $R_1$ and $R_5$ is $C_1$-$C_6$ alkoxy, then $R_3$ is present and is not hydrogen.

31. The kit of claim 30, wherein the chimeric receptor comprises a sequence of SEQ ID NO: 2, SEQ ID NO: 7, or SEQ ID NO: 11.

32. The kit of claim 31, wherein the compound is 28S, 34S, 96R, 97R, 131S, 132S, 278S, 279S, and/or 281S.

33. The kit of claim 30, wherein the chimeric receptor comprises a sequence of SEQ ID NO: 3, SEQ ID NO: 8, or SEQ ID NO: 12.

34. The kit of claim 33, wherein the compound is 9S, 16S, 22S, 38R, 115S, 117S, 134S, 148S, 149S, 154S, 156S, 157S, 158S, 163S, 164S, 165S, 170R, 292S, 295S, and/or 296S.

35. The kit of claim 30, wherein at least one of $R_1$ and $R_5$ is methoxy, ethoxy or phenoxy.

36. The kit of claim 30, wherein said compound of formula I is the (S)-enantiomer.

37. The kit of claim 30, wherein the chimeric receptor comprises a sequence of SEQ ID NO: 4, SEQ ID NO: 9, or SEQ ID NO: 13.

38. The kit of claim 37, wherein the compound is 19S, 85S, 86S, 88S, 89S, 90S, 91S, 118S, 119S, 120S, 121S, 127S, 208S, and/or 294S.

39. The chimeric receptor of claim 20, wherein the at least one mutation in the ligand binding domain is selected from the group consisting of Q79A, Q79G, L141A, L141F, L141P, W77F, W77Y, W77M, Q79C, Q79D, Q79E, Q79H, Q79L, Q79P, Q79R, Q79S, Q79T, Q79W, Q139A, Q139C, Q139D, Q139F, Q139G, Q139H, Q139I, Q139K, Q139L, Q139M, Q139N, Q139R, Q139S, Q139V, Q139W, Q139Y, L141G, L141H, L141I, L141M, L141N, L141Q, L141S, L141V, and L141W.

40. The chimeric receptor of claim 20, wherein the at least one mutation in the ligand binding domain is selected from the group consisting of Q79A, Q79G, L141A, L141F, L141P, W77F, W77Y, and W77M.

41. The chimeric receptor of claim 20, wherein the amino acid sequence of the ligand binding domain from an α7 nicotinic acetylcholine receptor comprises at least one selectivity-inducing mutation selected from the group consisting of Q79A, Q79G, L141A, L141F, L141P, W77F, W77Y, and W77M in the amino acid sequence of SEQ ID NO:1, SEQ ID NO: 6, or SEQ ID NO: 10.

42. The kit of claim 30, wherein the chimeric receptor has at least one mutation in the ligand binding domain selected from the group consisting of Q79A, Q79G, L141A, L141F, L141P, W77F, W77Y, W77M, Q79C, Q79D, Q79E, Q79H, Q79L, Q79P, Q79R, Q79S, Q79T, Q79W, Q139A, Q139C, Q139D, Q139F, Q139G, Q139H, Q139I, Q139K, Q139L, Q139M, Q139N, Q139R, Q139S, Q139V, Q139W, Q139Y, L141G, L141H, L141I, L141M, L141N, L141Q, L141S, L141V, and L141W.

43. The kit of claim 30, wherein the chimeric receptor has at least one mutation in the ligand binding domain selected from the group consisting of Q79A, Q79G, L141A, L141F, L141P, W77F, W77Y, and W77M.

44. The kit of claim 30, wherein the amino acid sequence of the ligand binding domain from an α7 nicotinic acetylcholine receptor comprises at least one selectivity-inducing mutation selected from the group consisting of Q79A, Q79G, L141A, L141F, L141P, W77F, W77Y, and W77M in the amino acid sequence of SEQ ID NO:1, SEQ ID NO: 6, or SEQ ID NO: 10.

45. A method of modulating the excitability of a neuronal cell comprising:
(a) expressing in the neuronal cell a genetic construct encoding a chimeric receptor, wherein the chimeric receptor comprises
(i) a transmembrane domain from a ligand-gated ion channel protein; and
(ii) a ligand binding domain from an α7 nicotinic acetylcholine receptor,
wherein the ligand binding domain from the α7 nicotinic acetylcholine receptor is fused to the transmembrane domain from the ligand-gated ion channel protein, and
wherein the amino acid sequence of the ligand binding domain from an α7 nicotinic acetylcholine receptor comprises at least one selectivity-inducing mutation, the selectivity-inducing mutation being selected from an amino acid substitution at position 141 in the amino acid sequence of SEQ ID NO:1, SEQ ID NO: 6, or SEQ ID NO: 10; and
(b) exposing the neuronal cell to a compound that activates the chimeric receptor, wherein the compound has a structure of formula II or formula III:

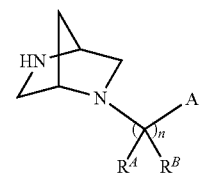

or a pharmaceutically acceptable salt thereof, wherein:
A is aryl or heteroaryl optionally substituted with halo, $C_1$-$C_6$ alkyl, $C_1$-$C_6$ alkoxy, $C_1$-$C_6$ thioalkyl, $C_1$-$C_6$ haloalkyl, furanyl or thiophenyl, wherein said furanyl and thiophenyl are optionally substituted with halo, $C_1$-$C_6$ alkyl, $C_1$-$C_6$ alkoxy, $C_1$-$C_6$ thioalkyl or $C_1$-$C_6$ haloalkyl;
each of $R^A$ and $R^B$ is hydrogen or $C_1$-$C_6$ alkyl;

or R$^A$ and R$^B$ taken together are =O; and
n is 0 or 1
or

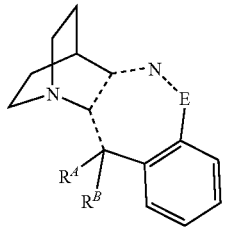

III wherein
each _____ is a single or double bond;
each R$^A$ and R$^B$ is hydrogen or R$^A$ and R$^B$ taken together are =O;
E is —N, —NH, CR$^C$, or —CR$^C$R$^D$;
each R$^C$ and R$^D$ is hydrogen or R$^C$ and R$^D$ taken together are =O;
or a pharmaceutically acceptable salt thereof;
wherein said compound does not comprise adjacent double bonds.

46. The method of claim 45, wherein the ligand-gated ion channel protein is selected from the group consisting of ionotropic nicotinic acetylcholine receptors, ionotropic serotonin receptors, ionotropic glycine receptors, and ionotropic GABA receptors.

47. The method of claim 46, wherein the ligand-gated ion channel protein is selective for cations.

48. The method of claim 47, wherein the ligand-gated ion channel protein is a 5HT3 receptor.

49. The method of claim 47, wherein the excitability of the neuron is increased.

50. The method of claim 46, wherein the ligand-gated ion channel protein is selective for anions.

51. The method of claim 50, wherein the ligand-gated ion channel protein is a glycine receptor or GABA receptor.

52. The method of claim 50, wherein the excitability of the neuron is decreased.

53. The method of claim 45, wherein the amino acid sequence of the ligand binding domain from an α7 nicotinic acetylcholine receptor comprises at least one selectivity-inducing mutation selected from the group consisting of L141A, L141F, L141P, L141G, L141H, L141I, L141M, L141N, L141Q, L141S, L141V, and L141W in the amino acid sequence of SEQ ID NO:1, SEQ ID NO: 6, or SEQ ID NO: 10.

54. The method of claim 45, wherein the amino acid sequence of the ligand binding domain from an α7 nicotinic acetylcholine receptor comprises at least one selectivity-inducing mutation selected from the group consisting of L141A, L141F, and L141P in the amino acid sequence of SEQ ID NO:1, SEQ ID NO: 6, or SEQ ID NO: 10.

55. The method of claim 54, wherein the compound is selected from the group consisting of 212, 241, 242, 253, and 254.

56. A kit comprising a chimeric receptor and at least one compound that activates the receptor, wherein the chimeric receptor comprises
a transmembrane domain from a ligand-gated ion channel protein; and
a ligand binding domain from an α7 nicotinic acetylcholine receptor,
wherein the ligand binding domain from the α7 nicotinic acetylcholine receptor is fused to the transmembrane domain from the ligand-gated ion channel protein, and
wherein the amino acid sequence of the ligand binding domain from an α7 nicotinic acetylcholine receptor comprises at least one selectivity-inducing mutation, the selectivity-inducing mutation being selected from an amino acid substitution at one or more positions 77, 79, 139, or 141 in the amino acid sequence of SEQ ID NO:1, SEQ ID NO: 6, or SEQ ID NO: 10; and
wherein the compound has a structure of formula II or formula III:

II

III or a pharmaceutically acceptable salt thereof, wherein:
A is aryl or heteroaryl optionally substituted with halo, C$_1$-C$_6$ alkyl, C$_1$-C$_6$ alkoxy, C$_1$-C$_6$ thioalkyl, C$_1$-C$_6$ haloalkyl, furanyl or thiophenyl, wherein said furanyl and thiophenyl are optionally substituted with halo, C$_1$-C$_6$ alkyl, C$_1$-C$_6$ alkoxy, C$_1$-C$_6$ thioalkyl or C$_1$-C$_6$ haloalkyl;
each of R$^A$ and R$^B$ is hydrogen or C$_1$-C$_6$ alkyl;
or R$^A$ and R$^B$ taken together are =O; and
n is 0 or 1
or wherein
each _____ is a single or double bond;
each R$^A$ and R$^B$ is hydrogen or R$^A$ and R$^B$ taken together are =O;
E is —N, —NH, CR$^C$, or —CR$^C$R$^D$;
each R$^C$ and R$^D$ is hydrogen or R$^C$ and R$^D$ taken together are =O;
or a pharmaceutically acceptable salt thereof;
wherein said compound does not comprise adjacent double bonds.

57. The kit of claim 56, wherein the chimeric receptor has at least one mutation in the ligand binding domain selected from the group consisting of L141A, L141F, L141P, L141G, L141H, L141I, L141M, L141N, L141Q, L141S, L141V, and L141W.

58. The kit of claim 56, wherein the amino acid sequence of the ligand binding domain from an α7 nicotinic acetylcholine receptor comprises at least one selectivity-inducing mutation selected from the group consisting of L141A, L141F, and L141P in the amino acid sequence of SEQ ID NO:1, SEQ ID NO: 6, or SEQ ID NO: 10.

59. The kit of claim 58, wherein the compound is 212, 241, 242, 253, and/or 254.

60. The kit of claim 56, wherein the chimeric receptor comprises a sequence of SEQ ID NO: 4, SEQ ID NO: 9, or SEQ ID NO: 13.

* * * * *

SEQUENCE LISTING

```
<160> NUMBER OF SEQ ID NOS: 13

<210> SEQ ID NO 1
<211> LENGTH: 471
<212> TYPE: PRT
<213> ORGANISM: Artificial Sequence
<220> FEATURE:
<223> OTHER INFORMATION: Human nAChR LBD/mouse serotonin receptor 3
      chimera

<400> SEQUENCE: 1

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125
```

-continued

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
        210                 215                 220

Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
                245                 250                 255

Asp Ser Gly Glu Arg Val Ser Phe Lys Ile Thr Leu Leu Leu Gly Tyr
                260                 265                 270

Ser Val Phe Leu Ile Ile Val Ser Asp Thr Leu Pro Ala Thr Ile Gly
            275                 280                 285

Thr Pro Leu Ile Gly Val Tyr Phe Val Val Cys Met Ala Leu Leu Val
        290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
                325                 330                 335

Arg Ile Ala Trp Ile Leu Cys Leu Gly Glu Gln Pro Met Ala His Arg
            340                 345                 350

Pro Pro Ala Thr Phe Gln Ala Asn Lys Thr Asp Asp Cys Ser Gly Ser
        355                 360                 365

Asp Leu Leu Pro Ala Met Gly Asn His Cys Ser His Val Gly Gly Pro
370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
                405                 410                 415

Ser Ile Arg His Phe Leu Glu Lys Arg Asp Glu Met Arg Glu Val Ala
            420                 425                 430

Arg Asp Trp Leu Arg Val Gly Tyr Val Leu Asp Arg Leu Leu Phe Arg
        435                 440                 445

Ile Tyr Leu Leu Ala Val Leu Ala Tyr Ser Ile Thr Leu Val Thr Leu
450                 455                 460

Trp Ser Ile Trp His Tyr Ser
465                 470

<210> SEQ ID NO 2
<211> LENGTH: 471
<212> TYPE: PRT
<213> ORGANISM: Artificial Sequence
<220> FEATURE:
<223> OTHER INFORMATION: Human nAChR LBD/mouse serotonin receptor 3
      chimera W77F mutant

<400> SEQUENCE: 2

Met Arg Cys Ser Pro Gly Gly Val Trp Leu Ala Leu Ala Ala Ser Leu
1               5                   10                  15

```
Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Phe Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
                245                 250                 255

Asp Ser Gly Glu Arg Val Ser Phe Lys Ile Thr Leu Leu Leu Gly Tyr
            260                 265                 270

Ser Val Phe Leu Ile Ile Val Ser Asp Thr Leu Pro Ala Thr Ile Gly
        275                 280                 285

Thr Pro Leu Ile Gly Val Tyr Phe Val Val Cys Met Ala Leu Leu Val
    290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
                325                 330                 335

Arg Ile Ala Trp Ile Leu Cys Leu Gly Glu Gln Pro Met Ala His Arg
            340                 345                 350

Pro Pro Ala Thr Phe Gln Ala Asn Lys Thr Asp Asp Cys Ser Gly Ser
        355                 360                 365

Asp Leu Leu Pro Ala Met Gly Asn His Cys Ser His Val Gly Gly Pro
    370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
                405                 410                 415

Ser Ile Arg His Phe Leu Glu Lys Arg Asp Glu Met Arg Glu Val Ala
            420                 425                 430

Arg Asp Trp Leu Arg Val Gly Tyr Val Leu Asp Arg Leu Leu Phe Arg
        435                 440                 445
```

```
Ile Tyr Leu Leu Ala Val Leu Ala Tyr Ser Ile Thr Leu Val Thr Leu
    450                 455                 460

Trp Ser Ile Trp His Tyr Ser
465                 470

<210> SEQ ID NO 3
<211> LENGTH: 471
<212> TYPE: PRT
<213> ORGANISM: Artificial Sequence
<220> FEATURE:
<223> OTHER INFORMATION: Human nAChR LBD/mouse serotonin receptor 3
      chimera Q79G mutant

<400> SEQUENCE: 3

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gly Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
                245                 250                 255

Asp Ser Gly Glu Arg Val Ser Phe Lys Ile Thr Leu Leu Leu Gly Tyr
            260                 265                 270

Ser Val Phe Leu Ile Ile Val Ser Asp Thr Leu Pro Ala Thr Ile Gly
        275                 280                 285

Thr Pro Leu Ile Gly Val Tyr Phe Val Val Cys Met Ala Leu Leu Val
    290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
                325                 330                 335
```

```
Arg Ile Ala Trp Ile Leu Cys Leu Gly Glu Gln Pro Met Ala His Arg
            340                 345                 350

Pro Pro Ala Thr Phe Gln Ala Asn Lys Thr Asp Asp Cys Ser Gly Ser
            355                 360                 365

Asp Leu Leu Pro Ala Met Gly Asn His Cys Ser His Val Gly Gly Pro
            370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
            405                 410                 415

Ser Ile Arg His Phe Leu Glu Lys Arg Asp Glu Met Arg Glu Val Ala
            420                 425                 430

Arg Asp Trp Leu Arg Val Gly Tyr Val Leu Asp Arg Leu Leu Phe Arg
            435                 440                 445

Ile Tyr Leu Leu Ala Val Leu Ala Tyr Ser Ile Thr Leu Val Thr Leu
            450                 455                 460

Trp Ser Ile Trp His Tyr Ser
465                 470

<210> SEQ ID NO 4
<211> LENGTH: 471
<212> TYPE: PRT
<213> ORGANISM: Artificial Sequence
<220> FEATURE:
<223> OTHER INFORMATION: Human nAChR LBD/mouse serotonin receptor 3
      chimera L141F mutant

<400> SEQUENCE: 4

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
            85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Phe Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
            165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220
```

```
Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
            245                 250                 255

Asp Ser Gly Glu Arg Val Ser Phe Lys Ile Thr Leu Leu Leu Gly Tyr
        260                 265                 270

Ser Val Phe Leu Ile Ile Val Ser Asp Thr Leu Pro Ala Thr Ile Gly
    275                 280                 285

Thr Pro Leu Ile Gly Val Tyr Phe Val Val Cys Met Ala Leu Leu Val
290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
            325                 330                 335

Arg Ile Ala Trp Ile Leu Cys Leu Gly Glu Gln Pro Met Ala His Arg
        340                 345                 350

Pro Pro Ala Thr Phe Gln Ala Asn Lys Thr Asp Asp Cys Ser Gly Ser
    355                 360                 365

Asp Leu Leu Pro Ala Met Gly Asn His Cys Ser His Val Gly Gly Pro
370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
            405                 410                 415

Ser Ile Arg His Phe Leu Glu Lys Arg Asp Glu Met Arg Glu Val Ala
        420                 425                 430

Arg Asp Trp Leu Arg Val Gly Tyr Val Leu Asp Arg Leu Leu Phe Arg
    435                 440                 445

Ile Tyr Leu Leu Ala Val Leu Ala Tyr Ser Ile Thr Leu Val Thr Leu
450                 455                 460

Trp Ser Ile Trp His Tyr Ser
465                 470

<210> SEQ ID NO 5
<211> LENGTH: 471
<212> TYPE: PRT
<213> ORGANISM: Artificial Sequence
<220> FEATURE:
<223> OTHER INFORMATION: Human nAChR LBD/mouse serotonin receptor 3
      chimera L141F/L276G double mutant

<400> SEQUENCE: 5

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
            85                  90                  95

Val Lys Thr Val Arg Phe Pro Asp Gly Gln Ile Trp Lys Pro Asp Ile
        100                 105                 110
```

Leu Leu Tyr Asn Ser Ala Asp Glu Arg Phe Asp Ala Thr Phe His Thr
         115                 120                 125

Asn Val Leu Val Asn Ser Ser Gly His Cys Gln Tyr Phe Pro Pro Gly
     130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Ile Ile Arg Arg Arg Pro Leu Phe Tyr Ala Val Ser Leu Leu Leu Pro
225                 230                 235                 240

Ser Ile Phe Leu Met Val Val Asp Ile Val Gly Phe Cys Leu Pro Pro
                245                 250                 255

Asp Ser Gly Glu Arg Val Ser Phe Lys Ile Thr Leu Leu Leu Gly Tyr
            260                 265                 270

Ser Val Phe Gly Ile Ile Val Ser Asp Thr Leu Pro Ala Thr Ile Gly
        275                 280                 285

Thr Pro Leu Ile Gly Val Tyr Phe Val Val Cys Met Ala Leu Leu Val
    290                 295                 300

Ile Ser Leu Ala Glu Thr Ile Phe Ile Val Arg Leu Val His Lys Gln
305                 310                 315                 320

Asp Leu Gln Arg Pro Val Pro Asp Trp Leu Arg His Leu Val Leu Asp
                325                 330                 335

Arg Ile Ala Trp Ile Leu Cys Leu Gly Glu Gln Pro Met Ala His Arg
            340                 345                 350

Pro Pro Ala Thr Phe Gln Ala Asn Lys Thr Asp Asp Cys Ser Gly Ser
        355                 360                 365

Asp Leu Leu Pro Ala Met Gly Asn His Cys Ser His Val Gly Gly Pro
    370                 375                 380

Gln Asp Leu Glu Lys Thr Pro Arg Gly Arg Gly Ser Pro Leu Pro Pro
385                 390                 395                 400

Pro Arg Glu Ala Ser Leu Ala Val Arg Gly Leu Leu Gln Glu Leu Ser
                405                 410                 415

Ser Ile Arg His Phe Leu Glu Lys Arg Asp Glu Met Arg Glu Val Ala
            420                 425                 430

Arg Asp Trp Leu Arg Val Gly Tyr Val Leu Asp Arg Leu Leu Phe Arg
        435                 440                 445

Ile Tyr Leu Leu Ala Val Leu Ala Tyr Ser Ile Thr Leu Val Thr Leu
    450                 455                 460

Trp Ser Ile Trp His Tyr Ser
465                 470

<210> SEQ ID NO 6
<211> LENGTH: 431
<212> TYPE: PRT
<213> ORGANISM: Artificial Sequence
<220> FEATURE:
<223> OTHER INFORMATION: Human nAChR LBD/human glycine receptor 1
      chimera

<400> SEQUENCE: 6

```
Met Arg Cys Ser Pro Gly Gly Val Trp Leu Ala Leu Ala Ala Ser Leu
 1               5                  10                  15
Leu His Val Ser Leu Gln Gly Glu Phe Gln Arg Lys Leu Tyr Lys Glu
             20                  25                  30
Leu Val Lys Asn Tyr Asn Pro Leu Glu Arg Pro Val Ala Asn Asp Ser
             35                  40                  45
Gln Pro Leu Thr Val Tyr Phe Ser Leu Ser Leu Leu Gln Ile Met Asp
 50                  55                  60
Val Asp Glu Lys Asn Gln Val Leu Thr Thr Asn Ile Trp Leu Gln Met
 65                  70                  75                  80
Ser Trp Thr Asp His Tyr Leu Gln Trp Asn Val Ser Glu Tyr Pro Gly
                 85                  90                  95
Val Lys Thr Val Arg Phe Pro Asp Gly Gln Ile Trp Lys Pro Asp Ile
                100                 105                 110
Leu Leu Tyr Asn Ser Ala Asp Glu Arg Phe Asp Ala Thr Phe His Thr
            115                 120                 125
Asn Val Leu Val Asn Ser Ser Gly His Cys Gln Tyr Leu Pro Pro Gly
            130                 135                 140
Ile Phe Lys Ser Ser Cys Tyr Ile Asp Val Arg Trp Phe Pro Phe Asp
145                 150                 155                 160
Val Gln His Cys Lys Leu Lys Phe Gly Ser Trp Ser Tyr Gly Gly Trp
                165                 170                 175
Ser Leu Asp Leu Gln Met Gln Glu Ala Asp Ile Ser Gly Tyr Ile Pro
            180                 185                 190
Asn Gly Glu Trp Asp Leu Val Gly Ile Pro Gly Lys Arg Ser Glu Arg
            195                 200                 205
Phe Tyr Glu Cys Cys Lys Glu Pro Tyr Pro Asp Val Thr Phe Thr Val
            210                 215                 220
Thr Met Arg Arg Arg Met Gly Tyr Tyr Leu Ile Gln Met Tyr Ile Pro
225                 230                 235                 240
Ser Leu Leu Ile Val Ile Leu Ser Trp Ile Ser Phe Trp Ile Asn Met
                245                 250                 255
Asp Ala Ala Pro Ala Arg Val Gly Leu Gly Ile Thr Thr Val Leu Thr
            260                 265                 270
Met Thr Thr Gln Ser Ser Gly Ser Arg Ala Ser Leu Pro Lys Val Ser
            275                 280                 285
Tyr Val Lys Ala Ile Asp Ile Trp Met Ala Val Cys Leu Leu Phe Val
            290                 295                 300
Phe Ser Ala Leu Leu Glu Tyr Ala Ala Val Asn Phe Val Ser Arg Gln
305                 310                 315                 320
His Lys Glu Leu Leu Arg Phe Arg Arg Lys Arg Arg His His Lys Glu
                325                 330                 335
Asp Glu Ala Gly Glu Gly Arg Phe Asn Phe Ser Ala Tyr Gly Met Gly
            340                 345                 350
Pro Ala Cys Leu Gln Ala Lys Asp Gly Ile Ser Val Lys Gly Ala Asn
            355                 360                 365
Asn Ser Asn Thr Thr Asn Pro Pro Ala Pro Ser Lys Ser Pro Glu
            370                 375                 380
Glu Met Arg Lys Leu Phe Ile Gln Arg Ala Lys Lys Ile Asp Lys Ile
385                 390                 395                 400
Ser Arg Ile Gly Phe Pro Met Ala Phe Leu Ile Phe Asn Met Phe Tyr
                405                 410                 415
Trp Ile Ile Tyr Lys Ile Val Arg Arg Glu Asp Val His Asn Gln
```

<210> SEQ ID NO 7
<211> LENGTH: 431
<212> TYPE: PRT
<213> ORGANISM: Artificial Sequence
<220> FEATURE:
<223> OTHER INFORMATION: Human nAChR LBD/human glycine receptor 1 chimera W77F mutant

<400> SEQUENCE: 7

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Phe Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
    290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg Arg His His Lys Glu
                325                 330                 335

Asp Glu Ala Gly Glu Gly Arg Phe Asn Phe Ser Ala Tyr Gly Met Gly
            340                 345                 350

Pro Ala Cys Leu Gln Ala Lys Asp Gly Ile Ser Val Lys Gly Ala Asn
```

```
                355                 360                 365
Asn Ser Asn Thr Thr Asn Pro Pro Ala Pro Ser Lys Ser Pro Glu
            370                 375                 380

Glu Met Arg Lys Leu Phe Ile Gln Arg Ala Lys Lys Ile Asp Lys Ile
385                 390                 395                 400

Ser Arg Ile Gly Phe Pro Met Ala Phe Leu Ile Phe Asn Met Phe Tyr
                405                 410                 415

Trp Ile Ile Tyr Lys Ile Val Arg Glu Asp Val His Asn Gln
            420                 425                 430

<210> SEQ ID NO 8
<211> LENGTH: 431
<212> TYPE: PRT
<213> ORGANISM: Artificial Sequence
<220> FEATURE:
<223> OTHER INFORMATION: Human nAChR LBD/human glycine receptor 1
      chimera Q79G mutant

<400> SEQUENCE: 8

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gly Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Thr Met Arg Arg Arg Met Gly Tyr Tyr Leu Ile Gln Met Tyr Ile Pro
225                 230                 235                 240

Ser Leu Leu Ile Val Ile Leu Ser Trp Ile Ser Phe Trp Ile Asn Met
                245                 250                 255

Asp Ala Ala Pro Ala Arg Val Gly Leu Gly Ile Thr Thr Val Leu Thr
            260                 265                 270

Met Thr Thr Gln Ser Ser Gly Ser Arg Ala Ser Leu Pro Lys Val Ser
        275                 280                 285

Tyr Val Lys Ala Ile Asp Ile Trp Met Ala Val Cys Leu Leu Phe Val
```

```
                290                 295                 300
Phe Ser Ala Leu Leu Glu Tyr Ala Ala Val Asn Phe Val Ser Arg Gln
305                 310                 315                 320

His Lys Glu Leu Leu Arg Phe Arg Arg Lys Arg His His Lys Glu
                325                 330                 335

Asp Glu Ala Gly Glu Gly Arg Phe Asn Phe Ser Ala Tyr Gly Met Gly
                340                 345                 350

Pro Ala Cys Leu Gln Ala Lys Asp Gly Ile Ser Val Lys Gly Ala Asn
                355                 360                 365

Asn Ser Asn Thr Thr Asn Pro Pro Ala Pro Ser Lys Ser Pro Glu
            370                 375                 380

Glu Met Arg Lys Leu Phe Ile Gln Arg Ala Lys Lys Ile Asp Lys Ile
385                 390                 395                 400

Ser Arg Ile Gly Phe Pro Met Ala Phe Leu Ile Phe Asn Met Phe Tyr
                405                 410                 415

Trp Ile Ile Tyr Lys Ile Val Arg Arg Glu Asp Val His Asn Gln
                420                 425                 430

<210> SEQ ID NO 9
<211> LENGTH: 431
<212> TYPE: PRT
<213> ORGANISM: Artificial Sequence
<220> FEATURE:
<223> OTHER INFORMATION: Human nAChR LBD/human glycine receptor 1
      chimera L141F mutant

<400> SEQUENCE: 9

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Phe Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
                195                 200                 205

Phe Tyr Glu Cys Cys Lys Glu Pro Tyr Pro Asp Val Thr Phe Thr Val
    210                 215                 220

Thr Met Arg Arg Arg Met Gly Tyr Tyr Leu Ile Gln Met Tyr Ile Pro
```

```
                225                 230                 235                 240
Ser Leu Leu Ile Val Ile Leu Ser Trp Ile Ser Phe Trp Ile Asn Met
                    245                 250                 255

Asp Ala Ala Pro Ala Arg Val Gly Leu Gly Ile Thr Thr Val Leu Thr
                260                 265                 270

Met Thr Thr Gln Ser Ser Gly Ser Arg Ala Ser Leu Pro Lys Val Ser
            275                 280                 285

Tyr Val Lys Ala Ile Asp Ile Trp Met Ala Val Cys Leu Leu Phe Val
        290                 295                 300

Phe Ser Ala Leu Leu Glu Tyr Ala Ala Val Asn Phe Val Ser Arg Gln
305                 310                 315                 320

His Lys Glu Leu Leu Arg Phe Arg Lys Arg Arg His His Lys Glu
                325                 330                 335

Asp Glu Ala Gly Glu Gly Arg Phe Asn Phe Ser Ala Tyr Gly Met Gly
                340                 345                 350

Pro Ala Cys Leu Gln Ala Lys Asp Gly Ile Ser Val Lys Gly Ala Asn
            355                 360                 365

Asn Ser Asn Thr Thr Asn Pro Pro Ala Pro Ser Lys Ser Pro Glu
        370                 375                 380

Glu Met Arg Lys Leu Phe Ile Gln Arg Ala Lys Lys Ile Asp Lys Ile
385                 390                 395                 400

Ser Arg Ile Gly Phe Pro Met Ala Phe Leu Ile Phe Asn Met Phe Tyr
                405                 410                 415

Trp Ile Ile Tyr Lys Ile Val Arg Arg Glu Asp Val His Asn Gln
                420                 425                 430

<210> SEQ ID NO 10
<211> LENGTH: 428
<212> TYPE: PRT
<213> ORGANISM: Artificial Sequence
<220> FEATURE:
<223> OTHER INFORMATION: Amino acid sequence of the wild-type chimeric
      receptor between the alpha 7-nicotinic acetylcholine receptor and
      the GABA C ion channel domain

<400> SEQUENCE: 10

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160
```

```
Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Leu Leu Gln Thr Tyr Phe Pro
225                 230                 235                 240

Ala Thr Leu Met Val Met Leu Ser Trp Val Ser Phe Trp Ile Asp Arg
            245                 250                 255

Arg Ala Val Pro Ala Arg Val Pro Leu Gly Ile Thr Thr Val Leu Thr
            260                 265                 270

Met Ser Thr Ile Ile Thr Gly Val Asn Ala Ser Met Pro Arg Val Ser
            275                 280                 285

Tyr Ile Lys Ala Val Asp Ile Tyr Leu Trp Val Ser Phe Val Phe Val
            290                 295                 300

Phe Leu Ser Val Leu Glu Tyr Ala Ala Val Asn Tyr Leu Thr Thr Val
305                 310                 315                 320

Gln Glu Arg Lys Glu Gln Lys Leu Arg Glu Lys Leu Pro Cys Thr Ser
            325                 330                 335

Gly Leu Pro Pro Arg Thr Ala Met Leu Asp Gly Asn Tyr Ser Asp
            340                 345                 350

Gly Glu Val Asn Asp Leu Asp Asn Tyr Met Pro Glu Asn Gly Glu Lys
            355                 360                 365

Pro Asp Arg Met Met Val Gln Leu Thr Leu Ala Ser Glu Arg Ser Ser
370                 375                 380

Pro Gln Arg Lys Ser Gln Arg Ser Ser Tyr Val Ser Met Arg Ile Asp
385                 390                 395                 400

Thr His Ala Ile Asp Lys Tyr Ser Arg Ile Ile Phe Pro Ala Ala Tyr
            405                 410                 415

Ile Leu Phe Asn Leu Ile Tyr Trp Ser Ile Phe Ser
            420                 425

<210> SEQ ID NO 11
<211> LENGTH: 428
<212> TYPE: PRT
<213> ORGANISM: Artificial Sequence
<220> FEATURE:
<223> OTHER INFORMATION: W77F mutant amino acid sequence of the
      wild-type chimeric receptor between the alpha 7-nicotinic
      acetylcholine receptor and the GABA C ion channel domain

<400> SEQUENCE: 11

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
    50                  55                  60

Val Asp Glu Lys Asn Gln Val Leu Thr Thr Asn Ile Phe Leu Gln Met
65                  70                  75                  80

Ser Trp Thr Asp His Tyr Leu Gln Trp Asn Val Ser Glu Tyr Pro Gly
                85                  90                  95
```

```
Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Leu Leu Gln Thr Tyr Phe Pro
225                 230                 235                 240

Ala Thr Leu Met Val Met Leu Ser Trp Val Ser Phe Trp Ile Asp Arg
                245                 250                 255

Arg Ala Val Pro Ala Arg Val Pro Leu Gly Ile Thr Thr Val Leu Thr
            260                 265                 270

Met Ser Thr Ile Ile Thr Gly Val Asn Ala Ser Met Pro Arg Val Ser
            275                 280                 285

Tyr Ile Lys Ala Val Asp Ile Tyr Leu Trp Val Ser Phe Val Phe Val
            290                 295                 300

Phe Leu Ser Val Leu Glu Tyr Ala Ala Val Asn Tyr Leu Thr Thr Val
305                 310                 315                 320

Gln Glu Arg Lys Glu Gln Lys Leu Arg Glu Lys Leu Pro Cys Thr Ser
                325                 330                 335

Gly Leu Pro Pro Pro Arg Thr Ala Met Leu Asp Gly Asn Tyr Ser Asp
            340                 345                 350

Gly Glu Val Asn Asp Leu Asp Asn Tyr Met Pro Glu Asn Gly Glu Lys
            355                 360                 365

Pro Asp Arg Met Met Val Gln Leu Thr Leu Ala Ser Glu Arg Ser Ser
            370                 375                 380

Pro Gln Arg Lys Ser Gln Arg Ser Ser Tyr Val Ser Met Arg Ile Asp
385                 390                 395                 400

Thr His Ala Ile Asp Lys Tyr Ser Arg Ile Ile Phe Pro Ala Ala Tyr
                405                 410                 415

Ile Leu Phe Asn Leu Ile Tyr Trp Ser Ile Phe Ser
            420                 425

<210> SEQ ID NO 12
<211> LENGTH: 428
<212> TYPE: PRT
<213> ORGANISM: Artificial Sequence
<220> FEATURE:
<223> OTHER INFORMATION: Q79G mutant amino acid sequence of the
      wild-type chimeric receptor between the alpha 7-nicotinic
      acetylcholine receptor and the GABA C ion channel domain

<400> SEQUENCE: 12

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
```

```
                    20                  25                  30
Leu Val Lys Asn Tyr Asn Pro Leu Glu Arg Pro Val Ala Asn Asp Ser
             35                  40                  45

Gln Pro Leu Thr Val Tyr Phe Ser Leu Ser Leu Gln Ile Met Asp
 50                  55                  60

Val Asp Glu Lys Asn Gln Val Leu Thr Thr Asn Ile Trp Leu Gly Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Thr Met Arg Arg Arg Thr Leu Tyr Tyr Leu Leu Gln Thr Tyr Phe Pro
225                 230                 235                 240

Ala Thr Leu Met Val Met Leu Ser Trp Val Ser Phe Trp Ile Asp Arg
                245                 250                 255

Arg Ala Val Pro Ala Arg Val Pro Leu Gly Ile Thr Thr Val Leu Thr
            260                 265                 270

Met Ser Thr Ile Ile Thr Gly Val Asn Ala Ser Met Pro Arg Val Ser
            275                 280                 285

Tyr Ile Lys Ala Val Asp Ile Tyr Leu Trp Val Ser Phe Val Phe Val
            290                 295                 300

Phe Leu Ser Val Leu Glu Tyr Ala Ala Val Asn Tyr Leu Thr Thr Val
305                 310                 315                 320

Gln Glu Arg Lys Glu Gln Lys Leu Arg Glu Lys Leu Pro Cys Thr Ser
                325                 330                 335

Gly Leu Pro Pro Pro Arg Thr Ala Met Leu Asp Gly Asn Tyr Ser Asp
            340                 345                 350

Gly Glu Val Asn Asp Leu Asp Asn Tyr Met Pro Glu Asn Gly Glu Lys
            355                 360                 365

Pro Asp Arg Met Met Val Gln Leu Thr Leu Ala Ser Glu Arg Ser Ser
            370                 375                 380

Pro Gln Arg Lys Ser Gln Arg Ser Ser Tyr Val Ser Met Arg Ile Asp
385                 390                 395                 400

Thr His Ala Ile Asp Lys Tyr Ser Arg Ile Ile Phe Pro Ala Ala Tyr
                405                 410                 415

Ile Leu Phe Asn Leu Ile Tyr Trp Ser Ile Phe Ser
            420                 425

<210> SEQ ID NO 13
<211> LENGTH: 428
```

```
<212> TYPE: PRT
<213> ORGANISM: Artificial Sequence
<220> FEATURE:
<223> OTHER INFORMATION: L141F amino acid sequence of the wild-type
      chimeric receptor between the alpha 7-nicotinic acetylcholine
      receptor and the GABA C ion channel domain

<400> SEQUENCE: 13

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Phe Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
210                 215                 220

Thr Met Arg Arg Arg Thr Leu Tyr Tyr Leu Leu Gln Thr Tyr Phe Pro
225                 230                 235                 240

Ala Thr Leu Met Val Met Leu Ser Trp Val Ser Phe Trp Ile Asp Arg
                245                 250                 255

Arg Ala Val Pro Ala Arg Val Pro Leu Gly Ile Thr Thr Val Leu Thr
                260                 265                 270

Met Ser Thr Ile Ile Thr Gly Val Asn Ala Ser Met Pro Arg Val Ser
            275                 280                 285

Tyr Ile Lys Ala Val Asp Ile Tyr Leu Trp Val Ser Phe Val Phe Val
290                 295                 300

Phe Leu Ser Val Leu Glu Tyr Ala Ala Val Asn Tyr Leu Thr Thr Val
305                 310                 315                 320

Gln Glu Arg Lys Glu Gln Lys Leu Arg Glu Lys Leu Pro Cys Thr Ser
                325                 330                 335

Gly Leu Pro Pro Pro Arg Thr Ala Met Leu Asp Gly Asn Tyr Ser Asp
                340                 345                 350

Gly Glu Val Asn Asp Leu Asp Asn Tyr Met Pro Glu Asn Gly Glu Lys
            355                 360                 365

Pro Asp Arg Met Met Val Gln Leu Thr Leu Ala Ser Glu Arg Ser Ser
            370                 375                 380
```

```
Pro Gln Arg Lys Ser Gln Arg Ser Ser Tyr Val Ser Met Arg Ile Asp
385                 390                 395                 400

Thr His Ala Ile Asp Lys Tyr Ser Arg Ile Ile Phe Pro Ala Ala Tyr
                405                 410                 415

Ile Leu Phe Asn Leu Ile Tyr Trp Ser Ile Phe Ser
            420                 425
```